United States Patent
Ackermann, Jr. et al.

(10) Patent No.: US 9,504,645 B2
(45) Date of Patent: Nov. 29, 2016

(54) PHARMACEUTICAL FORMULATIONS FOR TREATING OCULAR CONDITIONS

(71) Applicant: Oyster Point Pharma, Inc., South San Francisco, CA (US)

(72) Inventors: Douglas Michael Ackermann, Jr., San Francisco, CA (US); James Loudin, Houston, TX (US); Kenneth J. Mandell, Arlington, MA (US)

(73) Assignee: OYSTER POINT PHARMA, INC., South San Francisco, CA (US)

( * ) Notice: Subject to any disclaimer, the term of this patent is extended or adjusted under 35 U.S.C. 154(b) by 0 days.

(21) Appl. No.: 14/887,259

(22) Filed: Oct. 19, 2015

(65) Prior Publication Data

US 2016/0106746 A1   Apr. 21, 2016

Related U.S. Application Data

(60) Provisional application No. 62/066,280, filed on Oct. 20, 2014, provisional application No. 62/100,844, filed on Jan. 7, 2015.

(51) Int. Cl.
| | |
|---|---|
| *A61K 9/00* | (2006.01) |
| *A61K 31/439* | (2006.01) |
| *A61K 31/4439* | (2006.01) |
| *A61K 31/4427* | (2006.01) |
| *A61K 31/4985* | (2006.01) |
| *A61K 45/06* | (2006.01) |
| *A61K 31/4995* | (2006.01) |

(52) U.S. Cl.
CPC ............ *A61K 9/0043* (2013.01); *A61K 9/007* (2013.01); *A61K 31/439* (2013.01); *A61K 31/4427* (2013.01); *A61K 31/4439* (2013.01); *A61K 31/4985* (2013.01); *A61K 31/4995* (2013.01); *A61K 45/06* (2013.01)

(58) Field of Classification Search
USPC ........................................................ 424/400
See application file for complete search history.

(56) References Cited

U.S. PATENT DOCUMENTS

| | | |
|---|---|---|
| 6,277,855 B1 | 8/2001 | Yerxa |
| 2006/0084656 A1 | 4/2006 | Ziegler et al. |
| 2011/0086086 A1 | 4/2011 | Johnson et al. |
| 2011/0274628 A1 | 11/2011 | Borschke |
| 2012/0289572 A1 | 11/2012 | Mazurov et al. |

FOREIGN PATENT DOCUMENTS

| | | |
|---|---|---|
| EP | 1214062 B1 | 11/2003 |
| WO | WO-03005998 A2 | 1/2003 |
| WO | WO-03045394 A1 | 6/2003 |
| WO | WO-2004039366 A1 | 5/2004 |
| WO | WO 2006/100075  * | 9/2006 |
| WO | WO-2008057938 A1 | 5/2008 |
| WO | WO-2009111550 A1 | 9/2009 |
| WO | WO-2010028011 A1 | 3/2010 |
| WO | WO-2010028033 A1 | 3/2010 |

OTHER PUBLICATIONS

Mazzanti (Int. J. Devi Neuroscience 25 (2007) 259-264).*
PCT/US2015/56273 International Search Report and Written Opinion dated Jan. 8, 2016.
Co-pending U.S. Appl. No. 14/887,243, filed Oct. 19, 2015.
Co-pending U.S. Appl. No. 14/887,248, filed Oct. 19, 2015.
Co-pending U.S. Appl. No. 14/887,253, filed Oct. 19, 2015.
U.S. Appl. No. 14/887,243 Office Action dated Mar. 24, 2016.
U.S. Appl. No. 14/887,248 Office Action dated Mar. 18, 2016.
U.S. Appl. No. 14/887,253 Office Action dated Mar. 23, 2016.
Albietz et al. Dry eye: an update on clinical diagnosis, management and promising new treatments. Clinical and Experimental Optometry 84(1):4-18 (2001).
Alimohammadi et al. Evidence for nicotinic acetylcholine receptors on nasal trigeminal nerve endings of the rat. Chem Senses 25:61-66 (2000).
Beule. Physiology and pathophysiology of respiratory mucosa of the nose and the paranasal sinuses. GMS Curr Top Otorhinolaryngol Head Neck Surg 9:1-24 (2010).
Thuerauf et al. Dose-dependent stereoselective activation of the trigeminal sensory system by nicotine in man. Psychopharmacology (Berl) 142(3):236-243 (1999).
U.S. Appl. No. 14/887,248 Office Action dated Jun. 28, 2016.

\* cited by examiner

*Primary Examiner* — Devang Thakor
(74) *Attorney, Agent, or Firm* — Wilson, Sonsini, Goodrich & Rosati

(57) ABSTRACT

Described herein are pharmaceutical formulations for treating ocular conditions.

13 Claims, 2 Drawing Sheets

PHARMACEUTICAL FORMULATIONS FOR TREATING OCULAR CONDITIONS

CROSS-REFERENCE

This application claims benefit of U.S. Provisional Application No. 62/066,280, filed on Oct. 20, 2014, and U.S. Provisional Application No. 62/100,844, filed on Jan. 7, 2015, both of which are herein incorporated by reference in their entirety.

BACKGROUND OF THE INVENTION

Dry Eye Disease ("DED") is a condition that affects millions of people worldwide. Approximately 40 million people in North America have some form of dry eye, and many millions more suffer worldwide. DED results from the disruption of the natural tear film on the surface of the eye, and can result in ocular discomfort, visual disturbance and a reduction in vision-related quality of life. Patients with severe cases of DED are at risk for serious ocular health deficiencies such as corneal ulceration, and can experience a quality of life deficiency comparable to that of moderate-severe angina.

SUMMARY OF THE INVENTION

Provided herein, in some embodiments, is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor. In some embodiments, is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of increasing tear production, comprising the local administration of a therapeutically effective amount of a nicotinic acetylcholine receptor agonist into the nasal cavity of an individual in need thereof, wherein the agonist selectively binds to at least one of the peripheral nicotinic acetylcholine receptor subtypes selected from alpha3beta4, alpha4beta2, and alpha7. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Provided herein, in some embodiments, is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of increasing tear production, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor. In some embodiments, is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of treating dry eye, comprising the local administration of a therapeutically effective amount of a nicotinic acetylcholine receptor agonist into the nasal cavity of an individual in need thereof, wherein the agonist selectively binds to at least one of the peripheral nicotinic acetylcholine receptor subtypes selected from alpha3beta4, alpha4beta2, and alpha7. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of treating dry eye, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor. In some embodiments, is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of improving ocular discomfort, comprising the local administration of a therapeutically effective amount of a nicotinic acetylcholine receptor agonist into the nasal cavity of an individual in need thereof, wherein the agonist selectively binds to at least one of the peripheral nicotinic acetylcholine receptor subtypes selected from alpha3beta4, alpha4beta2, and alpha7. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of improving ocular discomfort, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of improving ocular surface health, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of increasing mucin content on the ocular surface, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

Further provided herein, in some embodiments, is a method of increasing the amount or concentration of one or more lacrimal proteins on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of increasing the amount or concentration of one or more lacrimal proteins on the ocular surface, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of increasing the amount or concentration of one or more lacrimal proteins on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing the amount or concentration of one or more lacrimal proteins on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing the amount or concentration of one or more lacrimal proteins on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments the lacrimal protein is epithelial growth factor, lactoferin, lacritin, prolactin, adrenocorticotropic, leucine enkephalin, ALS2CL, ARHGEF19, KIAA1109, PLXNA1, POLG, WIPI1, ZMIZ2 or other proteins of the tear proteome.

Further provided herein, in some embodiments, is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is a method of enhancing tear clearance, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects.

In a further embodiment of any of the aforementioned embodiments, the method further comprises the local administration of one or more substances that prevent or facilitate the recovery of the nicotinic acetylcholine receptor from the desensitized state. In a further embodiment of any of the aforementioned embodiments, the method further comprises the local administration of one or more substances that prevent the entry or reduce the entry of the nicotinic acetylcholine receptor into the desensitized state, or facilitate the recovery of the nicotinic acetylcholine receptor from the desensitized state. In some embodiments, the one or more substances are selected from protein kinase C (PKC) or factors that upregulate or up-modulate PKC, cAMP-dependent protein kinase (PKA) or factors that upregulate or up-modulate PKA, and calcineurin inhibitors. In some embodiments, the calcineurin inhibitor is selected from cyclosporine, pimecrolimus, and tacrolimus.

In a further embodiment of any of the aforementioned embodiments, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380.

In a further embodiment of any of the aforementioned embodiments, the nicotinic acetylcholine receptor agonist is selected from a compound disclosed in WO 2008/057938, WO 2009/111550, WO 2010/028011, or WO 2010/028033, each of which is incorporated herein by reference.

In a further embodiment of any of the aforementioned embodiments, at least 1 microgram of the nicotinic acetylcholine receptor agonist is administered into the nasal cavity. In a further embodiment of any of the aforementioned embodiments, at least 5 micrograms of the nicotinic acetylcholine receptor agonist is administered into the nasal cavity. In a further embodiment of any of the aforementioned embodiments, at least 10 micrograms of the nicotinic acetylcholine receptor agonist is administered into the nasal cavity. In another embodiment of any of the aforementioned embodiments, at least 25 micrograms of the nicotinic acetylcholine receptor agonist is administered into the nasal cavity. In another embodiment of any of the aforementioned embodiments, at least 50 micrograms of the nicotinic acetylcholine receptor agonist is administered into the nasal cavity. In another embodiment of any of the aforementioned embodiments, at least 100 micrograms of the nicotinic acetylcholine receptor agonist is administered into the nasal cavity. In another embodiment of any of the aforementioned embodiments, at least 250 micrograms of the nicotinic acetylcholine receptor agonist is administered into the nasal cavity. In another embodiment of any of the aforementioned embodiments, at least 500 micrograms of the nicotinic acetylcholine receptor agonist is administered into the nasal cavity.

In a further embodiment of any of the aforementioned embodiments, the nicotinic acetylcholine receptor agonist is administered at least once daily. In another embodiment of any of the aforementioned embodiments, the nicotinic acetylcholine receptor agonist is administered at least twice daily. In another embodiment of any of the aforementioned embodiments, the nicotinic acetylcholine receptor agonist is administered for at least two days.

In a further embodiment of any of the aforementioned embodiments, the nicotinic acetylcholine receptor agonist is administered as needed. In another embodiment of any of the aforementioned embodiments, the nicotinic acetylcholine receptor agonist is administered as needed in response to symptoms. In another embodiment of any of the aforementioned embodiments, the timing or frequency of administration of the nicotinic acetylcholine receptor agonist is designed or adjusted to prevent desensitization of the nicotinic acetylcholine receptors.

In a further embodiment of any of the aforementioned embodiments, the nicotinic acetylcholine receptor agonist is administered into the nasal cavity as a liquid, suspension, aerosol, gel, ointment, dry powder, cream, paste, lotion, or balm. In a further embodiment of any of the aforementioned embodiments, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid.

In a further embodiment of any of the aforementioned embodiments, the trigeminal nerve is activated. In a further embodiment, the anterior ethmoidal nerve is activated.

In a further embodiment of any of the aforementioned embodiments, the nasolacrimal reflex is activated.

Further provided herein, in some embodiments, is a pharmaceutical formulation for local administration in the nasal cavity of an individual comprising a nicotinic acetylcholine receptor agonist formulated to prevent desensitization and in a dosage amount that is not systemically bioavailable. In some embodiments is a pharmaceutical formulation for local administration in the nasal cavity of an individual comprising a nicotinic acetylcholine receptor agonist formulated to prevent desensitization and in a dosage amount that does not result in undesired psychoactive side effects. In some embodiments is a pharmaceutical formulation for local administration in the nasal cavity of an individual comprising a nicotinic acetylcholine receptor agonist formulated to prevent desensitization and in a dosage amount that does not result in undesired systemic side effects. In some embodiments, the pharmaceutical formulation further comprises one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments, the calcineurin inhibitor is selected from cyclosporine, pimecrolimus, and tacrolimus. In some embodiments, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In some embodiments, the nicotinic acetylcholine receptor agonist is selected from a compound disclosed in WO 2008/057938, WO 2009/111550, WO 2010/028011, or WO 2010/028033. In some embodiments, the nicotinic acetylcholine receptor agonist selectively binds to at least one of the peripheral nicotinic acetylcholine receptor subtypes selected from alpha3beta4, alpha4beta2, and alpha7. In some embodiments, the pharmaceutical formulation comprises about 1 mg/mL of the nicotinic acetylcholine receptor agonist. In some embodiments, the pharmaceutical formulation comprises about 10 mg/mL of the nicotinic acetylcholine receptor agonist. In some embodiments, the pharmaceutical formulation comprises at least 1 microgram of the nicotinic acetylcholine receptor agonist per dose. In some embodiments, the pharmaceutical formulation comprises at least 5 micrograms of the nicotinic acetylcholine receptor agonist per dose. In some embodiments, the pharmaceutical formulation comprises at least 10 micrograms of the nicotinic acetylcholine receptor agonist per dose. In some embodiments, the pharmaceutical formulation comprises at least 25 micrograms of the nicotinic acetylcholine receptor agonist per dose. In some embodiments, the pharmaceutical formulation comprises at least 50 micrograms of the nicotinic acetylcholine receptor agonist per dose. In some embodiments, the pharmaceutical formulation comprises at least 100 micrograms of the nicotinic acetylcholine receptor agonist per dose. In some embodiments, the pharmaceutical formulation comprises at least 250 micrograms of the nicotinic acetylcholine receptor agonist per dose. In some embodiments, the pharmaceutical formulation comprises at least 500 micrograms of the nicotinic acetylcholine receptor agonist per dose. In some embodiments, the pharmaceutical formulation comprises between 5 micrograms and 1 gram of the nicotinic acetylcholine receptor agonist per dose. In some embodiments, the pharmaceutical formulation is administered at least once daily. In some embodiments, the pharmaceutical formulation is administered at least twice daily. In some embodiments, the pharmaceutical formulation is administered for at least two days. In some embodiments, the pharmaceutical formulation is administered into the nasal cavity as a liquid, suspension, aerosol, gel, ointment, dry powder, cream, paste, lotion, or balm. In some embodiments, the pharmaceutical formulation is administered into the nasal cavity by a syringe, dropper, bottle nebulizer, atomization pump, inhaler, powder spray device, vaporizer, patch, medicated stick, pipette, or jet of liquid.

DETAILED DESCRIPTION OF THE INVENTION

Figure 1:
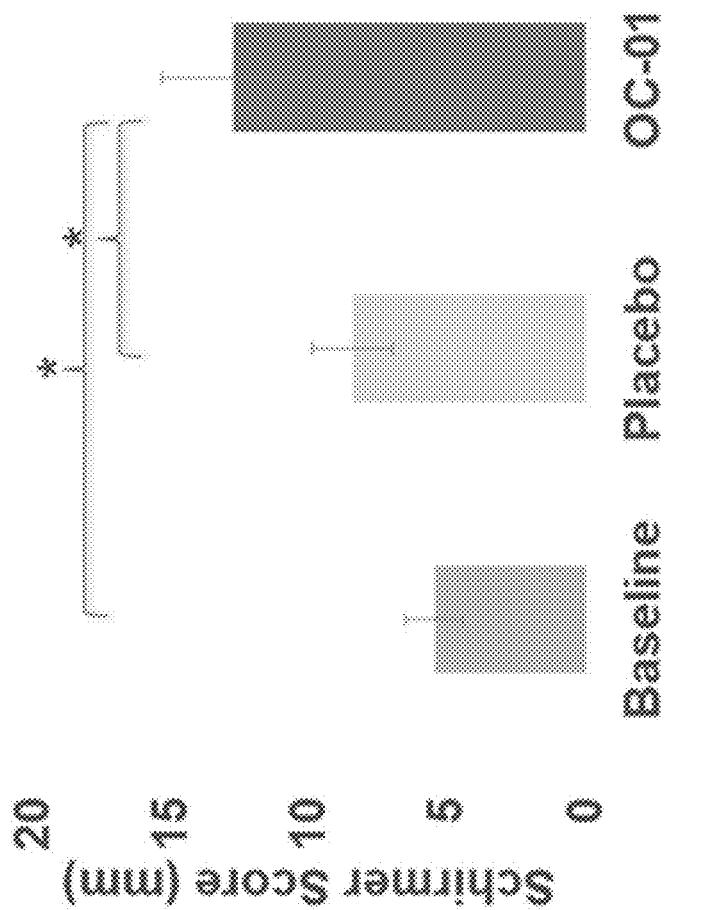
FIG. 1 shows tear production in patients receiving OC-01 compared to baseline and placebo.

The etiology of DED is becoming increasingly well understood. DED is progressive in nature, and fundamentally results from insufficient tear coverage on the surface of the eye. This poor tear coverage prevents healthy gas exchange and nutrient transport for the ocular surface, promotes cellular desiccation and creates a poor refractive surface for vision. Poor tear coverage typically results from: 1) insufficient aqueous tear production from the lacrimal glands (e.g. secondary to post-menopausal hormonal deficiency, auto-immune disease, LASIK surgery, etc.), and/or 2) excessive evaporation of aqueous tear resulting from dysfunction of the meibomian glands. Low tear volume causes a hyperosmolar environment that induces an inflamed state of the ocular surface. This inflammatory response induces apoptosis of the surface cells which in turn prevents proper distribution of the tear film on the ocular surface so that any given tear volume is rendered less effective. This initiates a vicious cycle where more inflammation can ensue causing more surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease (fewer tears cause nerve cell loss, which results in fewer tears, etc.).

There is a wide spectrum of treatments for DED, however, none provides substantial efficacy for treatment of the condition. Treatment options include: artificial tear substitutes, ointments, gels, warm compresses, environmental modification, topical cyclosporine, omega-3 fatty acid supplements, punctal plugs and moisture chamber goggles. Patients with severe disease may further be treated with punctal cautery, systemic cholinergic agonists, systemic anti-inflammatory agents, mucolytic agents, autologous serum tears, PROSE scleral contact lenses and tarsorrhaphy. Despite these treatment options, DED continues to be considered one of the most poorly treated diseases in ophthalmology. Accordingly, it would be desirable to have a more effective treatment for dry eye.

Nicotinic acetylcholine receptors are cholinergic receptors found in the central nervous system (CNS), peripheral nervous systems (PNS) and skeletal muscles. These receptors are ligand-gated ion channels with binding sites for acetylcholine and other molecules. When a nicotinic acetylcholine receptor agonist binds to the receptor, it stabilizes the open state of the ion channel allowing influx of cations such as potassium, calcium and sodium ions.

Acting on the central nervous system, systemic nicotinic acetylcholine receptor agonists agonist are gaining attention as drug candidates for multiple disorders such as Alzheimer's disease, Parkinson's disease, schizophrenia, attention-deficit hyperactivity disorder (ADHD), and nicotine addiction. However, systemic exposure of these central nervous system agents has been associated with a variety of undesired psychoactive side effects including anxiety, depression, and irritability.

Described herein are methods of treating ocular conditions and/or improving ocular surface health comprising the local administration of a therapeutically effective amount of a nicotinic acetylcholine receptor agonist into the nasal cavity of an individual in need thereof, wherein the agonist selectively binds to the peripheral nicotinic acetylcholine receptor. In some embodiments the nicotinic acetylcholine receptor agonist binds to the peripheral nicotinic acetylcholine receptor and does not cross the blood-brain barrier in a pharmacologically relevant concentration. In some embodiments the nicotinic acetylcholine receptor agonist binds to the peripheral nicotinic acetylcholine receptor and does not cross the blood-brain barrier in a pharmacologically relevant concentration and is administered in an amount that is not systemically bioavailable. In some embodiments the nicotinic acetylcholine receptor agonist binds to the peripheral nicotinic acetylcholine receptor and does not cross the blood-brain barrier in a pharmacologically relevant concentration and is administered in an amount that does not result in undesired psychoactive side effects. In some embodiments the nicotinic acetylcholine receptor agonist binds to the peripheral nicotinic acetylcholine receptor and does not cross the blood-brain barrier in a pharmacologically relevant concentration and is administered in an amount that does not result in undesired systemic side effects.

Prolonged or repeat exposure to a stimulus often results in decreased responsiveness of that receptor toward a stimulus, termed desensitization. It has been reported that, after prolonged nicotinic acetylcholine receptor exposure to an agonist, the agonist itself causes an agonist-induced conformational change in the receptor, resulting in receptor desensitization.

Described herein are methods of treating ocular conditions and/or improving ocular surface health comprising the local administration of a therapeutically effective amount of a nicotinic acetylcholine receptor agonist into the nasal cavity of an individual in need thereof, wherein the agonist selectively binds to the peripheral nicotinic acetylcholine receptor, further comprising the local administration of one or more substances that prevent or facilitate the recovery of the nicotinic acetylcholine receptor from the desensitized state. Also described herein are methods of treating ocular conditions and/or improving ocular surface health comprising the local administration of a therapeutically effective amount of a nicotinic acetylcholine receptor agonist into the nasal cavity of an individual in need thereof, wherein the agonist selectively binds to the peripheral nicotinic acetylcholine receptor, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments, the one or more substances that prevent or facilitate the recovery of the nicotinic acetylcholine receptor from the desensitized state are selected from protein kinase C (PKC) or factors that upregulate or up-modulate PKC, cAMP-dependent protein kinase (PKA) or factors that upregulate or up-modulate PKA, and calcineurin inhibitors.

Further described herein are pharmaceutical formulations for local administration into the nasal cavity of an individual comprising a nicotinic acetylcholine receptor agonist formulated to prevent desensitization. Also described herein are pharmaceutical formulations for local administration into the nasal cavity of an individual, further comprising one or more substances that prevent or facilitate the recovery of the nicotinic acetylcholine receptor from the desensitized state. Also described herein are pharmaceutical formulations for local administration into the nasal cavity of an individual, further comprising one or more substances that prevent the entry or reduce the entry of the nicotinic acetylcholine receptor into the desensitized state, or facilitate the recovery of the nicotinic acetylcholine receptor from the desensitized state. Also described herein are pharmaceutical formulations for local administration into the nasal cavity of an individual, further comprising one or more substances that prevent or facilitate the recovery of the nicotinic acetylcholine receptor from the desensitized state, wherein the one or more substances are selected from protein kinase C (PKC) or factors that upregulate or up-modulate PKC, cAMP-dependent protein kinase (PKA) or factors that upregulate or up-modulate PKA, and calcineurin inhibitors. Also described herein are pharmaceutical formulations for local administration into the nasal cavity of an individual, further comprising one or more substances that prevent the entry or reduce the entry of the nicotinic acetylcholine receptor into the desensitized state, or facilitate the recovery of the nicotinic acetylcholine receptor from the desensitized state, wherein the one or more substances are selected from protein kinase C (PKC) or factors that upregulate or up-modulate PKC, cAMP-dependent protein kinase (PKA) or factors that upregulate or up-modulate PKA, and calcineurin inhibitors.

Increased Tear Production

Provided herein, in some embodiments, is a method of increasing tear production in a subject. In some embodiments, is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of increasing tear production, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of increasing tear production, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of increasing tear production, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of increasing tear production, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing tear production, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of increasing tear production, further comprising the local administration of one or more substances that prevent or facilitate the recovery of the nicotinic acetylcholine receptor from the desensitized state. In some embodiments is a method of increasing tear production, further comprising the local administration of one or more substances that prevent the entry or reduce the entry of the nicotinic acetylcholine receptor into the desensitized state, or facilitate the recovery of the nicotinic acetylcholine receptor from the desensitized state.

In some embodiments is a method of increasing tear production, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing tear production, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing tear production, further comprising the local administration of protein kinase C (PKC) or factors that upregulate or up-modulate PKC. In some embodiments is a method of increasing tear production, further comprising the local administration of cAMP-dependent protein kinase (PKA) or factors that upregulate or up-modulate PKA. In some embodiments is a method of increasing tear production, further comprising the local administration of a calcineurin inhibitor. In some embodiments is a method of increasing tear production, further comprising the local administration of a calcineurin inhibitor, wherein the calcineurin inhibitor is selected from cyclosporine, pimecrolimus, and tacrolimus. In some embodiments is a method of increasing tear production, further comprising the local administration of cyclosporine. In some embodiments is a method of increasing tear production, further comprising the local administration of pimecrolimus. In some embodiments is a method of increasing tear production, further comprising the local administration of tacrolimus.

In a further embodiment of any of the aforementioned embodiments of increasing tear production, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of increasing tear production, the nicotinic acetylcholine receptor agonist is nicotine. In another embodiment of any of the aforementioned embodiments of increasing tear production, the nicotinic acetylcholine receptor agonist is cytisine. In another embodiment of any of the aforementioned embodiments of increasing tear production, the nicotinic acetylcholine receptor agonist is epibatidine. In another embodiment of any of the aforementioned embodiments of increasing tear production, the nicotinic acetylcholine receptor agonist is varenicline. In another embodiment of any of the aforementioned embodiments of increasing tear production, the nicotinic acetylcholine receptor agonist is tebanicline. In another embodiment of any of the aforementioned embodiments of increasing tear production, the nicotinic acetylcholine receptor agonist is DBO-83. In another embodiment of any of the aforementioned embodiments of increasing tear production, the nicotinic acetylcholine receptor agonist is CC4. In another embodiment of any of the aforementioned embodiments of increasing tear production, the nicotinic acetylcholine receptor agonist is ABT-418. In another embodiment of any of the aforementioned embodiments of increasing tear production, the nicotinic acetylcholine receptor agonist is ABT-366833. In another embodiment of any of the aforementioned embodiments of increasing tear production, the nicotinic acetylcholine receptor agonist is ABT-202. In another embodiment of any of the aforementioned embodiments of increasing tear production, the nicotinic acetylcholine receptor agonist is ABT-894. In another embodiment of any of the aforementioned embodiments of increasing tear production, the nicotinic acetylcholine receptor agonist is SIB-1663. In another embodiment of any of the aforementioned embodiments of increasing tear production, the nicotinic acetylcholine receptor agonist is GTS-21. In another embodiment of any of the aforementioned embodiments of increasing tear production, the nicotinic acetylcholine receptor agonist is PHA-543613. In another embodiment of any of the aforementioned embodiments of increasing tear production, the nicotinic acetylcholine receptor agonist is PNU-282987. In another embodiment of any of the aforementioned embodiments of increasing tear production, the nicotinic acetylcholine receptor agonist is LY-2087101. In another embodiment of any of the aforementioned embodiments of increasing tear production, the nicotinic acetylcholine receptor agonist is A85380. In another embodiment of any of the aforementioned embodiments of increasing tear production, the nicotinic acetylcholine receptor agonist is 5-I-A85380.

In a further embodiment of any of the aforementioned embodiments of increasing tear production, the nicotinic acetylcholine receptor agonist is selected from a compound disclosed in WO 2008/057938, WO 2009/111550, WO 2010/028011, or WO 2010/028033.

In another embodiment of any of the aforementioned embodiments of increasing tear production, at least 1 microgram of the nicotinic acetylcholine receptor agonist is administered into the nasal cavity. In another embodiment of any of the aforementioned embodiments of increasing tear production, at least 5 micrograms of the nicotinic acetylcholine receptor agonist is administered into the nasal cavity. In another embodiment of any of the aforementioned embodiments of increasing tear production, at least 10 micrograms of the nicotinic acetylcholine receptor agonist is administered into the nasal cavity. In another embodiment of any of the aforementioned embodiments of increasing tear production, at least 25 micrograms of the nicotinic acetylcholine receptor agonist is administered into the nasal cavity. In another embodiment of any of the aforementioned embodiments of increasing tear production, at least 50 micrograms of the nicotinic acetylcholine receptor agonist is administered into the nasal cavity. In another embodiment of any of the aforementioned embodiments of increasing tear production, at least 100 micrograms of the nicotinic acetylcholine receptor agonist is administered into the nasal cavity. In another embodiment of any of the aforementioned embodiments of increasing tear production, at least 250 micrograms of the nicotinic acetylcholine receptor agonist is administered into the nasal cavity. In another embodiment of any of the aforementioned embodiments of increasing tear production, at least 500 micrograms of the nicotinic acetylcholine receptor agonist is administered into the nasal cavity. In another embodiment of any of the aforementioned embodiments of increasing tear production, at least 750 micrograms of the nicotinic acetylcholine receptor agonist is administered into the nasal cavity. In another embodiment of any of the aforementioned embodiments of increasing tear production, at least 1000 micrograms of the nicotinic acetylcholine receptor agonist is administered into the nasal cavity. In another embodiment of any of the aforementioned embodiments of increasing tear production, between 1 microgram and 1000 micrograms of the nicotinic acetylcholine receptor agonist is administered into the nasal cavity. In another embodiment of any of the aforementioned embodiments of increasing tear production, between 5 micrograms and 1000 micrograms of the nicotinic acetylcholine receptor agonist is administered into the nasal cavity. In another embodiment of any of the aforementioned embodiments of increasing tear production, between 5 micrograms and 100 micrograms of the nicotinic acetylcholine receptor agonist is administered into the nasal cavity. In another embodiment of any of the aforementioned embodiments of increasing tear production, between 5 micrograms and 50 micrograms of the nicotinic acetylcholine receptor agonist is administered into the nasal cavity. In another embodiment of any of the aforementioned embodiments of increasing tear production, between 10 micrograms and 50 micrograms of the nicotinic acetylcholine receptor agonist is administered into the nasal cavity. In another embodiment of any of the aforementioned embodiments of increasing tear production, between 25 micrograms and 1000 micrograms of the nicotinic acetylcholine receptor agonist is administered into the nasal cavity. In another embodiment of any of the aforementioned embodiments of increasing tear production, between 50 micrograms and 1000 micrograms of the nicotinic acetylcholine receptor agonist is administered into the nasal cavity. In another embodiment of any of the aforementioned embodiments of increasing tear production, between 100 micrograms and 1000 micrograms of the nicotinic acetylcholine receptor agonist is administered into the nasal cavity. In another embodiment of any of the aforementioned embodiments of increasing tear production, between 100 micrograms and 750 micrograms of the nicotinic acetylcholine receptor agonist is administered into the nasal cavity. In another embodiment of any of the aforementioned embodiments of increasing tear production, between 150 micrograms and 750 micrograms of the nicotinic acetylcholine receptor agonist is administered into the nasal cavity. In another embodiment of any of the aforementioned embodiments of increasing tear production, between 150 micrograms and 600 micrograms of the nicotinic acetylcholine receptor agonist is administered into the nasal cavity.

In another embodiment of any of the aforementioned embodiments of increasing tear production, the nicotinic acetylcholine receptor agonist is administered once daily. In another embodiment of any of the aforementioned embodiments of increasing tear production, the nicotinic acetylcholine receptor agonist is administered at least once daily. In another embodiment of any of the aforementioned embodiments of increasing tear production, the nicotinic acetylcholine receptor agonist is administered twice daily. In another embodiment of any of the aforementioned embodiments of increasing tear production, the nicotinic acetylcholine receptor agonist is administered at least twice daily. In another embodiment of any of the aforementioned embodiments of increasing tear production, the nicotinic acetylcholine receptor agonist is administered three times daily. In another embodiment of any of the aforementioned embodiments of increasing tear production, the nicotinic acetylcholine receptor agonist is administered at least three times daily. In another embodiment of any of the aforementioned embodiments of increasing tear production, the nicotinic acetylcholine receptor agonist is administered for one day. In another embodiment of any of the aforementioned embodiments of increasing tear production, the nicotinic acetylcholine receptor agonist is administered for at least two days. In another embodiment of any of the aforementioned embodiments of increasing tear production, the nicotinic acetylcholine receptor agonist is administered for at least three days. In another embodiment of any of the aforementioned embodiments of increasing tear production, the nicotinic acetylcholine receptor agonist is administered for at least four days. In another embodiment of any of the aforementioned embodiments of increasing tear production, the nicotinic acetylcholine receptor agonist is administered for at least five days. In another embodiment of any of the aforementioned embodiments of increasing tear production, the nicotinic acetylcholine receptor agonist is administered for at least seven days. In another embodiment of any of the aforementioned embodiments of increasing tear production, the nicotinic acetylcholine receptor agonist is administered for at least ten days. In another embodiment of any of the aforementioned embodiments of increasing tear production, the nicotinic acetylcholine receptor agonist is administered for at least fourteen days. In another embodiment of any of the aforementioned embodiments of increasing tear production, the nicotinic acetylcholine receptor agonist is administered for at least twenty one days. In another embodiment of any of the aforementioned embodiments of increasing tear production, the nicotinic acetylcholine receptor agonist is administered for at least thirty days.

In another embodiment of any of the aforementioned embodiments of increasing tear production, the nicotinic acetylcholine receptor agonist is administered in alternating nostrils.

In another embodiment of any of the aforementioned embodiments of increasing tear production, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of increasing tear production, the nicotinic acetylcholine receptor agonist is administered into the nasal cavity as a liquid. In another embodiment of any of the aforementioned embodiments of increasing tear production, the nicotinic acetylcholine receptor agonist is administered into the nasal cavity as a suspension. In another embodiment of any of the aforementioned embodiments of increasing tear production, the nicotinic acetylcholine receptor agonist is administered into the nasal cavity as an aerosol. In another embodiment of any of the aforementioned embodiments of increasing tear production, the nicotinic acetylcholine receptor agonist is administered into the nasal cavity as a gel. In another embodiment of any of the aforementioned embodiments of increasing tear production, the nicotinic acetylcholine receptor agonist is administered into the nasal cavity as an ointment. In another embodiment of any of the aforementioned embodiments of increasing tear production, the nicotinic acetylcholine receptor agonist is administered into the nasal cavity as a dry powder. In another embodiment of any of the aforementioned embodiments of increasing tear production, the nicotinic acetylcholine receptor agonist is administered into the nasal cavity as a cream. In another embodiment of any of the aforementioned embodiments of increasing tear production, the nicotinic acetylcholine receptor agonist is administered into the nasal cavity as a paste. In another embodiment of any of the aforementioned embodiments of increasing tear production, the nicotinic acetylcholine receptor agonist is administered into the nasal cavity as a lotion. In another embodiment of any of the aforementioned embodiments of increasing tear production, the nicotinic acetylcholine receptor agonist is administered into the nasal cavity as a balm.

In another embodiment of any of the aforementioned embodiments of increasing tear production, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of increasing tear production, the nicotinic acetylcholine receptor agonist is administered into the nasal cavity by a syringe. In another embodiment of any of the aforementioned embodiments of increasing tear production, the nicotinic acetylcholine receptor agonist is administered into the nasal cavity by a dropper. In another embodiment of any of the aforementioned embodiments of increasing tear production, the nicotinic acetylcholine receptor agonist is administered into the nasal cavity by a bottle nebulizer. In another embodiment of any of the aforementioned embodiments of increasing tear production, the nicotinic acetylcholine receptor agonist is administered into the nasal cavity by an atomization pump. In another embodiment of any of the aforementioned embodiments of increasing tear production, the nicotinic acetylcholine receptor agonist is administered into the nasal cavity by an inhaler. In another embodiment of any of the aforementioned embodiments of increasing tear production, the nicotinic acetylcholine receptor agonist is administered into the nasal cavity by a powder spray device. In another embodiment of any of the aforementioned embodiments of increasing tear production, the nicotinic acetylcholine receptor agonist is administered into the nasal cavity by a vaporizer. In another embodiment of any of the aforementioned embodiments of increasing tear production, the nicotinic acetylcholine receptor agonist is administered into the nasal cavity by a patch. In another embodiment of any of the aforementioned embodiments of increasing tear production, the nicotinic acetylcholine receptor agonist is administered into the nasal cavity by a medicated stick. In another embodiment of any of the aforementioned embodiments of increasing tear production, the nicotinic acetylcholine receptor agonist is administered into the nasal cavity by a pipette. In another embodiment of any of the aforementioned embodiments of increasing tear production, the nicotinic acetylcholine receptor agonist is administered into the nasal cavity by a jet of liquid.

In another embodiment of any of the aforementioned embodiments of increasing tear production, the trigeminal nerve is activated. In a further embodiment of increasing tear production, the anterior ethmoidal nerve is activated. In another embodiment of any of the aforementioned embodiments of increasing tear production, the nasolacrimal reflex is activated.

Treating Dry Eye

Provided herein, in some embodiments, is a method of treating dry eye in a subject. In some embodiments, is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of treating dry eye, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of treating dry eye, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of treating dry eye, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of treating dry eye, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of treating dry eye, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of treating dry eye, further comprising the local administration of one or more substances that prevent or facilitate the recovery of the nicotinic acetylcholine receptor from the desensitized state. In some embodiments is a method of treating dry eye, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of treating dry eye, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of treating dry eye, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of treating dry eye, further comprising the local administration of protein kinase C (PKC) or factors that upregulate or up-modulate PKC. In some embodiments is a method of treating dry eye, further comprising the local administration of cAMP-dependent protein kinase (PKA) or factors that upregulate or up-modulate PKA. In some embodiments is a method of treating dry eye, further comprising the local administration of a calcineurin inhibitor. In some embodiments is a method of treating dry eye, further comprising the local administration of a calcineurin inhibitor, wherein the calcineurin inhibitor is selected from cyclosporine, pimecrolimus, and tacrolimus. In some embodiments is a method of treating dry eye, further comprising the local administration of cyclosporine. In some embodiments is a method of treating dry eye, further comprising the local administration of pimecrolimus. In some embodiments is a method of treating dry eye, further comprising the local administration of tacrolimus.

In a further embodiment of any of the aforementioned embodiments of treating dry eye, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of treating dry eye, the nicotinic acetylcholine receptor agonist is nicotine. In another embodiment of any of the aforementioned embodiments of treating dry eye, the nicotinic acetylcholine receptor agonist is cytisine. In another embodiment of any of the aforementioned embodiments of treating dry eye, the nicotinic acetylcholine receptor agonist is epibatidine. In another embodiment of any of the aforementioned embodiments of treating dry eye, the nicotinic acetylcholine receptor agonist is varenicline. In another embodiment of any of the aforementioned embodiments of treating dry eye, the nicotinic acetylcholine receptor agonist is tebanicline. In another embodiment of any of the aforementioned embodiments of treating dry eye, the nicotinic acetylcholine receptor agonist is DBO-83. In another embodiment of any of the aforementioned embodiments of treating dry eye, the nicotinic acetylcholine receptor agonist is CC4. In another embodiment of any of the aforementioned embodiments of treating dry eye, the nicotinic acetylcholine receptor agonist is ABT-418. In another embodiment of any of the aforementioned embodiments of treating dry eye, the nicotinic acetylcholine receptor agonist is ABT-366833. In another embodiment of any of the aforementioned embodiments of treating dry eye, the nicotinic acetylcholine receptor agonist is ABT-202. In another embodiment of any of the aforementioned embodiments of treating dry eye, the nicotinic acetylcholine receptor agonist is ABT-894. In another embodiment of any of the aforementioned embodiments of treating dry eye, the nicotinic acetylcholine receptor agonist is SIB-1663. In another embodiment of any of the aforementioned embodiments of treating dry eye, the nicotinic acetylcholine receptor agonist is GTS-21. In another embodiment of any of the aforementioned embodiments of treating dry eye, the nicotinic acetylcholine receptor agonist is PHA-543613. In another embodiment of any of the aforementioned embodiments of treating dry eye, the nicotinic acetylcholine receptor agonist is PNU-282987. In another embodiment of any of the aforementioned embodiments of treating dry eye, the nicotinic acetylcholine receptor agonist is LY-2087101. In another embodiment of any of the aforementioned embodiments of treating dry eye, the nicotinic acetylcholine receptor agonist is A85380. In another embodiment of any of the aforementioned embodiments of treating dry eye, the nicotinic acetylcholine receptor agonist is 5-I-A85380.

In a further embodiment of any of the aforementioned embodiments of treating dry eye, the nicotinic acetylcholine receptor agonist is selected from a compound disclosed in WO 2008/057938, WO 2009/111550, WO 2010/028011, or WO 2010/028033.

In another embodiment of any of the aforementioned embodiments of treating dry eye, at least 1 microgram of the nicotinic acetylcholine receptor agonist is administered into the nasal cavity. In another embodiment of any of the aforementioned embodiments of treating dry eye, at least 5 micrograms of the nicotinic acetylcholine receptor agonist is administered into the nasal cavity. In another embodiment of any of the aforementioned embodiments of treating dry eye, at least 10 micrograms of the nicotinic acetylcholine receptor agonist is administered into the nasal cavity. In another embodiment of any of the aforementioned embodiments of treating dry eye, at least 25 micrograms of the nicotinic acetylcholine receptor agonist is administered into the nasal cavity. In another embodiment of any of the aforementioned embodiments of treating dry eye, at least 50 micrograms of the nicotinic acetylcholine receptor agonist is administered into the nasal cavity. In another embodiment of any of the aforementioned embodiments of treating dry eye, at least 100 micrograms of the nicotinic acetylcholine receptor agonist is administered into the nasal cavity. In another embodiment of any of the aforementioned embodiments of treating dry eye, at least 250 micrograms of the nicotinic acetylcholine receptor agonist is administered into the nasal cavity. In another embodiment of any of the aforementioned embodiments of treating dry eye, at least 500 micrograms of the nicotinic acetylcholine receptor agonist is administered into the nasal cavity. In another embodiment of any of the aforementioned embodiments of treating dry eye, at least 750 micrograms of the nicotinic acetylcholine receptor agonist is administered into the nasal cavity. In another embodiment of any of the aforementioned embodiments of treating dry eye, at least 1000 micrograms of the nicotinic acetylcholine receptor agonist is administered into the nasal cavity. In another embodiment of any of the aforementioned embodiments of treating dry eye, between 1 microgram and 1000 micrograms of the nicotinic acetylcholine receptor agonist is administered into the nasal cavity. In another embodiment of any of the aforementioned embodiments of treating dry eye, between 5 micrograms and 1000 micrograms of the nicotinic acetylcholine receptor agonist is administered into the nasal cavity. In another embodiment of any of the aforementioned embodiments of treating dry eye, between 5 micrograms and 100 micrograms of the nicotinic acetylcholine receptor agonist is administered into the nasal cavity. In another embodiment of any of the aforementioned embodiments of treating dry eye, between 5 micrograms and 50 micrograms of the nicotinic acetylcholine receptor agonist is administered into the nasal cavity. In another embodiment of any of the aforementioned embodiments of treating dry eye, between 10 micrograms and 50 micrograms of the nicotinic acetylcholine receptor agonist is administered into the nasal cavity. In another embodiment of any of the aforementioned embodiments of treating dry eye, between 25 micrograms and 1000 micrograms of the nicotinic acetylcholine receptor agonist is administered into the nasal cavity. In another embodiment of any of the aforementioned embodiments of treating dry eye, between 50 micrograms and 1000 micrograms of the nicotinic acetylcholine receptor agonist is administered into the nasal cavity. In another embodiment of any of the aforementioned embodiments of treating dry eye, between 100 micrograms and 1000 micrograms of the nicotinic acetylcholine receptor agonist is administered into the nasal cavity. In another embodiment of any of the aforementioned embodiments of treating dry eye, between 100 micrograms and 750 micrograms of the nicotinic acetylcholine receptor agonist is administered into the nasal cavity. In another embodiment of any of the aforementioned embodiments of treating dry eye, between 150 micrograms and 750 micrograms of the nicotinic acetylcholine receptor agonist is administered into the nasal cavity. In another embodiment of any of the aforementioned embodiments of treating dry eye, between 150 micrograms and 600 micrograms of the nicotinic acetylcholine receptor agonist is administered into the nasal cavity.

In another embodiment of any of the aforementioned embodiments of treating dry eye, the nicotinic acetylcholine receptor agonist is administered once daily. In another embodiment of any of the aforementioned embodiments of treating dry eye, the nicotinic acetylcholine receptor agonist is administered at least once daily. In another embodiment of any of the aforementioned embodiments of treating dry eye, the nicotinic acetylcholine receptor agonist is administered twice daily. In another embodiment of any of the aforementioned embodiments of treating dry eye, the nicotinic acetylcholine receptor agonist is administered at least twice daily. In another embodiment of any of the aforementioned embodiments of treating dry eye, the nicotinic acetylcholine receptor agonist is administered three times daily. In another embodiment of any of the aforementioned embodiments of treating dry eye, the nicotinic acetylcholine receptor agonist is administered at least three times daily. In another embodiment of any of the aforementioned embodiments of treating dry eye, the nicotinic acetylcholine receptor agonist is administered for one day. In another embodiment of any of the aforementioned embodiments of treating dry eye, the nicotinic acetylcholine receptor agonist is administered for at least two days. In another embodiment of any of the aforementioned embodiments of treating dry eye, the nicotinic acetylcholine receptor agonist is administered for at least three days. In another embodiment of any of the aforementioned embodiments of treating dry eye, the nicotinic acetylcholine receptor agonist is administered for at least four days. In another embodiment of any of the aforementioned embodiments of treating dry eye, the nicotinic acetylcholine receptor agonist is administered for at least five days. In another embodiment of any of the aforementioned embodiments of treating dry eye, the nicotinic acetylcholine receptor agonist is administered for at least seven days. In another embodiment of any of the aforementioned embodiments of treating dry eye, the nicotinic acetylcholine receptor agonist is administered for at least ten days. In another embodiment of any of the aforementioned embodiments of treating dry eye, the nicotinic acetylcholine receptor agonist is administered for at least fourteen days. In another embodiment of any of the aforementioned embodiments of treating dry eye, the nicotinic acetylcholine receptor agonist is administered for at least twenty one days. In another embodiment of any of the aforementioned embodiments of treating dry eye, the nicotinic acetylcholine receptor agonist is administered for at least thirty days.

In another embodiment of any of the aforementioned embodiments of treating dry eye, the nicotinic acetylcholine receptor agonist is administered in alternating nostrils.

In another embodiment of any of the aforementioned embodiments of treating dry eye, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of treating dry eye, the nicotinic acetylcholine receptor agonist is administered into the nasal cavity as a liquid. In another embodiment of any of the aforementioned embodiments of treating dry eye, the nicotinic acetylcholine receptor agonist is administered into the nasal cavity as a suspension. In another embodiment of any of the aforementioned embodiments of treating dry eye, the nicotinic acetylcholine receptor agonist is administered into the nasal cavity as an aerosol. In another embodiment of any of the aforementioned embodiments of treating dry eye, the nicotinic acetylcholine receptor agonist is administered into the nasal cavity as a gel. In another embodiment of any of the aforementioned embodiments of treating dry eye, the nicotinic acetylcholine receptor agonist is administered into the nasal cavity as an ointment. In another embodiment of any of the aforementioned embodiments of treating dry eye, the nicotinic acetylcholine receptor agonist is administered into the nasal cavity as a dry powder. In another embodiment of any of the aforementioned embodiments of treating dry eye, the nicotinic acetylcholine receptor agonist is administered into the nasal cavity as a cream. In another embodiment of any of the aforementioned embodiments of treating dry eye, the nicotinic acetylcholine receptor agonist is administered into the nasal cavity as a paste. In another embodiment of any of the aforementioned embodiments of treating dry eye, the nicotinic acetylcholine receptor agonist is administered into the nasal cavity as a lotion. In another embodiment of any of the aforementioned embodiments of treating dry eye, the nicotinic acetylcholine receptor agonist is administered into the nasal cavity as a balm.

In another embodiment of any of the aforementioned embodiments of treating dry eye, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of treating dry eye, the nicotinic acetylcholine receptor agonist is administered into the nasal cavity by a syringe. In another embodiment of any of the aforementioned embodiments of treating dry eye, the nicotinic acetylcholine receptor agonist is administered into the nasal cavity by a dropper. In another embodiment of any of the aforementioned embodiments of treating dry eye, the nicotinic acetylcholine receptor agonist is administered into the nasal cavity by a bottle nebulizer. In another embodiment of any of the aforementioned embodiments of treating dry eye, the nicotinic acetylcholine receptor agonist is administered into the nasal cavity by an atomization pump. In another embodiment of any of the aforementioned embodiments of treating dry eye, the nicotinic acetylcholine receptor agonist is administered into the nasal cavity by an inhaler. In another embodiment of any of the aforementioned embodiments of treating dry eye, the nicotinic acetylcholine receptor agonist is administered into the nasal cavity by a powder spray device. In another embodiment of any of the aforementioned embodiments of treating dry eye, the nicotinic acetylcholine receptor agonist is administered into the nasal cavity by a vaporizer. In another embodiment of any of the aforementioned embodiments of treating dry eye, the nicotinic acetylcholine receptor agonist is administered into the nasal cavity by a patch. In another embodiment of any of the aforementioned embodiments of treating dry eye, the nicotinic acetylcholine receptor agonist is administered into the nasal cavity by a medicated stick. In another embodiment of any of the aforementioned embodiments of treating dry eye, the nicotinic acetylcholine receptor agonist is administered into the nasal cavity by a pipette. In another embodiment of any of the aforementioned embodiments of treating dry eye, the nicotinic acetylcholine receptor agonist is administered into the nasal cavity by a jet of liquid.

In another embodiment of any of the aforementioned embodiments of treating dry eye, the trigeminal nerve is activated. In a further embodiment of treating dry eye, the anterior ethmoidal nerve is activated. In another embodiment of any of the aforementioned embodiments of treating dry eye, the nasolacrimal reflex is activated.

Improved Ocular Discomfort

Provided herein, in some embodiments, is a method of improving ocular discomfort in a subject. In some embodiments, is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of improving ocular discomfort, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of improving ocular discomfort, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of improving ocular discomfort, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of improving ocular discomfort, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of improving ocular discomfort, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of improving ocular discomfort, further comprising the local administration of one or more substances that prevent or facilitate the recovery of the nicotinic acetylcholine receptor from the desensitized state. In some embodiments is a method of improving ocular discomfort, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of improving ocular discomfort, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular discomfort, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular discomfort, further comprising the local administration of protein kinase C (PKC) or factors that upregulate or up-modulate PKC. In some embodiments is a method of improving ocular discomfort, further comprising the local administration of cAMP-dependent protein kinase (PKA) or factors that upregulate or up-modulate PKA. In some embodiments is a method of improving ocular discomfort, further comprising the local administration of a calcineurin inhibitor. In some embodiments is a method of improving ocular discomfort, further comprising the local administration of a calcineurin inhibitor, wherein the calcineurin inhibitor is selected from cyclosporine, pimecrolimus, and tacrolimus. In some embodiments is a method of improving ocular discomfort, further comprising the local administration of cyclosporine. In some embodiments is a method of improving ocular discomfort, further comprising the local administration of pimecrolimus. In some embodiments is a method of improving ocular discomfort, further comprising the local administration of tacrolimus.

In a further embodiment of any of the aforementioned embodiments of improving ocular discomfort, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of improving ocular discomfort, the nicotinic acetylcholine receptor agonist is nicotine. In another embodiment of any of the aforementioned embodiments of improving ocular discomfort, the nicotinic acetylcholine receptor agonist is cytisine. In another embodiment of any of the aforementioned embodiments of improving ocular discomfort, the nicotinic acetylcholine receptor agonist is epibatidine. In another embodiment of any of the aforementioned embodiments of improving ocular discomfort, the nicotinic acetylcholine receptor agonist is varenicline. In another embodiment of the aforementioned embodiments of improving ocular discomfort, the nicotinic acetylcholine receptor agonist is tebanicline. In another embodiment of any of the aforementioned embodiments of improving ocular discomfort, the nicotinic acetylcholine receptor agonist is DBO-83. In another embodiment of any of the aforementioned embodiments of improving ocular discomfort, the nicotinic acetylcholine receptor agonist is CC4. In another embodiment of any of the aforementioned embodiments of improving ocular discomfort, the nicotinic acetylcholine receptor agonist is ABT-418. In another embodiment of any of the aforementioned embodiments of improving ocular discomfort, the nicotinic acetylcholine receptor agonist is ABT-366833. In another embodiment of any of the aforementioned embodiments of improving ocular discomfort, the nicotinic acetylcholine receptor agonist is ABT-202. In another embodiment of any of the aforementioned embodiments of improving ocular discomfort, the nicotinic acetylcholine receptor agonist is ABT-894. In another embodiment of any of the aforementioned embodiments of improving ocular discomfort, the nicotinic acetylcholine receptor agonist is SIB-1663. In another embodiment of any of the aforementioned embodiments of improving ocular discomfort, the nicotinic acetylcholine receptor agonist is GTS-21. In another embodiment of any of the aforementioned embodiments of improving ocular discomfort, the nicotinic acetylcholine receptor agonist is PHA-543613. In another embodiment of any of the aforementioned embodiments of improving ocular discomfort, the nicotinic acetylcholine receptor agonist is PNU-282987. In another embodiment of any of the aforementioned embodiments of improving ocular discomfort, the nicotinic acetylcholine receptor agonist is LY-2087101. In another embodiment of any of the aforementioned embodiments of improving ocular discomfort, the nicotinic acetylcholine receptor agonist is A85380. In another embodiment of any of the aforementioned embodiments of improving ocular discomfort, the nicotinic acetylcholine receptor agonist is 5-I-A85380.

In a further embodiment of any of the aforementioned embodiments of improving ocular discomfort, the nicotinic acetylcholine receptor agonist is selected from a compound disclosed in WO 2008/057938, WO 2009/111550, WO 2010/028011, or WO 2010/028033.

In another embodiment of any of the aforementioned embodiments of improving ocular discomfort, the ocular discomfort is associated with dry eye disease. In another embodiment of any of the aforementioned embodiments of improving ocular discomfort, the ocular discomfort is associated with the symptoms of dry eye disease. In another embodiment of any of the aforementioned embodiments of improving ocular discomfort, the ocular discomfort is associated with the symptoms of dry eye disease; wherein the symptoms are selected from itchiness, dryness, photophobia, blurriness, pain, sticky feeling, burning, stinging, and foreign body sensation.

In another embodiment of any of the aforementioned embodiments of improving ocular discomfort, the ocular discomfort is associated with blepharitis. In another embodiment of any of the aforementioned embodiments of improving ocular discomfort, the ocular discomfort is associated with meibomian gland dysfunction. In another embodiment of any of the aforementioned embodiments of improving ocular discomfort, the ocular discomfort is associated with allergic conjunctivitis. In another embodiment of any of the aforementioned embodiments of improving ocular discomfort, the ocular discomfort is associated with ocular surface toxicity and irritation. In another embodiment of any of the aforementioned embodiments of improving ocular discomfort, the ocular discomfort is associated with lacrimal drainage problems. In another embodiment of any of the aforementioned embodiments of improving ocular discomfort, the ocular discomfort is associated with eyelid disorders.

In another embodiment of any of the aforementioned embodiments of improving ocular discomfort, at least 1 microgram of the nicotinic acetylcholine receptor agonist is administered into the nasal cavity. In another embodiment of any of the aforementioned embodiments of improving ocular discomfort, at least 5 micrograms of the nicotinic acetylcholine receptor agonist is administered into the nasal cavity. In another embodiment of any of the aforementioned embodiments of improving ocular discomfort, at least 10 micrograms of the nicotinic acetylcholine receptor agonist is administered into the nasal cavity. In another embodiment of any of the aforementioned embodiments of improving ocular discomfort, at least 25 micrograms of the nicotinic acetylcholine receptor agonist is administered into the nasal cavity. In another embodiment of any of the aforementioned embodiments of improving ocular discomfort, at least 50 micrograms of the nicotinic acetylcholine receptor agonist is administered into the nasal cavity. In another embodiment of any of the aforementioned embodiments of improving ocular discomfort, at least 100 micrograms of the nicotinic acetylcholine receptor agonist is administered into the nasal cavity. In another embodiment of any of the aforementioned embodiments of improving ocular discomfort, at least 250 micrograms of the nicotinic acetylcholine receptor agonist is administered into the nasal cavity. In another embodiment of any of the aforementioned embodiments of improving ocular discomfort, at least 500 micrograms of the nicotinic acetylcholine receptor agonist is administered into the nasal cavity. In another embodiment of any of the aforementioned embodiments of improving ocular discomfort, at least 750 micrograms of the nicotinic acetylcholine receptor agonist is administered into the nasal cavity. In another embodiment of any of the aforementioned embodiments of improving ocular discomfort, at least 1000 micrograms of the nicotinic acetylcholine receptor agonist is administered into the nasal cavity. In another embodiment of any of the aforementioned embodiments of improving ocular discomfort, between 1 microgram and 1000 micrograms of the nicotinic acetylcholine receptor agonist is administered into the nasal cavity. In another embodiment of any of the aforementioned embodiments of improving ocular discomfort, between 5 micrograms and 1000 micrograms of the nicotinic acetylcholine receptor agonist is administered into the nasal cavity. In another embodiment of any of the aforementioned embodiments of improving ocular discomfort, between 5 micrograms and 100 micrograms of the nicotinic acetylcholine receptor agonist is administered into the nasal cavity. In another embodiment of any of the aforementioned embodiments of improving ocular discomfort, between 5 micrograms and 50 micrograms of the nicotinic acetylcholine receptor agonist is administered into the nasal cavity. In another embodiment of any of the aforementioned embodiments of improving ocular discomfort, between 10 micrograms and 50 micrograms of the nicotinic acetylcholine receptor agonist is administered into the nasal cavity. In another embodiment of any of the aforementioned embodiments of improving ocular discomfort, between 25 micrograms and 1000 micrograms of the nicotinic acetylcholine receptor agonist is administered into the nasal cavity. In another embodiment of any of the aforementioned embodiments of improving ocular discomfort, between 50 micrograms and 1000 micrograms of the nicotinic acetylcholine receptor agonist is administered into the nasal cavity. In another embodiment of any of the aforementioned embodiments of improving ocular discomfort, between 100 micrograms and 1000 micrograms of the nicotinic acetylcholine receptor agonist is administered into the nasal cavity. In another embodiment of any of the aforementioned embodiments of improving ocular discomfort, between 100 micrograms and 750 micrograms of the nicotinic acetylcholine receptor agonist is administered into the nasal cavity. In another embodiment of any of the aforementioned embodiments of improving ocular discomfort, between 150 micrograms and 750 micrograms of the nicotinic acetylcholine receptor agonist is administered into the nasal cavity. In another embodiment of any of the aforementioned embodiments of improving ocular discomfort, between 150 micrograms and 600 micrograms of the nicotinic acetylcholine receptor agonist is administered into the nasal cavity.

In another embodiment of any of the aforementioned embodiments of improving ocular discomfort, the nicotinic acetylcholine receptor agonist is administered once daily. In another embodiment of any of the aforementioned embodiments of improving ocular discomfort, the nicotinic acetylcholine receptor agonist is administered at least once daily. In another embodiment of any of the aforementioned embodiments of improving ocular discomfort, the nicotinic acetylcholine receptor agonist is administered twice daily. In another embodiment of any of the aforementioned embodiments of improving ocular discomfort, the nicotinic acetylcholine receptor agonist is administered at least twice daily. In another embodiment of any of the aforementioned embodiments of improving ocular discomfort, the nicotinic acetylcholine receptor agonist is administered three times daily. In another embodiment of any of the aforementioned embodiments of improving ocular discomfort, the nicotinic acetylcholine receptor agonist is administered at least three times daily. In another embodiment of any of the aforementioned embodiments of improving ocular discomfort, the nicotinic acetylcholine receptor agonist is administered for one day. In another embodiment of any of the aforementioned embodiments of improving ocular discomfort, the nicotinic acetylcholine receptor agonist is administered for at least two days. In another embodiment of any of the aforementioned embodiments of improving ocular discomfort, the nicotinic acetylcholine receptor agonist is administered for at least three days. In another embodiment of any of the aforementioned embodiments of improving ocular discomfort, the nicotinic acetylcholine receptor agonist is administered for at least four days. In another embodiment of any of the aforementioned embodiments of improving ocular discomfort, the nicotinic acetylcholine receptor agonist is administered for at least five days. In another embodiment of any of the aforementioned embodiments of improving ocular discomfort, the nicotinic acetylcholine receptor agonist is administered for at least seven days. In another embodiment of any of the aforementioned embodiments of improving ocular discomfort, the nicotinic acetylcholine receptor agonist is administered for at least ten days. In another embodiment of any of the aforementioned embodiments of improving ocular discomfort, the nicotinic acetylcholine receptor agonist is administered for at least fourteen days. In another embodiment of any of the aforementioned embodiments of improving ocular discomfort, the nicotinic acetylcholine receptor agonist is administered for at least twenty one days. In another embodiment of any of the aforementioned embodiments of improving ocular discomfort, the nicotinic acetylcholine receptor agonist is administered for at least thirty days.

In another embodiment of any of the aforementioned embodiments of improving ocular discomfort, the nicotinic acetylcholine receptor agonist is administered in alternating nostrils.

In another embodiment of any of the aforementioned embodiments of improving ocular discomfort, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of improving ocular discomfort, the nicotinic acetylcholine receptor agonist is administered into the nasal cavity as a liquid. In another embodiment of any of the aforementioned embodiments of improving ocular discomfort, the nicotinic acetylcholine receptor agonist is administered into the nasal cavity as a suspension. In another embodiment of any of the aforementioned embodiments of improving ocular discomfort, the nicotinic acetylcholine receptor agonist is administered into the nasal cavity as an aerosol. In another embodiment of any of the aforementioned embodiments of improving ocular discomfort, the nicotinic acetylcholine receptor agonist is administered into the nasal cavity as a gel. In another embodiment of any of the aforementioned embodiments of improving ocular discomfort, the nicotinic acetylcholine receptor agonist is administered into the nasal cavity as an ointment. In another embodiment of any of the aforementioned embodiments of improving ocular discomfort, the nicotinic acetylcholine receptor agonist is administered into the nasal cavity as a dry powder. In another embodiment of any of the aforementioned embodiments of improving ocular discomfort, the nicotinic acetylcholine receptor agonist is administered into the nasal cavity as a cream. In another embodiment of any of the aforementioned embodiments of improving ocular discomfort, the nicotinic acetylcholine receptor agonist is administered into the nasal cavity as a paste. In another embodiment of any of the aforementioned embodiments of improving ocular discomfort, the nicotinic acetylcholine receptor agonist is administered into the nasal cavity as a lotion. In another embodiment of any of the aforementioned embodiments of improving ocular discomfort, the nicotinic acetylcholine receptor agonist is administered into the nasal cavity as a balm.

In another embodiment of any of the aforementioned embodiments of improving ocular discomfort, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of improving ocular discomfort, the nicotinic acetylcholine receptor agonist is administered into the nasal cavity by a syringe. In another embodiment of any of the aforementioned embodiments of improving ocular discomfort, the nicotinic acetylcholine receptor agonist is administered into the nasal cavity by a dropper. In another embodiment of any of the aforementioned embodiments of improving ocular discomfort, the nicotinic acetylcholine receptor agonist is administered into the nasal cavity by a bottle nebulizer. In another embodiment of any of the aforementioned embodiments of improving ocular discomfort, the nicotinic acetylcholine receptor agonist is administered into the nasal cavity by an atomization pump. In another embodiment of any of the aforementioned embodiments of improving ocular discomfort, the nicotinic acetylcholine receptor agonist is administered into the nasal cavity by an inhaler. In another embodiment of any of the aforementioned embodiments of improving ocular discomfort, the nicotinic acetylcholine receptor agonist is administered into the nasal cavity by a powder spray device. In another embodiment of any of the aforementioned embodiments of improving ocular discomfort, the nicotinic acetylcholine receptor agonist is administered into the nasal cavity by a vaporizer. In another embodiment of any of the aforementioned embodiments of improving ocular discomfort, the nicotinic acetylcholine receptor agonist is administered into the nasal cavity by a patch. In another embodiment of any of the aforementioned embodiments of improving ocular discomfort, the nicotinic acetylcholine receptor agonist is administered into the nasal cavity by a medicated stick. In another embodiment of any of the aforementioned embodiments of improving ocular discomfort, the nicotinic acetylcholine receptor agonist is administered into the nasal cavity by a pipette. In another embodiment of any of the aforementioned embodiments of improving ocular discomfort, the nicotinic acetylcholine receptor agonist is administered into the nasal cavity by a jet of liquid.

In another embodiment of any of the aforementioned embodiments of improving ocular discomfort, the trigeminal nerve is activated. In a further embodiment of improving ocular discomfort, the anterior ethmoidal nerve is activated. In another embodiment of any of the aforementioned embodiments of improving ocular discomfort, the nasolacrimal reflex is activated.

Improved Ocular Surface Health

Provided herein, in some embodiments, is a method of improving ocular surface health in a subject. In some embodiments, is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of improving ocular surface health, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of improving ocular surface health, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of improving ocular surface health, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of improving ocular surface health, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of improving ocular surface health, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of improving ocular surface health, further comprising the local administration of one or more substances that prevent or facilitate the recovery of the nicotinic acetylcholine receptor from the desensitized state. In some embodiments is a method of improving ocular surface health, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of improving ocular surface health, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular surface health, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of improving ocular surface health, further comprising the local administration of protein kinase C (PKC) or factors that upregulate or up-modulate PKC. In some embodiments is a method of improving ocular surface health, further comprising the local administration of cAMP-dependent protein kinase (PKA) or factors that upregulate or up-modulate PKA. In some embodiments is a method of improving ocular surface health, further comprising the local administration of a calcineurin inhibitor. In some embodiments is a method of improving ocular surface health, further comprising the local administration of a calcineurin inhibitor, wherein the calcineurin inhibitor is selected from cyclosporine, pimecrolimus, and tacrolimus. In some embodiments is a method of improving ocular surface health, further comprising the local administration of cyclosporine. In some embodiments is a method of improving ocular surface health, further comprising the local administration of pimecrolimus. In some embodiments is a method of improving ocular surface health, further comprising the local administration of tacrolimus.

In a further embodiment of any of the aforementioned embodiments of improving ocular surface health, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of improving ocular surface health, the nicotinic acetylcholine receptor agonist is nicotine. In another embodiment of any of the aforementioned embodiments of improving ocular surface health, the nicotinic acetylcholine receptor agonist is cytisine. In another embodiment of any of the aforementioned embodiments of improving ocular surface health, the nicotinic acetylcholine receptor agonist is epibatidine. In another embodiment of any of the aforementioned embodiments of improving ocular surface health, the nicotinic acetylcholine receptor agonist is varenicline. In another embodiment of any of the aforementioned embodiments of improving ocular surface health, the nicotinic acetylcholine receptor agonist is tebanicline. In another embodiment of any of the aforementioned embodiments of improving ocular surface health, the nicotinic acetylcholine receptor agonist is DBO-83. In another embodiment of any of the aforementioned embodiments of improving ocular surface health, the nicotinic acetylcholine receptor agonist is CC4. In another embodiment of any of the aforementioned embodiments of improving ocular surface health, the nicotinic acetylcholine receptor agonist is ABT-418. In another embodiment of any of the aforementioned embodiments of improving ocular surface health, the nicotinic acetylcholine receptor agonist is ABT-366833. In another embodiment of any of the aforementioned embodiments of improving ocular surface health, the nicotinic acetylcholine receptor agonist is ABT-202. In another embodiment of any of the aforementioned embodiments of improving ocular surface health, the nicotinic acetylcholine receptor agonist is ABT-894. In another embodiment of any of the aforementioned embodiments of improving ocular surface health, the nicotinic acetylcholine receptor agonist is SIB-1663. In another embodiment of any of the aforementioned embodiments of improving ocular surface health, the nicotinic acetylcholine receptor agonist is GTS-21. In another embodiment of any of the aforementioned embodiments of improving ocular surface health, the nicotinic acetylcholine receptor agonist is PHA-543613. In another embodiment of any of the aforementioned embodiments of improving ocular surface health, the nicotinic acetylcholine receptor agonist is PNU-282987. In another embodiment of any of the aforementioned embodiments of improving ocular surface health, the nicotinic acetylcholine receptor agonist is LY-2087101. In another embodiment of any of the aforementioned embodiments of improving ocular surface health, the nicotinic acetylcholine receptor agonist is A85380. In another embodiment of any of the aforementioned embodiments of improving ocular surface health, the nicotinic acetylcholine receptor agonist is 5-I-A85380.

In a further embodiment of any of the aforementioned embodiments of improving ocular surface health, the nicotinic acetylcholine receptor agonist is selected from a compound disclosed in WO 2008/057938, WO 2009/111550, WO 2010/028011, or WO 2010/028033.

In another embodiment of any of the aforementioned embodiments of improving ocular surface health, at least 1 microgram of the nicotinic acetylcholine receptor agonist is administered into the nasal cavity. In another embodiment of any of the aforementioned embodiments of improving ocular surface health, at least 5 micrograms of the nicotinic acetylcholine receptor agonist is administered into the nasal cavity. In another embodiment of any of the aforementioned embodiments of improving ocular surface health, at least 10 micrograms of the nicotinic acetylcholine receptor agonist is administered into the nasal cavity. In another embodiment of any of the aforementioned embodiments of improving ocular surface health, at least 25 micrograms of the nicotinic acetylcholine receptor agonist is administered into the nasal cavity. In another embodiment of any of the aforementioned embodiments of improving ocular surface health, at least 50 micrograms of the nicotinic acetylcholine receptor agonist is administered into the nasal cavity. In another embodiment of any of the aforementioned embodiments of improving ocular surface health, at least 100 micrograms of the nicotinic acetylcholine receptor agonist is administered into the nasal cavity. In another embodiment of any of the aforementioned embodiments of improving ocular surface health, at least 250 micrograms of the nicotinic acetylcholine receptor agonist is administered into the nasal cavity. In another embodiment of any of the aforementioned embodiments of improving ocular surface health, at least 500 micrograms of the nicotinic acetylcholine receptor agonist is administered into the nasal cavity. In another embodiment of any of the aforementioned embodiments of improving ocular surface health, at least 750 micrograms of the nicotinic acetylcholine receptor agonist is administered into the nasal cavity. In another embodiment of any of the aforementioned embodiments of improving ocular surface health, at least 1000 micrograms of the nicotinic acetylcholine receptor agonist is administered into the nasal cavity. In another embodiment of any of the aforementioned embodiments of improving ocular surface health, between 1 microgram and 1000 micrograms of the nicotinic acetylcholine receptor agonist is administered into the nasal cavity. In another embodiment of any of the aforementioned embodiments of improving ocular surface health, between 5 micrograms and 1000 micrograms of the nicotinic acetylcholine receptor agonist is administered into the nasal cavity. In another embodiment of any of the aforementioned embodiments of improving ocular surface health, between 5 micrograms and 100 micrograms of the nicotinic acetylcholine receptor agonist is administered into the nasal cavity. In another embodiment of any of the aforementioned embodiments of improving ocular surface health, between 5 micrograms and 50 micrograms of the nicotinic acetylcholine receptor agonist is administered into the nasal cavity. In another embodiment of any of the aforementioned embodiments of improving ocular surface health, between 10 micrograms and 50 micrograms of the nicotinic acetylcholine receptor agonist is administered into the nasal cavity. In another embodiment of any of the aforementioned embodiments of improving ocular surface health, between 25 micrograms and 1000 micrograms of the nicotinic acetylcholine receptor agonist is administered into the nasal cavity. In another embodiment of any of the aforementioned embodiments of improving ocular surface health, between 50 micrograms and 1000 micrograms of the nicotinic acetylcholine receptor agonist is administered into the nasal cavity. In another embodiment of any of the aforementioned embodiments of improving ocular surface health, between 100 micrograms and 1000 micrograms of the nicotinic acetylcholine receptor agonist is administered into the nasal cavity. In another embodiment of any of the aforementioned embodiments of improving ocular surface health, between 100 micrograms and 750 micrograms of the nicotinic acetylcholine receptor agonist is administered into the nasal cavity. In another embodiment of any of the aforementioned embodiments of improving ocular surface health, between 150 micrograms and 750 micrograms of the nicotinic acetylcholine receptor agonist is administered into the nasal cavity. In another embodiment of any of the aforementioned embodiments of improving ocular surface health, between 150 micrograms and 600 micrograms of the nicotinic acetylcholine receptor agonist is administered into the nasal cavity.

In another embodiment of any of the aforementioned embodiments of improving ocular surface health, the nicotinic acetylcholine receptor agonist is administered once daily. In another embodiment of any of the aforementioned embodiments of improving ocular surface health, the nicotinic acetylcholine receptor agonist is administered at least once daily. In another embodiment of any of the aforementioned embodiments of improving ocular surface health, the nicotinic acetylcholine receptor agonist is administered twice daily. In another embodiment of any of the aforementioned embodiments of improving ocular surface health, the nicotinic acetylcholine receptor agonist is administered at least twice daily. In another embodiment of any of the aforementioned embodiments of improving ocular surface health, the nicotinic acetylcholine receptor agonist is administered three times daily. In another embodiment of any of the aforementioned embodiments of improving ocular surface health, the nicotinic acetylcholine receptor agonist is administered at least three times daily. In another embodiment of any of the aforementioned embodiments of improving ocular surface health, the nicotinic acetylcholine receptor agonist is administered for one day. In another embodiment of any of the aforementioned embodiments of improving ocular surface health, the nicotinic acetylcholine receptor agonist is administered for at least two days. In another embodiment of any of the aforementioned embodiments of improving ocular surface health, the nicotinic acetylcholine receptor agonist is administered for at least three days. In another embodiment of any of the aforementioned embodiments of improving ocular surface health, the nicotinic acetylcholine receptor agonist is administered for at least four days. In another embodiment of any of the aforementioned embodiments of improving ocular surface health, the nicotinic acetylcholine receptor agonist is administered for at least five days. In another embodiment of any of the aforementioned embodiments of improving ocular surface health, the nicotinic acetylcholine receptor agonist is administered for at least seven days. In another embodiment of any of the aforementioned embodiments of improving ocular surface health, the nicotinic acetylcholine receptor agonist is administered for at least ten days. In another embodiment of any of the aforementioned embodiments of improving ocular surface health, the nicotinic acetylcholine receptor agonist is administered for at least fourteen days. In another embodiment of any of the aforementioned embodiments of improving ocular surface health, the nicotinic acetylcholine receptor agonist is administered for at least twenty one days. In another embodiment of any of the aforementioned embodiments of improving ocular surface health, the nicotinic acetylcholine receptor agonist is administered for at least thirty days.

In another embodiment of any of the aforementioned embodiments of improving ocular surface health, the nicotinic acetylcholine receptor agonist is administered in alternating nostrils.

In another embodiment of any of the aforementioned embodiments of improving ocular surface health, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of improving ocular surface health, the nicotinic acetylcholine receptor agonist is administered into the nasal cavity as a liquid. In another embodiment of any of the aforementioned embodiments of improving ocular surface health, the nicotinic acetylcholine receptor agonist is administered into the nasal cavity as a suspension. In another embodiment of any of the aforementioned embodiments of improving ocular surface health, the nicotinic acetylcholine receptor agonist is administered into the nasal cavity as an aerosol. In another embodiment of any of the aforementioned embodiments of improving ocular surface health, the nicotinic acetylcholine receptor agonist is administered into the nasal cavity as a gel. In another embodiment of any of the aforementioned embodiments of improving ocular surface health, the nicotinic acetylcholine receptor agonist is administered into the nasal cavity as an ointment. In another embodiment of any of the aforementioned embodiments of improving ocular surface health, the nicotinic acetylcholine receptor agonist is administered into the nasal cavity as a dry powder. In another embodiment of any of the aforementioned embodiments of improving ocular surface health, the nicotinic acetylcholine receptor agonist is administered into the nasal cavity as a cream. In another embodiment of any of the aforementioned embodiments of improving ocular surface health, the nicotinic acetylcholine receptor agonist is administered into the nasal cavity as a paste. In another embodiment of any of the aforementioned embodiments of improving ocular surface health, the nicotinic acetylcholine receptor agonist is administered into the nasal cavity as a lotion. In another embodiment of any of the aforementioned embodiments of improving ocular surface health, the nicotinic acetylcholine receptor agonist is administered into the nasal cavity as a balm.

In another embodiment of any of the aforementioned embodiments of improving ocular surface health, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of improving ocular surface health, the nicotinic acetylcholine receptor agonist is administered into the nasal cavity by a syringe. In another embodiment of any of the aforementioned embodiments of improving ocular surface health, the nicotinic acetylcholine receptor agonist is administered into the nasal cavity by a dropper. In another embodiment of any of the aforementioned embodiments of improving ocular surface health, the nicotinic acetylcholine receptor agonist is administered into the nasal cavity by a bottle nebulizer. In another embodiment of any of the aforementioned embodiments of improving ocular surface health, the nicotinic acetylcholine receptor agonist is administered into the nasal cavity by an atomization pump. In another embodiment of any of the aforementioned embodiments of improving ocular surface health, the nicotinic acetylcholine receptor agonist is administered into the nasal cavity by an inhaler. In another embodiment of any of the aforementioned embodiments of improving ocular surface health, the nicotinic acetylcholine receptor agonist is administered into the nasal cavity by a powder spray device. In another embodiment of any of the aforementioned embodiments of improving ocular surface health, the nicotinic acetylcholine receptor agonist is administered into the nasal cavity by a vaporizer. In another embodiment of any of the aforementioned embodiments of improving ocular surface health, the nicotinic acetylcholine receptor agonist is administered into the nasal cavity by a patch. In another embodiment of any of the aforementioned embodiments of improving ocular surface health, the nicotinic acetylcholine receptor agonist is administered into the nasal cavity by a medicated stick. In another embodiment of any of the aforementioned embodiments of improving ocular surface health, the nicotinic acetylcholine receptor agonist is administered into the nasal cavity by a pipette. In another embodiment of any of the aforementioned embodiments of improving ocular surface health, the nicotinic acetylcholine receptor agonist is administered into the nasal cavity by a jet of liquid.

In another embodiment of any of the aforementioned embodiments of improving ocular surface health, the trigeminal nerve is activated. In a further embodiment of any of the aforementioned embodiments of improving ocular surface health, the anterior ethmoidal nerve is activated. In another embodiment of any of the aforementioned embodiments of improving ocular surface health, the nasolacrimal reflex is activated.

Protecting the Ocular Surface During Environmentally Challenging Conditions

Provided herein, in some embodiments, is a method of protecting the ocular surface during environmentally challenging conditions in a subject. In some embodiments, is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of protecting the ocular surface during environmentally challenging conditions, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of protecting the ocular surface during environmentally challenging conditions, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of protecting the ocular surface during environmentally challenging conditions, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of protecting the ocular surface during environmentally challenging conditions, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of protecting the ocular surface during environmentally challenging conditions, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of protecting the ocular surface during environmentally challenging conditions, further comprising the local administration of one or more substances that prevent or facilitate the recovery of the nicotinic acetylcholine receptor from the desensitized state. In some embodiments is a method of protecting the ocular surface during environmentally challenging conditions, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of protecting the ocular surface during environmentally challenging conditions, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of protecting the ocular surface during environmentally challenging conditions, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of protecting the ocular surface during environmentally challenging conditions, further comprising the local administration of protein kinase C (PKC) or factors that upregulate or up-modulate PKC. In some embodiments is a method of protecting the ocular surface during environmentally challenging conditions, further comprising the local administration of cAMP-dependent protein kinase (PKA) or factors that upregulate or up-modulate PKA. In some embodiments is a method of protecting the ocular surface during environmentally challenging conditions, further comprising the local administration of a calcineurin inhibitor. In some embodiments is a method of protecting the ocular surface during environmentally challenging conditions, further comprising the local administration of a calcineurin inhibitor, wherein the calcineurin inhibitor is selected from cyclosporine, pimecrolimus, and tacrolimus. In some embodiments is a method of protecting the ocular surface during environmentally challenging conditions, further comprising the local administration of cyclosporine. In some embodiments is a method of protecting the ocular surface during environmentally challenging conditions, further comprising the local administration of pimecrolimus. In some embodiments is a method of protecting the ocular surface during environmentally challenging conditions, further comprising the local administration of tacrolimus.

In a further embodiment of any of the aforementioned embodiments of protecting the ocular surface during environmentally challenging conditions, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of protecting the ocular surface during environmentally challenging conditions, the nicotinic acetylcholine receptor agonist is nicotine. In another embodiment of any of the aforementioned embodiments of protecting the ocular surface during environmentally challenging conditions, the nicotinic acetylcholine receptor agonist is cytisine. In another embodiment of any of the aforementioned embodiments of protecting the ocular surface during environmentally challenging conditions, the nicotinic acetylcholine receptor agonist is epibatidine. In another embodiment of any of the aforementioned embodiments of protecting the ocular surface during environmentally challenging conditions, the nicotinic acetylcholine receptor agonist is varenicline. In another embodiment of any of the aforementioned embodiments of protecting the ocular surface during environmentally challenging conditions, the nicotinic acetylcholine receptor agonist is tebanicline. In another embodiment of any of the aforementioned embodiments of protecting the ocular surface during environmentally challenging conditions, the nicotinic acetylcholine receptor agonist is DBO-83. In another embodiment of any of the aforementioned embodiments of protecting the ocular surface during environmentally challenging conditions, the nicotinic acetylcholine receptor agonist is CC4. In another embodiment of any of the aforementioned embodiments of protecting the ocular surface during environmentally challenging conditions, the nicotinic acetylcholine receptor agonist is ABT-418. In another embodiment of any of the aforementioned embodiments of protecting the ocular surface during environmentally challenging conditions, the nicotinic acetylcholine receptor agonist is ABT-366833. In another embodiment of any of the aforementioned embodiments of protecting the ocular surface during environmentally challenging conditions, the nicotinic acetylcholine receptor agonist is ABT-202. In another embodiment of any of the aforementioned embodiments of protecting the ocular surface during environmentally challenging conditions, the nicotinic acetylcholine receptor agonist is ABT-894. In another embodiment of any of the aforementioned embodiments of protecting the ocular surface during environmentally challenging conditions, the nicotinic acetylcholine receptor agonist is SIB-1663. In another embodiment of any of the aforementioned embodiments of protecting the ocular surface during environmentally challenging conditions, the nicotinic acetylcholine receptor agonist is GTS-21. In another embodiment of any of the aforementioned embodiments of protecting the ocular surface during environmentally challenging conditions, the nicotinic acetylcholine receptor agonist is PHA-543613. In another embodiment of any of the aforementioned embodiments of protecting the ocular surface during environmentally challenging conditions, the nicotinic acetylcholine receptor agonist is PNU-282987. In another embodiment of any of the aforementioned embodiments of protecting the ocular surface during environmentally challenging conditions, the nicotinic acetylcholine receptor agonist is LY-2087101. In another embodiment of any of the aforementioned embodiments of protecting the ocular surface during environmentally challenging conditions, the nicotinic acetylcholine receptor agonist is A85380. In another embodiment of any of the aforementioned embodiments of protecting the ocular surface during environmentally challenging conditions, the nicotinic acetylcholine receptor agonist is 5-I-A85380.

In a further embodiment of any of the aforementioned embodiments of protecting the ocular surface during environmentally challenging conditions, the nicotinic acetylcholine receptor agonist is selected from a compound disclosed in WO 2008/057938, WO 2009/111550, WO 2010/028011, or WO 2010/028033.

In another embodiment of any of the aforementioned embodiments of protecting the ocular surface during environmentally challenging conditions, at least 1 microgram of the nicotinic acetylcholine receptor agonist is administered into the nasal cavity. In another embodiment of any of the aforementioned embodiments of protecting the ocular surface during environmentally challenging conditions, at least 5 micrograms of the nicotinic acetylcholine receptor agonist is administered into the nasal cavity. In another embodiment of any of the aforementioned embodiments of protecting the ocular surface during environmentally challenging conditions, at least 10 micrograms of the nicotinic acetylcholine receptor agonist is administered into the nasal cavity. In another embodiment of any of the aforementioned embodiments of protecting the ocular surface during environmentally challenging conditions, at least 25 micrograms of the nicotinic acetylcholine receptor agonist is administered into the nasal cavity. In another embodiment of any of the aforementioned embodiments of protecting the ocular surface during environmentally challenging conditions, at least 50 micrograms of the nicotinic acetylcholine receptor agonist is administered into the nasal cavity. In another embodiment of any of the aforementioned embodiments of protecting the ocular surface during environmentally challenging conditions, at least 100 micrograms of the nicotinic acetylcholine receptor agonist is administered into the nasal cavity. In another embodiment of any of the aforementioned embodiments of protecting the ocular surface during environmentally challenging conditions, at least 250 micrograms of the nicotinic acetylcholine receptor agonist is administered into the nasal cavity. In another embodiment of any of the aforementioned embodiments of protecting the ocular surface during environmentally challenging conditions, at least 500 micrograms of the nicotinic acetylcholine receptor agonist is administered into the nasal cavity. In another embodiment of any of the aforementioned embodiments of protecting the ocular surface during environmentally challenging conditions, at least 750 micrograms of the nicotinic acetylcholine receptor agonist is administered into the nasal cavity. In another embodiment of any of the aforementioned embodiments of protecting the ocular surface during environmentally challenging conditions, at least 1000 micrograms of the nicotinic acetylcholine receptor agonist is administered into the nasal cavity. In another embodiment of any of the aforementioned embodiments of protecting the ocular surface during environmentally challenging conditions, between 1 microgram and 1000 micrograms of the nicotinic acetylcholine receptor agonist is administered into the nasal cavity. In another embodiment of any of the aforementioned embodiments of protecting the ocular surface during environmentally challenging conditions, between 5 micrograms and 1000 micrograms of the nicotinic acetylcholine receptor agonist is administered into the nasal cavity. In another embodiment of any of the aforementioned embodiments of protecting the ocular surface during environmentally challenging conditions, between 5 micrograms and 100 micrograms of the nicotinic acetylcholine receptor agonist is administered into the nasal cavity. In another embodiment of any of the aforementioned embodiments of protecting the ocular surface during environmentally challenging conditions, between 5 micrograms and 50 micrograms of the nicotinic acetylcholine receptor agonist is administered into the nasal cavity. In another embodiment of any of the aforementioned embodiments of protecting the ocular surface during environmentally challenging conditions, between 10 micrograms and 50 micrograms of the nicotinic acetylcholine receptor agonist is administered into the nasal cavity. In another embodiment of any of the aforementioned embodiments of protecting the ocular surface during environmentally challenging conditions, between 25 micrograms and 1000 micrograms of the nicotinic acetylcholine receptor agonist is administered into the nasal cavity. In another embodiment of any of the aforementioned embodiments of protecting the ocular surface during environmentally challenging conditions, between 50 micrograms and 1000 micrograms of the nicotinic acetylcholine receptor agonist is administered into the nasal cavity. In another embodiment of any of the aforementioned embodiments of protecting the ocular surface during environmentally challenging conditions, between 100 micrograms and 1000 micrograms of the nicotinic acetylcholine receptor agonist is administered into the nasal cavity. In another embodiment of any of the aforementioned embodiments of protecting the ocular surface during environmentally challenging conditions, between 100 micrograms and 750 micrograms of the nicotinic acetylcholine receptor agonist is administered into the nasal cavity. In another embodiment of any of the aforementioned embodiments of protecting the ocular surface during environmentally challenging conditions, between 150 micrograms and 750 micrograms of the nicotinic acetylcholine receptor agonist is administered into the nasal cavity. In another embodiment of any of the aforementioned embodiments of protecting the ocular surface during environmentally challenging conditions, between 150 micrograms and 600 micrograms of the nicotinic acetylcholine receptor agonist is administered into the nasal cavity.

In another embodiment of any of the aforementioned embodiments of protecting the ocular surface during environmentally challenging conditions, the nicotinic acetylcholine receptor agonist is administered once daily. In another embodiment of any of the aforementioned embodiments of protecting the ocular surface during environmentally challenging conditions, the nicotinic acetylcholine receptor agonist is administered at least once daily. In another embodiment of any of the aforementioned embodiments of protecting the ocular surface during environmentally challenging conditions, the nicotinic acetylcholine receptor agonist is administered twice daily. In another embodiment of any of the aforementioned embodiments of protecting the ocular surface during environmentally challenging conditions, the nicotinic acetylcholine receptor agonist is administered at least twice daily. In another embodiment of any of the aforementioned embodiments of protecting the ocular surface during environmentally challenging conditions, the nicotinic acetylcholine receptor agonist is administered three times daily. In another embodiment of any of the aforementioned embodiments of protecting the ocular surface during environmentally challenging conditions, the nicotinic acetylcholine receptor agonist is administered at least three times daily. In another embodiment of any of the aforementioned embodiments of protecting the ocular surface during environmentally challenging conditions, the nicotinic acetylcholine receptor agonist is administered for one day. In another embodiment of any of the aforementioned embodiments of protecting the ocular surface during environmentally challenging conditions, the nicotinic acetylcholine receptor agonist is administered for at least two days. In another embodiment of any of the aforementioned embodiments of protecting the ocular surface during environmentally challenging conditions, the nicotinic acetylcholine receptor agonist is administered for at least three days. In another embodiment of any of the aforementioned embodiments of protecting the ocular surface during environmentally challenging conditions, the nicotinic acetylcholine receptor agonist is administered for at least four days. In another embodiment of any of the aforementioned embodiments of protecting the ocular surface during environmentally challenging conditions, the nicotinic acetylcholine receptor agonist is administered for at least five days. In another embodiment of any of the aforementioned embodiments of protecting the ocular surface during environmentally challenging conditions, the nicotinic acetylcholine receptor agonist is administered for at least seven days. In another embodiment of any of the aforementioned embodiments of protecting the ocular surface during environmentally challenging conditions, the nicotinic acetylcholine receptor agonist is administered for at least ten days. In another embodiment of any of the aforementioned embodiments of protecting the ocular surface during environmentally challenging conditions, the nicotinic acetylcholine receptor agonist is administered for at least fourteen days. In another embodiment of any of the aforementioned embodiments of protecting the ocular surface during environmentally challenging conditions, the nicotinic acetylcholine receptor agonist is administered for at least twenty one days. In another embodiment of any of the aforementioned embodiments of protecting the ocular surface during environmentally challenging conditions, the nicotinic acetylcholine receptor agonist is administered for at least thirty days.

In another embodiment of any of the aforementioned embodiments of protecting the ocular surface during environmentally challenging conditions, the nicotinic acetylcholine receptor agonist is administered in alternating nostrils.

In another embodiment of any of the aforementioned embodiments of protecting the ocular surface during environmentally challenging conditions, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of protecting the ocular surface during environmentally challenging conditions, the nicotinic acetylcholine receptor agonist is administered into the nasal cavity as a liquid. In another embodiment of any of the aforementioned embodiments of protecting the ocular surface during environmentally challenging conditions, the nicotinic acetylcholine receptor agonist is administered into the nasal cavity as a suspension. In another embodiment of any of the aforementioned embodiments of protecting the ocular surface during environmentally challenging conditions, the nicotinic acetylcholine receptor agonist is administered into the nasal cavity as an aerosol. In another embodiment of any of the aforementioned embodiments of protecting the ocular surface during environmentally challenging conditions, the nicotinic acetylcholine receptor agonist is administered into the nasal cavity as a gel. In another embodiment of any of the aforementioned embodiments of protecting the ocular surface during environmentally challenging conditions, the nicotinic acetylcholine receptor agonist is administered into the nasal cavity as an ointment. In another embodiment of any of the aforementioned embodiments of protecting the ocular surface during environmentally challenging conditions, the nicotinic acetylcholine receptor agonist is administered into the nasal cavity as a dry powder. In another embodiment of any of the aforementioned embodiments of protecting the ocular surface during environmentally challenging conditions, the nicotinic acetylcholine receptor agonist is administered into the nasal cavity as a cream. In another embodiment of any of the aforementioned embodiments of protecting the ocular surface during environmentally challenging conditions, the nicotinic acetylcholine receptor agonist is administered into the nasal cavity as a paste. In another embodiment of any of the aforementioned embodiments of protecting the ocular surface during environmentally challenging conditions, the nicotinic acetylcholine receptor agonist is administered into the nasal cavity as a lotion. In another embodiment of any of the aforementioned embodiments of protecting the ocular surface during environmentally challenging conditions, the nicotinic acetylcholine receptor agonist is administered into the nasal cavity as a balm.

In another embodiment of any of the aforementioned embodiments of protecting the ocular surface during environmentally challenging conditions, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of protecting the ocular surface during environmentally challenging conditions, the nicotinic acetylcholine receptor agonist is administered into the nasal cavity by a syringe. In another embodiment of any of the aforementioned embodiments of protecting the ocular surface during environmentally challenging conditions, the nicotinic acetylcholine receptor agonist is administered into the nasal cavity by a dropper. In another embodiment of any of the aforementioned embodiments of protecting the ocular surface during environmentally challenging conditions, the nicotinic acetylcholine receptor agonist is administered into the nasal cavity by a bottle nebulizer. In another embodiment of any of the aforementioned embodiments of protecting the ocular surface during environmentally challenging conditions, the nicotinic acetylcholine receptor agonist is administered into the nasal cavity by an atomization pump. In another embodiment of any of the aforementioned embodiments of protecting the ocular surface during environmentally challenging conditions, the nicotinic acetylcholine receptor agonist is administered into the nasal cavity by an inhaler. In another embodiment of any of the aforementioned embodiments of protecting the ocular surface during environmentally challenging conditions, the nicotinic acetylcholine receptor agonist is administered into the nasal cavity by a powder spray device. In another embodiment of any of the aforementioned embodiments of protecting the ocular surface during environmentally challenging conditions, the nicotinic acetylcholine receptor agonist is administered into the nasal cavity by a vaporizer. In another embodiment of any of the aforementioned embodiments of protecting the ocular surface during environmentally challenging conditions, the nicotinic acetylcholine receptor agonist is administered into the nasal cavity by a patch. In another embodiment of any of the aforementioned embodiments of protecting the ocular surface during environmentally challenging conditions, the nicotinic acetylcholine receptor agonist is administered into the nasal cavity by a medicated stick. In another embodiment of any of the aforementioned embodiments of protecting the ocular surface during environmentally challenging conditions, the nicotinic acetylcholine receptor agonist is administered into the nasal cavity by a pipette. In another embodiment of any of the aforementioned embodiments of protecting the ocular surface during environmentally challenging conditions, the nicotinic acetylcholine receptor agonist is administered into the nasal cavity by a jet of liquid.

In another embodiment of any of the aforementioned embodiments of protecting the ocular surface during environmentally challenging conditions, the trigeminal nerve is activated. In a further embodiment of protecting the ocular surface during environmentally challenging conditions, the anterior ethmoidal nerve is activated. In another embodiment of any of the aforementioned embodiments of protecting the ocular surface during environmentally challenging conditions, the nasolacrimal reflex is activated.

Increasing Mucin Content on the Ocular Surface

Provided herein, in some embodiments, is a method of increasing mucin content on the ocular surface in a subject. In some embodiments, is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of increasing mucin content on the ocular surface, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of increasing mucin content on the ocular surface, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of increasing mucin content on the ocular surface, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of increasing mucin content on the ocular surface, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing mucin content on the ocular surface, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of increasing mucin content on the ocular surface, further comprising the local administration of one or more substances that prevent or facilitate the recovery of the nicotinic acetylcholine receptor from the desensitized state. In some embodiments is a method of increasing mucin content on the ocular surface, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of increasing mucin content on the ocular surface, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing mucin content on the ocular surface, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing mucin content on the ocular surface, further comprising the local administration of protein kinase C (PKC) or factors that upregulate or up-modulate PKC. In some embodiments is a method of increasing mucin content on the ocular surface, further comprising the local administration of cAMP-dependent protein kinase (PKA) or factors that upregulate or up-modulate PKA. In some embodiments is a method of increasing mucin content on the ocular surface, further comprising the local administration of a calcineurin inhibitor. In some embodiments is a method of increasing mucin content on the ocular surface, further comprising the local administration of a calcineurin inhibitor, wherein the calcineurin inhibitor is selected from cyclosporine, pimecrolimus, and tacrolimus. In some embodiments is a method of increasing mucin content on the ocular surface, further comprising the local administration of cyclosporine. In some embodiments is a method of increasing mucin content on the ocular surface, further comprising the local administration of pimecrolimus. In some embodiments is a method of increasing mucin content on the ocular surface, further comprising the local administration of tacrolimus.

In a further embodiment of any of the aforementioned embodiments of increasing mucin content on the ocular surface, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of increasing mucin content on the ocular surface, the nicotinic acetylcholine receptor agonist is nicotine. In another embodiment of any of the aforementioned embodiments of increasing mucin content on the ocular surface, the nicotinic acetylcholine receptor agonist is cytisine. In another embodiment of any of the aforementioned embodiments of increasing mucin content on the ocular surface, the nicotinic acetylcholine receptor agonist is epibatidine. In another embodiment of any of the aforementioned embodiments of increasing mucin content on the ocular surface, the nicotinic acetylcholine receptor agonist is varenicline. In another embodiment of any of the aforementioned embodiments of increasing mucin content on the ocular surface, the nicotinic acetylcholine receptor agonist is tebanicline. In another embodiment of any of the aforementioned embodiments of increasing mucin content on the ocular surface, the nicotinic acetylcholine receptor agonist is DBO-83. In another embodiment of any of the aforementioned embodiments of increasing mucin content on the ocular surface, the nicotinic acetylcholine receptor agonist is CC4. In another embodiment of any of the aforementioned embodiments of increasing mucin content on the ocular surface, the nicotinic acetylcholine receptor agonist is ABT-418. In another embodiment of any of the aforementioned embodiments of increasing mucin content on the ocular surface, the nicotinic acetylcholine receptor agonist is ABT-366833. In another embodiment of any of the aforementioned embodiments of increasing mucin content on the ocular surface, the nicotinic acetylcholine receptor agonist is ABT-202. In another embodiment of any of the aforementioned embodiments of increasing mucin content on the ocular surface, the nicotinic acetylcholine receptor agonist is ABT-894. In another embodiment of any of the aforementioned embodiments of increasing mucin content on the ocular surface, the nicotinic acetylcholine receptor agonist is SIB-1663. In another embodiment of any of the aforementioned embodiments of increasing mucin content on the ocular surface, the nicotinic acetylcholine receptor agonist is GTS-21. In another embodiment of any of the aforementioned embodiments of increasing mucin content on the ocular surface, the nicotinic acetylcholine receptor agonist is PHA-543613. In another embodiment of any of the aforementioned embodiments of increasing mucin content on the ocular surface, the nicotinic acetylcholine receptor agonist is PNU-282987. In another embodiment of any of the aforementioned embodiments of increasing mucin content on the ocular surface, the nicotinic acetylcholine receptor agonist is LY-2087101. In another embodiment of any of the aforementioned embodiments of increasing mucin content on the ocular surface, the nicotinic acetylcholine receptor agonist is A85380. In another embodiment of any of the aforementioned embodiments of increasing mucin content on the ocular surface, the nicotinic acetylcholine receptor agonist is 5-I-A85380.

In a further embodiment of any of the aforementioned embodiments of increasing mucin content on the ocular surface, the nicotinic acetylcholine receptor agonist is selected from a compound disclosed in WO 2008/057938, WO 2009/111550, WO 2010/028011, or WO 2010/028033.

In another embodiment of any of the aforementioned embodiments of increasing mucin content on the ocular surface, at least 1 microgram of the nicotinic acetylcholine receptor agonist is administered into the nasal cavity. In another embodiment of any of the aforementioned embodiments of increasing mucin content on the ocular surface, at least 5 micrograms of the nicotinic acetylcholine receptor agonist is administered into the nasal cavity. In another embodiment of any of the aforementioned embodiments of increasing mucin content on the ocular surface, at least 10 micrograms of the nicotinic acetylcholine receptor agonist is administered into the nasal cavity. In another embodiment of any of the aforementioned embodiments of increasing mucin content on the ocular surface, at least 25 micrograms of the nicotinic acetylcholine receptor agonist is administered into the nasal cavity. In another embodiment of any of the aforementioned embodiments of increasing mucin content on the ocular surface, at least 50 micrograms of the nicotinic acetylcholine receptor agonist is administered into the nasal cavity. In another embodiment of any of the aforementioned embodiments of increasing mucin content on the ocular surface, at least 100 micrograms of the nicotinic acetylcholine receptor agonist is administered into the nasal cavity. In another embodiment of any of the aforementioned embodiments of increasing mucin content on the ocular surface, at least 250 micrograms of the nicotinic acetylcholine receptor agonist is administered into the nasal cavity. In another embodiment of any of the aforementioned embodiments of increasing mucin content on the ocular surface, at least 500 micrograms of the nicotinic acetylcholine receptor agonist is administered into the nasal cavity. In another embodiment of any of the aforementioned embodiments of increasing mucin content on the ocular surface, at least 750 micrograms of the nicotinic acetylcholine receptor agonist is administered into the nasal cavity. In another embodiment of any of the aforementioned embodiments of increasing mucin content on the ocular surface, at least 1000 micrograms of the nicotinic acetylcholine receptor agonist is administered into the nasal cavity. In another embodiment of any of the aforementioned embodiments of increasing mucin content on the ocular surface, between 1 microgram and 1000 micrograms of the nicotinic acetylcholine receptor agonist is administered into the nasal cavity. In another embodiment of any of the aforementioned embodiments of increasing mucin content on the ocular surface, between 5 micrograms and 1000 micrograms of the nicotinic acetylcholine receptor agonist is administered into the nasal cavity. In another embodiment of any of the aforementioned embodiments of increasing mucin content on the ocular surface, between 5 micrograms and 100 micrograms of the nicotinic acetylcholine receptor agonist is administered into the nasal cavity. In another embodiment of any of the aforementioned embodiments of increasing mucin content on the ocular surface, between 5 micrograms and 50 micrograms of the nicotinic acetylcholine receptor agonist is administered into the nasal cavity. In another embodiment of any of the aforementioned embodiments of increasing mucin content on the ocular surface, between 10 micrograms and 50 micrograms of the nicotinic acetylcholine receptor agonist is administered into the nasal cavity. In another embodiment of any of the aforementioned embodiments of increasing mucin content on the ocular surface, between 25 micrograms and 1000 micrograms of the nicotinic acetylcholine receptor agonist is administered into the nasal cavity. In another embodiment of any of the aforementioned embodiments of increasing mucin content on the ocular surface, between 50 micrograms and 1000 micrograms of the nicotinic acetylcholine receptor agonist is administered into the nasal cavity. In another embodiment of any of the aforementioned embodiments of increasing mucin content on the ocular surface, between 100 micrograms and 1000 micrograms of the nicotinic acetylcholine receptor agonist is administered into the nasal cavity. In another embodiment of any of the aforementioned embodiments of increasing mucin content on the ocular surface, between 100 micrograms and 750 micrograms of the nicotinic acetylcholine receptor agonist is administered into the nasal cavity. In another embodiment of any of the aforementioned embodiments of increasing mucin content on the ocular surface, between 150 micrograms and 750 micrograms of the nicotinic acetylcholine receptor agonist is administered into the nasal cavity. In another embodiment of any of the aforementioned embodiments of increasing mucin content on the ocular surface, between 150 micrograms and 600 micrograms of the nicotinic acetylcholine receptor agonist is administered into the nasal cavity.

In another embodiment of any of the aforementioned embodiments of increasing mucin content on the ocular surface, the nicotinic acetylcholine receptor agonist is administered once daily. In another embodiment of any of the aforementioned embodiments of increasing mucin content on the ocular surface, the nicotinic acetylcholine receptor agonist is administered at least once daily. In another embodiment of any of the aforementioned embodiments of increasing mucin content on the ocular surface, the nicotinic acetylcholine receptor agonist is administered twice daily. In another embodiment of any of the aforementioned embodiments of increasing mucin content on the ocular surface, the nicotinic acetylcholine receptor agonist is administered at least twice daily. In another embodiment of any of the aforementioned embodiments of increasing mucin content on the ocular surface, the nicotinic acetylcholine receptor agonist is administered three times daily. In another embodiment of any of the aforementioned embodiments of increasing mucin content on the ocular surface, the nicotinic acetylcholine receptor agonist is administered at least three times daily. In another embodiment of any of the aforementioned embodiments of increasing mucin content on the ocular surface, the nicotinic acetylcholine receptor agonist is administered for one day. In another embodiment of any of the aforementioned embodiments of increasing mucin content on the ocular surface, the nicotinic acetylcholine receptor agonist is administered for at least two days. In another embodiment of any of the aforementioned embodiments of increasing mucin content on the ocular surface, the nicotinic acetylcholine receptor agonist is administered for at least three days. In another embodiment of any of the aforementioned embodiments of increasing mucin content on the ocular surface, the nicotinic acetylcholine receptor agonist is administered for at least four days. In another embodiment of any of the aforementioned embodiments of increasing mucin content on the ocular surface, the nicotinic acetylcholine receptor agonist is administered for at least five days. In another embodiment of any of the aforementioned embodiments of increasing mucin content on the ocular surface, the nicotinic acetylcholine receptor agonist is administered for at least seven days. In another embodiment of any of the aforementioned embodiments of increasing mucin content on the ocular surface, the nicotinic acetylcholine receptor agonist is administered for at least ten days. In another embodiment of any of the aforementioned embodiments of increasing mucin content on the ocular surface, the nicotinic acetylcholine receptor agonist is administered for at least fourteen days. In another embodiment of any of the aforementioned embodiments of increasing mucin content on the ocular surface, the nicotinic acetylcholine receptor agonist is administered for at least twenty one days. In another embodiment of any of the aforementioned embodiments of increasing mucin content on the ocular surface, the nicotinic acetylcholine receptor agonist is administered for at least thirty days.

In another embodiment of any of the aforementioned embodiments of increasing mucin content on the ocular surface, the nicotinic acetylcholine receptor agonist is administered in alternating nostrils.

In another embodiment of any of the aforementioned embodiments of increasing mucin content on the ocular surface, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of increasing mucin content on the ocular surface, the nicotinic acetylcholine receptor agonist is administered into the nasal cavity as a liquid. In another embodiment of any of the aforementioned embodiments of increasing mucin content on the ocular surface, the nicotinic acetylcholine receptor agonist is administered into the nasal cavity as a suspension. In another embodiment of any of the aforementioned embodiments of increasing mucin content on the ocular surface, the nicotinic acetylcholine receptor agonist is administered into the nasal cavity as an aerosol. In another embodiment of any of the aforementioned embodiments of increasing mucin content on the ocular surface, the nicotinic acetylcholine receptor agonist is administered into the nasal cavity as a gel. In another embodiment of any of the aforementioned embodiments of increasing mucin content on the ocular surface, the nicotinic acetylcholine receptor agonist is administered into the nasal cavity as an ointment. In another embodiment of any of the aforementioned embodiments of increasing mucin content on the ocular surface, the nicotinic acetylcholine receptor agonist is administered into the nasal cavity as a dry powder. In another embodiment of any of the aforementioned embodiments of increasing mucin content on the ocular surface, the nicotinic acetylcholine receptor agonist is administered into the nasal cavity as a cream. In another embodiment of any of the aforementioned embodiments of increasing mucin content on the ocular surface, the nicotinic acetylcholine receptor agonist is administered into the nasal cavity as a paste. In another embodiment of any of the aforementioned embodiments of increasing mucin content on the ocular surface, the nicotinic acetylcholine receptor agonist is administered into the nasal cavity as a lotion. In another embodiment of any of the aforementioned embodiments of increasing mucin content on the ocular surface, the nicotinic acetylcholine receptor agonist is administered into the nasal cavity as a balm.

In another embodiment of any of the aforementioned embodiments of increasing mucin content on the ocular surface, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of increasing mucin content on the ocular surface, the nicotinic acetylcholine receptor agonist is administered into the nasal cavity by a syringe. In another embodiment of any of the aforementioned embodiments of increasing mucin content on the ocular surface, the nicotinic acetylcholine receptor agonist is administered into the nasal cavity by a dropper. In another embodiment of any of the aforementioned embodiments of increasing mucin content on the ocular surface, the nicotinic acetylcholine receptor agonist is administered into the nasal cavity by a bottle nebulizer. In another embodiment of any of the aforementioned embodiments of increasing mucin content on the ocular surface, the nicotinic acetylcholine receptor agonist is administered into the nasal cavity by an atomization pump. In another embodiment of any of the aforementioned embodiments of increasing mucin content on the ocular surface, the nicotinic acetylcholine receptor agonist is administered into the nasal cavity by an inhaler. In another embodiment of any of the aforementioned embodiments of increasing mucin content on the ocular surface, the nicotinic acetylcholine receptor agonist is administered into the nasal cavity by a powder spray device. In another embodiment of any of the aforementioned embodiments of increasing mucin content on the ocular surface, the nicotinic acetylcholine receptor agonist is administered into the nasal cavity by a vaporizer. In another embodiment of any of the aforementioned embodiments of increasing mucin content on the ocular surface, the nicotinic acetylcholine receptor agonist is administered into the nasal cavity by a patch. In another embodiment of any of the aforementioned embodiments of increasing mucin content on the ocular surface, the nicotinic acetylcholine receptor agonist is administered into the nasal cavity by a medicated stick. In another embodiment of any of the aforementioned embodiments of increasing mucin content on the ocular surface, the nicotinic acetylcholine receptor agonist is administered into the nasal cavity by a pipette. In another embodiment of any of the aforementioned embodiments of increasing mucin content on the ocular surface, the nicotinic acetylcholine receptor agonist is administered into the nasal cavity by a jet of liquid.

In another embodiment of any of the aforementioned embodiments of increasing mucin content on the ocular surface, the trigeminal nerve is activated. In a further embodiment of increasing mucin content on the ocular surface, the anterior ethmoidal nerve is activated. In another embodiment of any of the aforementioned embodiments of increasing mucin content on the ocular surface, the nasolacrimal reflex is activated.

Increasing the Amount or Concentration of One or More Lacrimal Proteins

Provided herein, in some embodiments, is a method of increasing the amount or concentration of one or more lacrimal proteins in a subject. In some embodiments, is a method of increasing the amount or concentration of one or more lacrimal proteins, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of increasing the amount or concentration of one or more lacrimal proteins, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of increasing the amount or concentration of one or more lacrimal proteins, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of increasing the amount or concentration of one or more lacrimal proteins, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of increasing the amount or concentration of one or more lacrimal proteins, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of increasing the amount or concentration of one or more lacrimal proteins, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of increasing the amount or concentration of one or more lacrimal proteins, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of increasing the amount or concentration of one or more lacrimal proteins, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of increasing the amount or concentration of one or more lacrimal proteins, wherein the lacrimal protein is epithelial growth factor, lactoferin, lacritin, prolactin, adrenocorticotropic, leucine enkephalin, ALS2CL, ARHGEF19, KIAA1109, PLXNA1, POLG, WIPI1, ZMIZ2 or other proteins of the tear proteome. In some embodiments is a method of increasing the amount or concentration of one or more lacrimal proteins, wherein at least one lacrimal protein is epithelial growth factor. In some embodiments is a method of increasing the amount or concentration of one or more lacrimal proteins, wherein at least one lacrimal protein is lactoferin. In some embodiments is a method of increasing the amount or concentration of one or more lacrimal proteins, wherein at least one lacrimal protein is lacritin. In some embodiments is a method of increasing the amount or concentration of one or more lacrimal proteins, wherein at least one lacrimal protein is prolactin. In some embodiments is a method of increasing the amount or concentration of one or more lacrimal proteins, wherein at least one lacrimal protein is adrenocorticotropic. In some embodiments is a method of increasing the amount or concentration of one or more lacrimal proteins, wherein at least one lacrimal protein is leucine enkephalin. In some embodiments is a method of increasing the amount or concentration of one or more lacrimal proteins, wherein at least one lacrimal protein is ALS2CL. In some embodiments is a method of increasing the amount or concentration of one or more lacrimal proteins, wherein at least one lacrimal protein is ARHGEF19. In some embodiments is a method of increasing the amount or concentration of one or more lacrimal proteins, wherein at least one lacrimal protein is KIAA1109. In some embodiments is a method of increasing the amount or concentration of one or more lacrimal proteins, wherein at least one lacrimal protein is PLXNA1. In some embodiments is a method of increasing the amount or concentration of one or more lacrimal proteins, wherein at least one lacrimal protein is POLG. In some embodiments is a method of increasing the amount or concentration of one or more lacrimal proteins, wherein at least one lacrimal protein is WIPI1. In some embodiments is a method of increasing the amount or concentration of one or more lacrimal proteins, wherein at least one lacrimal protein is ZMIZ2. In some embodiments is a method of increasing the amount or concentration of one or more lacrimal proteins, further comprising the local administration of one or more substances that prevent or facilitate the recovery of the nicotinic acetylcholine receptor from the desensitized state. In some embodiments is a method of increasing the amount or concentration of one or more lacrimal proteins, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of increasing the amount or concentration of one or more lacrimal proteins, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing the amount or concentration of one or more lacrimal proteins, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of increasing the amount or concentration of one or more lacrimal proteins, further comprising the local administration of protein kinase C (PKC) or factors that upregulate or up-modulate PKC. In some embodiments is a method of increasing the amount or concentration of one or more lacrimal proteins, further comprising the local administration of cAMP-dependent protein kinase (PKA) or factors that upregulate or up-modulate PKA. In some embodiments is a method of increasing the amount or concentration of one or more lacrimal proteins, further comprising the local administration of a calcineurin inhibitor. In some embodiments is a method of increasing the amount or concentration of one or more lacrimal proteins, further comprising the local administration of a calcineurin inhibitor, wherein the calcineurin inhibitor is selected from cyclosporine, pimecrolimus, and tacrolimus. In some embodiments is a method of increasing the amount or concentration of one or more lacrimal proteins, further comprising the local administration of cyclosporine. In some embodiments is a method of increasing the amount or concentration of one or more lacrimal proteins, further comprising the local administration of pimecrolimus. In some embodiments is a method of increasing the amount or concentration of one or more lacrimal proteins, further comprising the local administration of tacrolimus.

In a further embodiment of any of the aforementioned embodiments of increasing the amount or concentration of one or more lacrimal proteins, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of increasing the amount or concentration of one or more lacrimal proteins, the nicotinic acetylcholine receptor agonist is nicotine. In another embodiment of any of the aforementioned embodiments of increasing the amount or concentration of one or more lacrimal proteins, the nicotinic acetylcholine receptor agonist is cytisine. In another embodiment of any of the aforementioned embodiments of increasing the amount or concentration of one or more lacrimal proteins, the nicotinic acetylcholine receptor agonist is epibatidine. In another embodiment of any of the aforementioned embodiments of increasing the amount or concentration of one or more lacrimal proteins, the nicotinic acetylcholine receptor agonist is varenicline. In another embodiment of any of the aforementioned embodiments of increasing the amount or concentration of one or more lacrimal proteins, the nicotinic acetylcholine receptor agonist is tebanicline. In another embodiment of any of the aforementioned embodiments of increasing the amount or concentration of one or more lacrimal proteins, the nicotinic acetylcholine receptor agonist is DBO-83. In another embodiment of any of the aforementioned embodiments of increasing the amount or concentration of one or more lacrimal proteins, the nicotinic acetylcholine receptor agonist is CC4. In another embodiment of any of the aforementioned embodiments of increasing the amount or concentration of one or more lacrimal proteins, the nicotinic acetylcholine receptor agonist is ABT-418. In another embodiment of any of the aforementioned embodiments of increasing the amount or concentration of one or more lacrimal proteins, the nicotinic acetylcholine receptor agonist is ABT-366833. In another embodiment of any of the aforementioned embodiments of increasing the amount or concentration of one or more lacrimal proteins, the nicotinic acetylcholine receptor agonist is ABT-202. In another embodiment of any of the aforementioned embodiments of increasing the amount or concentration of one or more lacrimal proteins, the nicotinic acetylcholine receptor agonist is ABT-894. In another embodiment of any of the aforementioned embodiments of increasing the amount or concentration of one or more lacrimal proteins, the nicotinic acetylcholine receptor agonist is SIB-1663. In another embodiment of any of the aforementioned embodiments of increasing the amount or concentration of one or more lacrimal proteins, the nicotinic acetylcholine receptor agonist is GTS-21. In another embodiment of any of the aforementioned embodiments of increasing the amount or concentration of one or more lacrimal proteins, the nicotinic acetylcholine receptor agonist is PHA-543613. In another embodiment of any of the aforementioned embodiments of increasing the amount or concentration of one or more lacrimal proteins, the nicotinic acetylcholine receptor agonist is PNU-282987. In another embodiment of any of the aforementioned embodiments of increasing the amount or concentration of one or more lacrimal proteins, the nicotinic acetylcholine receptor agonist is LY-2087101. In another embodiment of any of the aforementioned embodiments of increasing the amount or concentration of one or more lacrimal proteins, the nicotinic acetylcholine receptor agonist is A85380. In another embodiment of any of the aforementioned embodiments of increasing the amount or concentration of one or more lacrimal proteins, the nicotinic acetylcholine receptor agonist is 5-I-A85380.

In a further embodiment of any of the aforementioned embodiments of increasing the amount or concentration of one or more lacrimal proteins, the nicotinic acetylcholine receptor agonist is selected from a compound disclosed in WO 2008/057938, WO 2009/111550, WO 2010/028011, or WO 2010/028033.

In another embodiment of any of the aforementioned embodiments of increasing the amount or concentration of one or more lacrimal proteins, at least 1 microgram of the nicotinic acetylcholine receptor agonist is administered into the nasal cavity. In another embodiment of any of the aforementioned embodiments of increasing the amount or concentration of one or more lacrimal proteins, at least 5 micrograms of the nicotinic acetylcholine receptor agonist is administered into the nasal cavity. In another embodiment of any of the aforementioned embodiments of increasing the amount or concentration of one or more lacrimal proteins, at least 10 micrograms of the nicotinic acetylcholine receptor agonist is administered into the nasal cavity. In another embodiment of any of the aforementioned embodiments of increasing the amount or concentration of one or more lacrimal proteins, at least 25 micrograms of the nicotinic acetylcholine receptor agonist is administered into the nasal cavity. In another embodiment of any of the aforementioned embodiments of increasing the amount or concentration of one or more lacrimal proteins, at least 50 micrograms of the nicotinic acetylcholine receptor agonist is administered into the nasal cavity. In another embodiment of any of the aforementioned embodiments of increasing the amount or concentration of one or more lacrimal proteins, at least 100 micrograms of the nicotinic acetylcholine receptor agonist is administered into the nasal cavity. In another embodiment of any of the aforementioned embodiments of increasing the amount or concentration of one or more lacrimal proteins, at least 250 micrograms of the nicotinic acetylcholine receptor agonist is administered into the nasal cavity. In another embodiment of any of the aforementioned embodiments of increasing the amount or concentration of one or more lacrimal proteins, at least 500 micrograms of the nicotinic acetylcholine receptor agonist is administered into the nasal cavity. In another embodiment of any of the aforementioned embodiments of increasing the amount or concentration of one or more lacrimal proteins, at least 750 micrograms of the nicotinic acetylcholine receptor agonist is administered into the nasal cavity. In another embodiment of any of the aforementioned embodiments of increasing the amount or concentration of one or more lacrimal proteins, at least 1000 micrograms of the nicotinic acetylcholine receptor agonist is administered into the nasal cavity. In another embodiment of any of the aforementioned embodiments of increasing the amount or concentration of one or more lacrimal proteins, between 1 microgram and 1000 micrograms of the nicotinic acetylcholine receptor agonist is administered into the nasal cavity. In another embodiment of any of the aforementioned embodiments of increasing the amount or concentration of one or more lacrimal proteins, between 5 micrograms and 1000 micrograms of the nicotinic acetylcholine receptor agonist is administered into the nasal cavity. In another embodiment of any of the aforementioned embodiments of increasing the amount or concentration of one or more lacrimal proteins, between 5 micrograms and 100 micrograms of the nicotinic acetylcholine receptor agonist is administered into the nasal cavity. In another embodiment of any of the aforementioned embodiments of increasing the amount or concentration of one or more lacrimal proteins, between 5 micrograms and 50 micrograms of the nicotinic acetylcholine receptor agonist is administered into the nasal cavity. In another embodiment of any of the aforementioned embodiments of increasing the amount or concentration of one or more lacrimal proteins, between 10 micrograms and 50 micrograms of the nicotinic acetylcholine receptor agonist is administered into the nasal cavity. In another embodiment of any of the aforementioned embodiments of increasing the amount or concentration of one or more lacrimal proteins, between 25 micrograms and 1000 micrograms of the nicotinic acetylcholine receptor agonist is administered into the nasal cavity. In another embodiment of any of the aforementioned embodiments of increasing the amount or concentration of one or more lacrimal proteins, between 50 micrograms and 1000 micrograms of the nicotinic acetylcholine receptor agonist is administered into the nasal cavity. In another embodiment of any of the aforementioned embodiments of increasing the amount or concentration of one or more lacrimal proteins, between 100 micrograms and 1000 micrograms of the nicotinic acetylcholine receptor agonist is administered into the nasal cavity. In another embodiment of any of the aforementioned embodiments of increasing the amount or concentration of one or more lacrimal proteins, between 100 micrograms and 750 micrograms of the nicotinic acetylcholine receptor agonist is administered into the nasal cavity. In another embodiment of any of the aforementioned embodiments of increasing the amount or concentration of one or more lacrimal proteins, between 150 micrograms and 750 micrograms of the nicotinic acetylcholine receptor agonist is administered into the nasal cavity. In another embodiment of any of the aforementioned embodiments of increasing the amount or concentration of one or more lacrimal proteins, between 150 micrograms and 600 micrograms of the nicotinic acetylcholine receptor agonist is administered into the nasal cavity.

In another embodiment of any of the aforementioned embodiments of increasing the amount or concentration of one or more lacrimal proteins, the nicotinic acetylcholine receptor agonist is administered once daily. In another embodiment of any of the aforementioned embodiments of increasing the amount or concentration of one or more lacrimal proteins, the nicotinic acetylcholine receptor agonist is administered at least once daily. In another embodiment of any of the aforementioned embodiments of increasing the amount or concentration of one or more lacrimal proteins, the nicotinic acetylcholine receptor agonist is administered twice daily. In another embodiment of any of the aforementioned embodiments of increasing the amount or concentration of one or more lacrimal proteins, the nicotinic acetylcholine receptor agonist is administered at least twice daily. In another embodiment of any of the aforementioned embodiments of increasing the amount or concentration of one or more lacrimal proteins, the nicotinic acetylcholine receptor agonist is administered three times daily. In another embodiment of any of the aforementioned embodiments of increasing the amount or concentration of one or more lacrimal proteins, the nicotinic acetylcholine receptor agonist is administered at least three times daily. In another embodiment of any of the aforementioned embodiments of increasing the amount or concentration of one or more lacrimal proteins, the nicotinic acetylcholine receptor agonist is administered for one day. In another embodiment of any of the aforementioned embodiments of increasing the amount or concentration of one or more lacrimal proteins, the nicotinic acetylcholine receptor agonist is administered for at least two days. In another embodiment of any of the aforementioned embodiments of increasing the amount or concentration of one or more lacrimal proteins, the nicotinic acetylcholine receptor agonist is administered for at least three days. In another embodiment of any of the aforementioned embodiments of increasing the amount or concentration of one or more lacrimal proteins, the nicotinic acetylcholine receptor agonist is administered for at least four days. In another embodiment of any of the aforementioned embodiments of increasing the amount or concentration of one or more lacrimal proteins, the nicotinic acetylcholine receptor agonist is administered for at least five days. In another embodiment of any of the aforementioned embodiments of increasing the amount or concentration of one or more lacrimal proteins, the nicotinic acetylcholine receptor agonist is administered for at least seven days. In another embodiment of any of the aforementioned embodiments of increasing the amount or concentration of one or more lacrimal proteins, the nicotinic acetylcholine receptor agonist is administered for at least ten days. In another embodiment of any of the aforementioned embodiments of increasing the amount or concentration of one or more lacrimal proteins, the nicotinic acetylcholine receptor agonist is administered for at least fourteen days. In another embodiment of any of the aforementioned embodiments of increasing the amount or concentration of one or more lacrimal proteins, the nicotinic acetylcholine receptor agonist is administered for at least twenty one days. In another embodiment of any of the aforementioned embodiments of increasing the amount or concentration of one or more lacrimal proteins, the nicotinic acetylcholine receptor agonist is administered for at least thirty days.

In another embodiment of any of the aforementioned embodiments of increasing the amount or concentration of one or more lacrimal proteins, the nicotinic acetylcholine receptor agonist is administered in alternating nostrils.

In another embodiment of any of the aforementioned embodiments of increasing the amount or concentration of one or more lacrimal proteins, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of increasing the amount or concentration of one or more lacrimal proteins, the nicotinic acetylcholine receptor agonist is administered into the nasal cavity as a liquid. In another embodiment of any of the aforementioned embodiments of increasing the amount or concentration of one or more lacrimal proteins, the nicotinic acetylcholine receptor agonist is administered into the nasal cavity as a suspension. In another embodiment of any of the aforementioned embodiments of increasing the amount or concentration of one or more lacrimal proteins, the nicotinic acetylcholine receptor agonist is administered into the nasal cavity as an aerosol. In another embodiment of any of the aforementioned embodiments of increasing the amount or concentration of one or more lacrimal proteins, the nicotinic acetylcholine receptor agonist is administered into the nasal cavity as a gel. In another embodiment of any of the aforementioned embodiments of increasing the amount or concentration of one or more lacrimal proteins, the nicotinic acetylcholine receptor agonist is administered into the nasal cavity as an ointment. In another embodiment of any of the aforementioned embodiments of increasing the amount or concentration of one or more lacrimal proteins, the nicotinic acetylcholine receptor agonist is administered into the nasal cavity as a dry powder. In another embodiment of any of the aforementioned embodiments of increasing the amount or concentration of one or more lacrimal proteins, the nicotinic acetylcholine receptor agonist is administered into the nasal cavity as a cream. In another embodiment of any of the aforementioned embodiments of increasing the amount or concentration of one or more lacrimal proteins, the nicotinic acetylcholine receptor agonist is administered into the nasal cavity as a paste. In another embodiment of any of the aforementioned embodiments of increasing the amount or concentration of one or more lacrimal proteins, the nicotinic acetylcholine receptor agonist is administered into the nasal cavity as a lotion. In another embodiment of any of the aforementioned embodiments of increasing the amount or concentration of one or more lacrimal proteins, the nicotinic acetylcholine receptor agonist is administered into the nasal cavity as a balm.

In another embodiment of any of the aforementioned embodiments of increasing the amount or concentration of one or more lacrimal proteins, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of increasing the amount or concentration of one or more lacrimal proteins, the nicotinic acetylcholine receptor agonist is administered into the nasal cavity by a syringe. In another embodiment of any of the aforementioned embodiments of increasing the amount or concentration of one or more lacrimal proteins, the nicotinic acetylcholine receptor agonist is administered into the nasal cavity by a dropper. In another embodiment of any of the aforementioned embodiments of increasing the amount or concentration of one or more lacrimal proteins, the nicotinic acetylcholine receptor agonist is administered into the nasal cavity by a bottle nebulizer. In another embodiment of any of the aforementioned embodiments of increasing the amount or concentration of one or more lacrimal proteins, the nicotinic acetylcholine receptor agonist is administered into the nasal cavity by an atomization pump. In another embodiment of any of the aforementioned embodiments of increasing the amount or concentration of one or more lacrimal proteins, the nicotinic acetylcholine receptor agonist is administered into the nasal cavity by an inhaler. In another embodiment of any of the aforementioned embodiments of increasing the amount or concentration of one or more lacrimal proteins, the nicotinic acetylcholine receptor agonist is administered into the nasal cavity by a powder spray device. In another embodiment of any of the aforementioned embodiments of increasing the amount or concentration of one or more lacrimal proteins, the nicotinic acetylcholine receptor agonist is administered into the nasal cavity by a vaporizer. In another embodiment of any of the aforementioned embodiments of increasing the amount or concentration of one or more lacrimal proteins, the nicotinic acetylcholine receptor agonist is administered into the nasal cavity by a patch. In another embodiment of any of the aforementioned embodiments of increasing the amount or concentration of one or more lacrimal proteins, the nicotinic acetylcholine receptor agonist is administered into the nasal cavity by a medicated stick. In another embodiment of any of the aforementioned embodiments of increasing the amount or concentration of one or more lacrimal proteins, the nicotinic acetylcholine receptor agonist is administered into the nasal cavity by a pipette. In another embodiment of any of the aforementioned embodiments of increasing the amount or concentration of one or more lacrimal proteins, the nicotinic acetylcholine receptor agonist is administered into the nasal cavity by a jet of liquid.

In another embodiment of any of the aforementioned embodiments of increasing the amount or concentration of one or more lacrimal proteins, the trigeminal nerve is activated. In a further embodiment of increasing the amount or concentration of one or more lacrimal proteins, the anterior ethmoidal nerve is activated. In another embodiment of any of the aforementioned embodiments of increasing the amount or concentration of one or more lacrimal proteins, the nasolacrimal reflex is activated.

Enhancing Tear Clearance

Provided herein, in some embodiments, is a method of enhancing tear clearance in a subject. In some embodiments, is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and does not cross the blood-brain barrier in a pharmacologically relevant concentration. In some embodiments is method of enhancing tear clearance, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to at least one of the peripheral nicotinic acetylcholine receptor subtypes selected from alpha3beta4, alpha4beta2, and alpha7. In some embodiments is method of enhancing tear clearance, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha3beta4. In some embodiments is method of enhancing tear clearance, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha4beta2. In some embodiments is method of enhancing tear clearance, comprising the local administration of a therapeutically effective amount of a nicotinic acetylcholine receptor agonist into the nasal cavity of an individual in need thereof, wherein the agonist does not cross the blood-brain barrier in a pharmacologically relevant concentration and selectively binds to the peripheral nicotinic acetylcholine receptor subtype alpha7. In some embodiments is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and is administered in an amount that is not systemically bioavailable. In some embodiments is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired psychoactive side effects. In some embodiments is a method of enhancing tear clearance, comprising the local administration of a therapeutically effective amount of a nicotinic acetylcholine receptor agonist into the nasal cavity of an individual in need thereof, wherein the agonist selectively binds to the peripheral nicotinic acetylcholine receptor and in an amount that does not result in undesired systemic side effects. In some embodiments is a method of enhancing tear clearance, further comprising the local administration of one or more substances that prevent or facilitate the recovery of the nicotinic acetylcholine receptor from the desensitized state. In some embodiments is a method of enhancing tear clearance, further comprising the local administration of one or more substances that prevent the entry or reduce the entry of the nicotinic acetylcholine receptor into the desensitized state, or facilitate the recovery of the nicotinic acetylcholine receptor from the desensitized state. In some embodiments is a method of enhancing tear clearance, further comprising the local administration of one or more substances that prevent or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of enhancing tear clearance, further comprising the local administration of one or more substances that prevent the entry or reduce the entry of the nicotinic acetylcholine receptor into the desensitized state, or facilitate the recovery of the nicotinic acetylcholine receptor from the desensitized state selected from protein kinase C (PKC) or factors that upregulate or up-modulate PKC, cAMP-dependent protein kinase (PKA) or factors that upregulate or up-modulate PKA, and calcineurin inhibitors. In some embodiments is a method of enhancing tear clearance, further comprising the local administration of protein kinase C (PKC) or factors that upregulate or up-modulate PKC. In some embodiments is a method of enhancing tear clearance, further comprising the local administration of cAMP-dependent protein kinase (PKA) or factors that upregulate or up-modulate PKA. In some embodiments is a method of enhancing tear clearance, further comprising the local administration of a calcineurin inhibitor. In some embodiments is a method of enhancing tear clearance, further comprising the local administration of a calcineurin inhibitor, wherein the calcineurin inhibitor is selected from cyclosporine, pimecrolimus, and tacrolimus. In some embodiments is a method of enhancing tear clearance, further comprising the local administration of cyclosporine. In some embodiments is a method of enhancing tear clearance, further comprising the local administration of pimecrolimus. In some embodiments is a method of enhancing tear clearance, further comprising the local administration of tacrolimus.

In a further embodiment of any of the aforementioned embodiments of enhancing tear clearance, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In another embodiment of any of the aforementioned embodiments of enhancing tear clearance, the nicotinic acetylcholine receptor agonist is nicotine. In another embodiment of any of the aforementioned embodiments of enhancing tear clearance, the nicotinic acetylcholine receptor agonist is cytisine. In another embodiment of any of the aforementioned embodiments of enhancing tear clearance, the nicotinic acetylcholine receptor agonist is epibatidine. In another embodiment of any of the aforementioned embodiments of enhancing tear clearance, the nicotinic acetylcholine receptor agonist is varenicline. In another embodiment of any of the aforementioned embodiments of enhancing tear clearance, the nicotinic acetylcholine receptor agonist is tebanicline. In another embodiment of any of the aforementioned embodiments of enhancing tear clearance, the nicotinic acetylcholine receptor agonist is DBO-83. In another embodiment of any of the aforementioned embodiments of enhancing tear clearance, the nicotinic acetylcholine receptor agonist is CC4. In another embodiment of any of the aforementioned embodiments of enhancing tear clearance, the nicotinic acetylcholine receptor agonist is ABT-418. In another embodiment of any of the aforementioned embodiments of enhancing tear clearance, the nicotinic acetylcholine receptor agonist is ABT-366833. In another embodiment of any of the aforementioned embodiments of enhancing tear clearance, the nicotinic acetylcholine receptor agonist is ABT-202. In another embodiment of any of the aforementioned embodiments of enhancing tear clearance, the nicotinic acetylcholine receptor agonist is ABT-894. In another embodiment of any of the aforementioned embodiments of enhancing tear clearance, the nicotinic acetylcholine receptor agonist is SIB-1663. In another embodiment of any of the aforementioned embodiments of enhancing tear clearance, the nicotinic acetylcholine receptor agonist is GTS-21. In another embodiment of any of the aforementioned embodiments of enhancing tear clearance, the nicotinic acetylcholine receptor agonist is PHA-543613. In another embodiment of any of the aforementioned embodiments of enhancing tear clearance, the nicotinic acetylcholine receptor agonist is PNU-282987. In another embodiment of any of the aforementioned embodiments of enhancing tear clearance, the nicotinic acetylcholine receptor agonist is LY-2087101. In another embodiment of any of the aforementioned embodiments of enhancing tear clearance, the nicotinic acetylcholine receptor agonist is A85380. In another embodiment of any of the aforementioned embodiments of enhancing tear clearance, the nicotinic acetylcholine receptor agonist is 5-I-A85380.

In a further embodiment of any of the aforementioned embodiments of enhancing tear clearance, the nicotinic acetylcholine receptor agonist is selected from a compound disclosed in WO 2008/057938, WO 2009/111550, WO 2010/028011, or WO 2010/028033.

In another embodiment of any of the aforementioned embodiments of enhancing tear clearance, at least 1 microgram of the nicotinic acetylcholine receptor agonist is administered into the nasal cavity. In another embodiment of any of the aforementioned embodiments of enhancing tear clearance, at least 5 micrograms of the nicotinic acetylcholine receptor agonist is administered into the nasal cavity. In another embodiment of any of the aforementioned embodiments of enhancing tear clearance, at least 10 micrograms of the nicotinic acetylcholine receptor agonist is administered into the nasal cavity. In another embodiment of any of the aforementioned embodiments of enhancing tear clearance, at least 25 micrograms of the nicotinic acetylcholine receptor agonist is administered into the nasal cavity. In another embodiment of any of the aforementioned embodiments of enhancing tear clearance, at least 50 micrograms of the nicotinic acetylcholine receptor agonist is administered into the nasal cavity. In another embodiment of any of the aforementioned embodiments of enhancing tear clearance, at least 100 micrograms of the nicotinic acetylcholine receptor agonist is administered into the nasal cavity. In another embodiment of any of the aforementioned embodiments of enhancing tear clearance, at least 250 micrograms of the nicotinic acetylcholine receptor agonist is administered into the nasal cavity. In another embodiment of any of the aforementioned embodiments of enhancing tear clearance, at least 500 micrograms of the nicotinic acetylcholine receptor agonist is administered into the nasal cavity. In another embodiment of any of the aforementioned embodiments of enhancing tear clearance, at least 750 micrograms of the nicotinic acetylcholine receptor agonist is administered into the nasal cavity. In another embodiment of any of the aforementioned embodiments of enhancing tear clearance, at least 1000 micrograms of the nicotinic acetylcholine receptor agonist is administered into the nasal cavity. In another embodiment of any of the aforementioned embodiments of enhancing tear clearance, between 1 microgram and 1000 micrograms of the nicotinic acetylcholine receptor agonist is administered into the nasal cavity. In another embodiment of any of the aforementioned embodiments of enhancing tear clearance, between 5 micrograms and 1000 micrograms of the nicotinic acetylcholine receptor agonist is administered into the nasal cavity. In another embodiment of any of the aforementioned embodiments of enhancing tear clearance, between 5 micrograms and 100 micrograms of the nicotinic acetylcholine receptor agonist is administered into the nasal cavity. In another embodiment of any of the aforementioned embodiments of enhancing tear clearance, between 5 micrograms and 50 micrograms of the nicotinic acetylcholine receptor agonist is administered into the nasal cavity. In another embodiment of any of the aforementioned embodiments of enhancing tear clearance, between 10 micrograms and 50 micrograms of the nicotinic acetylcholine receptor agonist is administered into the nasal cavity. In another embodiment of any of the aforementioned embodiments of enhancing tear clearance, between 25 micrograms and 1000 micrograms of the nicotinic acetylcholine receptor agonist is administered into the nasal cavity. In another embodiment of any of the aforementioned embodiments of enhancing tear clearance, between 50 micrograms and 1000 micrograms of the nicotinic acetylcholine receptor agonist is administered into the nasal cavity. In another embodiment of any of the aforementioned embodiments of enhancing tear clearance, between 100 micrograms and 1000 micrograms of the nicotinic acetylcholine receptor agonist is administered into the nasal cavity. In another embodiment of any of the aforementioned embodiments of enhancing tear clearance, between 100 micrograms and 750 micrograms of the nicotinic acetylcholine receptor agonist is administered into the nasal cavity. In another embodiment of any of the aforementioned embodiments of enhancing tear clearance, between 150 micrograms and 750 micrograms of the nicotinic acetylcholine receptor agonist is administered into the nasal cavity. In another embodiment of any of the aforementioned embodiments of enhancing tear clearance, between 150 micrograms and 600 micrograms of the nicotinic acetylcholine receptor agonist is administered into the nasal cavity.

In another embodiment of any of the aforementioned embodiments of enhancing tear clearance, the nicotinic acetylcholine receptor agonist is administered once daily. In another embodiment of any of the aforementioned embodiments of enhancing tear clearance, the nicotinic acetylcholine receptor agonist is administered at least once daily. In another embodiment of any of the aforementioned embodiments of enhancing tear clearance, the nicotinic acetylcholine receptor agonist is administered twice daily. In another embodiment of any of the aforementioned embodiments of enhancing tear clearance, the nicotinic acetylcholine receptor agonist is administered at least twice daily. In another embodiment of any of the aforementioned embodiments of enhancing tear clearance, the nicotinic acetylcholine receptor agonist is administered three times daily. In another embodiment of any of the aforementioned embodiments of enhancing tear clearance, the nicotinic acetylcholine receptor agonist is administered at least three times daily. In another embodiment of any of the aforementioned embodiments of enhancing tear clearance, the nicotinic acetylcholine receptor agonist is administered for one day. In another embodiment of any of the aforementioned embodiments of enhancing tear clearance, the nicotinic acetylcholine receptor agonist is administered for at least two days. In another embodiment of any of the aforementioned embodiments of enhancing tear clearance, the nicotinic acetylcholine receptor agonist is administered for at least three days. In another embodiment of any of the aforementioned embodiments of enhancing tear clearance, the nicotinic acetylcholine receptor agonist is administered for at least four days. In another embodiment of any of the aforementioned embodiments of enhancing tear clearance, the nicotinic acetylcholine receptor agonist is administered for at least five days. In another embodiment of any of the aforementioned embodiments of enhancing tear clearance, the nicotinic acetylcholine receptor agonist is administered for at least seven days. In another embodiment of any of the aforementioned embodiments of enhancing tear clearance, the nicotinic acetylcholine receptor agonist is administered for at least ten days. In another embodiment of any of the aforementioned embodiments of enhancing tear clearance, the nicotinic acetylcholine receptor agonist is administered for at least fourteen days. In another embodiment of any of the aforementioned embodiments of enhancing tear clearance, the nicotinic acetylcholine receptor agonist is administered for at least twenty one days. In another embodiment of any of the aforementioned embodiments of enhancing tear clearance, the nicotinic acetylcholine receptor agonist is administered for at least thirty days.

In another embodiment of any of the aforementioned embodiments of enhancing tear clearance, the nicotinic acetylcholine receptor agonist is administered in alternating nostrils.

In another embodiment of any of the aforementioned embodiments of enhancing tear clearance, the nicotinic acetylcholine receptor agonist is administered into the nasal cavity as a liquid, suspension, aerosol, gel, ointment, dry powder, cream, paste, lotion, or balm. In another embodiment of any of the aforementioned embodiments of enhancing tear clearance, the nicotinic acetylcholine receptor agonist is administered into the nasal cavity as a liquid. In another embodiment of any of the aforementioned embodiments of enhancing tear clearance, the nicotinic acetylcholine receptor agonist is administered into the nasal cavity as a suspension. In another embodiment of any of the aforementioned embodiments of enhancing tear clearance, the nicotinic acetylcholine receptor agonist is administered into the nasal cavity as an aerosol. In another embodiment of any of the aforementioned embodiments of enhancing tear clearance, the nicotinic acetylcholine receptor agonist is administered into the nasal cavity as a gel. In another embodiment of any of the aforementioned embodiments of enhancing tear clearance, the nicotinic acetylcholine receptor agonist is administered into the nasal cavity as an ointment. In another embodiment of any of the aforementioned embodiments of enhancing tear clearance, the nicotinic acetylcholine receptor agonist is administered into the nasal cavity as a dry powder. In another embodiment of any of the aforementioned embodiments of enhancing tear clearance, the nicotinic acetylcholine receptor agonist is administered into the nasal cavity as a cream. In another embodiment of any of the aforementioned embodiments of enhancing tear clearance, the nicotinic acetylcholine receptor agonist is administered into the nasal cavity as a paste. In another embodiment of any of the aforementioned embodiments of enhancing tear clearance, the nicotinic acetylcholine receptor agonist is administered into the nasal cavity as a lotion. In another embodiment of any of the aforementioned embodiments of enhancing tear clearance, the nicotinic acetylcholine receptor agonist is administered into the nasal cavity as a balm.

In another embodiment of any of the aforementioned embodiments of enhancing tear clearance, the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In another embodiment of any of the aforementioned embodiments of enhancing tear clearance, the nicotinic acetylcholine receptor agonist is administered into the nasal cavity by a syringe. In another embodiment of any of the aforementioned embodiments of enhancing tear clearance, the nicotinic acetylcholine receptor agonist is administered into the nasal cavity by a dropper. In another embodiment of any of the aforementioned embodiments of enhancing tear clearance, the nicotinic acetylcholine receptor agonist is administered into the nasal cavity by a bottle nebulizer. In another embodiment of any of the aforementioned embodiments of enhancing tear clearance, the nicotinic acetylcholine receptor agonist is administered into the nasal cavity by an atomization pump. In another embodiment of any of the aforementioned embodiments of enhancing tear clearance, the nicotinic acetylcholine receptor agonist is administered into the nasal cavity by an inhaler. In another embodiment of any of the aforementioned embodiments of enhancing tear clearance, the nicotinic acetylcholine receptor agonist is administered into the nasal cavity by a powder spray device. In another embodiment of any of the aforementioned embodiments of enhancing tear clearance, the nicotinic acetylcholine receptor agonist is administered into the nasal cavity by a vaporizer. In another embodiment of any of the aforementioned embodiments of enhancing tear clearance, the nicotinic acetylcholine receptor agonist is administered into the nasal cavity by a patch. In another embodiment of any of the aforementioned embodiments of enhancing tear clearance, the nicotinic acetylcholine receptor agonist is administered into the nasal cavity by a medicated stick. In another embodiment of any of the aforementioned embodiments of enhancing tear clearance, the nicotinic acetylcholine receptor agonist is administered into the nasal cavity by a pipette. In another embodiment of any of the aforementioned embodiments of enhancing tear clearance, the nicotinic acetylcholine receptor agonist is administered into the nasal cavity by a jet of liquid.

In another embodiment of any of the aforementioned embodiments of enhancing tear clearance, the trigeminal nerve is activated. In a further embodiment of enhancing tear clearance, the anterior ethmoidal nerve is activated. In another embodiment of any of the aforementioned embodiments of enhancing tear clearance, the nasolacrimal reflex is activated.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the pharmaceutical formulation comprising a nicotinic acetylcholine receptor agonist as disclosed herein required to provide a clinically significant decrease in disease symptoms. An appropriate "effective" amount in any individual case may be determined using techniques, such as a dose escalation study.

The terms "individual", "subject", and "patient" encompass mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

A "tissue" comprises two or more cells. The two or more cells may have a similar function and/or function. The tissue may be a connective tissue, epithelial tissue, muscular tissue, or nervous tissue. Alternatively, the tissue is a bone, tendon (both referred to as musculoskeletal grafts), cornea, skin, heart valve, or vein.

An "organ" comprises two or more tissues. The two or more tissues may perform a specific function or group of functions. In some instances, the organ is a lung, mouth, nose, parathyroid gland, pineal gland, pituitary gland, carotid body, salivary gland, skin, gall bladder, pancreas, small intestine, stomach, spleen, spinal cord, thymus, thyroid gland, trachea, uterus, or vermiform appendix. Alternatively, the organ is an adrenal gland, appendix, brain, bladder, kidney, intestine, large intestine, small intestine, liver, heart, or muscle.

The term "nicotinic acetylcholine receptor agonist" encompasses a full agonist or a partial agonist of the nicotinic acetylcholine receptor.

The terms "treat," "treating" or "treatment," as used herein, include alleviating, abating or ameliorating at least one symptom of a disease or condition, preventing additional symptoms, preventing progression of the condition, inhibiting the disease or condition, e.g., arresting the development of the disease or condition, relieving the disease or condition, causing regression of the disease or condition, relieving a condition caused by the disease or condition, or stopping the symptoms of the disease or condition. In one embodiment, treatment is prophylactic treatment. In another embodiment, treatment refers to therapeutic treatment.

The term "does not cross the blood-brain barrier in a pharmacologically relevant concentration" as used herein, refers to an insufficient amount of a nicotinic acetylcholine receptor agonist as disclosed herein passing through the blood-brain barrier to produce a pharmacological response.

The term "undesired psychoactive side effects" as used herein, refers to unintended effects in the brain including, but not limited to, anxiety, depression, hallucination, euphoria, addiction, sleep disorder/disturbances, insomnia, abnormal dreams, and nightmares.

The term "undesired systemic side effects" as used herein, refers to unintended effects in the body including, but not limited to, abdominal pain, vomiting, nausea, constipation, diarrhea, flatulence, dyspepsia, and dry mouth.

The term "nicotinic acetylcholine receptor agonist formulated to prevent desensitization" as used herein, refers to a formulation that does not result in tolerance, dependence, withdrawal, or loss of sensitivity to the effect of the nicotinic acetylcholine receptor agonist.

The term "environmentally challenging conditions" as used herein, refers to external conditions including naturally and man-made conditions. Naturally occurring environmentally challenging conditions include, but are not limited to, exposure to smoke, wind, and dry climates. Man-made environmentally challenging conditions include, but are not limited to, exposure to pollution from automobiles, factories, and airplanes, as well as homes/offices with low humidity, high airflow or poor air quality. In some embodiments, "environmentally challenging conditions" refer to controlled challenge environments commonly used for dry eye clinical trials.

The term "ocular discomfort" includes, but is not limited to, the symptoms of dry eye disease, such as itchiness, dryness, photophobia, blurriness, pain, sticky feeling, burning, stinging, and foreign body sensation. In some embodiments, ocular discomfort is associated with blepharitis, meibomian gland dysfunction, allergic conjunctivitis, ocular surface toxicity and irritation, lacrimal drainage problems, or eyelid disorders.

The term "soft drug" as used herein, refers to a drug substance that is rapidly metabolized into an inactive form immediately after achieving the therapeutic effect.

Nicotinic Acetylcholine Receptor Agonists

The methods described herein comprise the local administration of a therapeutically effective amount of a nicotinic acetylcholine receptor agonist into the nasal cavity of an individual in need thereof. In some embodiments of the methods described herein, the nicotinic acetylcholine receptor agonist is a full agonist. In some embodiments of the methods described herein, the nicotinic acetylcholine receptor agonist is a partial agonist. In some embodiments of the methods described herein, the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In some embodiments of the methods described herein, the nicotinic acetylcholine receptor agonist is nicotine. In some embodiments of the methods described herein, the nicotinic acetylcholine receptor agonist is cytisine. In some embodiments of the methods described herein, the nicotinic acetylcholine receptor agonist is epibatidine. In some embodiments of the methods described herein, the nicotinic acetylcholine receptor agonist is varenicline. In some embodiments of the methods described herein, the nicotinic acetylcholine receptor agonist is tebanicline. In some embodiments of the methods described herein, the nicotinic acetylcholine receptor agonist is DBO-83. In some embodiments of the methods described herein, the nicotinic acetylcholine receptor agonist is CC4. In some embodiments of the methods described herein, the nicotinic acetylcholine receptor agonist is ABT-418. In some embodiments of the methods described herein, the nicotinic acetylcholine receptor agonist is ABT-366833. In some embodiments of the methods described herein, the nicotinic acetylcholine receptor agonist is ABT-202. In some embodiments of the methods described herein, the nicotinic acetylcholine receptor agonist is ABT-894. In some embodiments of the methods described herein, the nicotinic acetylcholine receptor agonist is SIB-1663. In some embodiments of the methods described herein, the nicotinic acetylcholine receptor agonist is GTS-21. In some embodiments of the methods described herein, the nicotinic acetylcholine receptor agonist is PHA-543613. In some embodiments of the methods described herein, the nicotinic acetylcholine receptor agonist is PNU-282987. In some embodiments of the methods described herein, the nicotinic acetylcholine receptor agonist is LY-2087101. In some embodiments of the methods described herein, the nicotinic acetylcholine receptor agonist is A85380. In some embodiments of the methods described herein, the nicotinic acetylcholine receptor agonist is 5-I-A85380. In some embodiments of the methods described herein, the nicotinic acetylcholine receptor agonist is selected from a compound disclosed in WO 2008/057938, WO 2009/111550, WO 2010/028011, or WO 2010/028033.

In some embodiments of the methods described herein, the nicotinic acetylcholine receptor agonist is a soft drug.

In some embodiments of the methods described herein is a nicotinic acetylcholine receptor agonist having the structure:

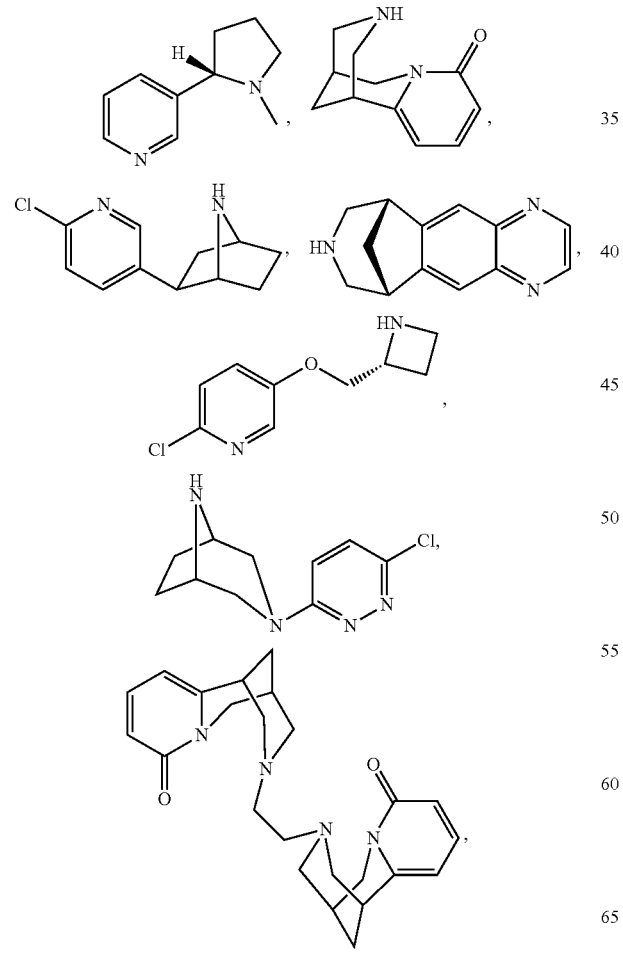

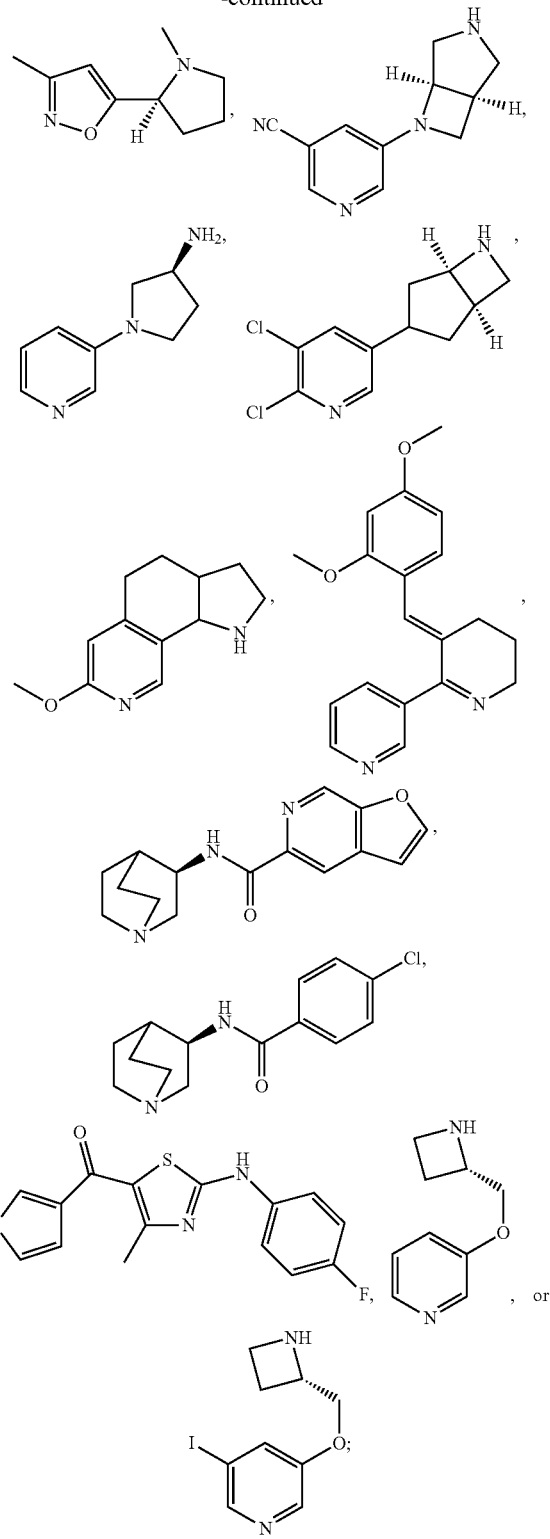

or a pharmaceutically acceptable salt thereof.

Intranasal Route of Administration

The methods described herein comprise the local administration of a therapeutically effective amount of a nicotinic acetylcholine receptor agonist into the nasal cavity of an individual in need thereof. In some embodiments, the methods described herein comprise the local administration of a therapeutically effective amount of a nicotinic acetylcholine receptor agonist into the nasal cavity of an individual in need thereof, wherein the nicotinic acetylcholine receptor agonist is administered into the nasal cavity as a liquid, suspension, aerosol, gel, ointment, dry powder, cream, paste, lotion, or balm. In some embodiments of the methods described herein, the nicotinic acetylcholine receptor agonist is administered into the nasal cavity as a liquid. In some embodiments of the methods described herein, the nicotinic acetylcholine receptor agonist is administered into the nasal cavity as a suspension. In some embodiments of the methods described herein, the nicotinic acetylcholine receptor agonist is administered into the nasal cavity as an aerosol. In some embodiments of the methods described herein, the nicotinic acetylcholine receptor agonist is administered into the nasal cavity as a gel. In some embodiments of the methods described herein, the nicotinic acetylcholine receptor agonist is administered into the nasal cavity as an ointment. In some embodiments of the methods described herein, the nicotinic acetylcholine receptor agonist is administered into the nasal cavity as a dry powder. In some embodiments of the methods described herein, the nicotinic acetylcholine receptor agonist is administered into the nasal cavity as a cream. In some embodiments of the methods described herein, the nicotinic acetylcholine receptor agonist is administered into the nasal cavity as a paste. In some embodiments of the methods described herein, the nicotinic acetylcholine receptor agonist is administered into the nasal cavity as a lotion. In some embodiments of the methods described herein, the nicotinic acetylcholine receptor agonist is administered into the nasal cavity as a balm.

In some embodiments, the methods described herein comprise the local administration of a therapeutically effective amount of a nicotinic acetylcholine receptor agonist into the nasal cavity of an individual in need thereof, wherein the nicotinic acetylcholine receptor agonist is administered into the nasal cavity by a syringe, dropper, bottle nebulizer, atomization pump, inhaler, powder spray device, vaporizer, patch, medicated stick, pipette, or jet of liquid. In some embodiments of the methods described herein, the nicotinic acetylcholine receptor agonist is administered into the nasal cavity by a syringe. In some embodiments of the methods described herein, the nicotinic acetylcholine receptor agonist is administered into the nasal cavity by a dropper. In some embodiments of the methods described herein, the nicotinic acetylcholine receptor agonist is administered into the nasal cavity by a bottle nebulizer. In some embodiments of the methods described herein, the nicotinic acetylcholine receptor agonist is administered into the nasal cavity by an atomization pump. In some embodiments of the methods described herein, the nicotinic acetylcholine receptor agonist is administered into the nasal cavity by an inhaler. In some embodiments of the methods described herein, the nicotinic acetylcholine receptor agonist is administered into the nasal cavity by a powder spray device. In some embodiments of the methods described herein, the nicotinic acetylcholine receptor agonist is administered into the nasal cavity by a vaporizer. In some embodiments of the methods described herein, the nicotinic acetylcholine receptor agonist is administered into the nasal cavity by a patch. In some embodiments of the methods described herein, the nicotinic acetylcholine receptor agonist is administered into the nasal cavity by a medicated stick. In some embodiments of the methods described herein, the nicotinic acetylcholine receptor agonist is administered into the nasal cavity by a pipette. In some embodiments of the methods described herein, the nicotinic acetylcholine receptor agonist is administered into the nasal cavity by a jet of liquid.

Pharmaceutical Formulations, Methods of Dosing, and Treatment Regimens

Also provided herein are pharmaceutical formulations of nicotinic acetylcholine receptor agonists for local administration into the nasal cavity of an individual. In some embodiments is a pharmaceutical formulation for local administration into the nasal cavity of an individual comprising a nicotinic acetylcholine receptor agonist formulated to prevent desensitization and in a dosage amount that is not systemically bioavailable. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising protein kinase C (PKC) or factors that upregulate or up-modulate PKC. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising cAMP-dependent protein kinase (PKA) or factors that upregulate or up-modulate PKA. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising a calcineurin inhibitor. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising a calcineurin inhibitor, wherein the calcineurin inhibitor is selected from cyclosporine, pimecrolimus, and tacrolimus. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising a calcineurin inhibitor, wherein the calcineurin inhibitor is cyclosporine. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising a calcineurin inhibitor, wherein the calcineurin inhibitor is pimecrolimus. In some embodiments is a pharmaceutical formulation for local administration into the nasal cavity of an individual comprising a nicotinic acetylcholine receptor agonist formulated to prevent desensitization and in a dosage amount that is not systemically bioavailable, further comprising a calcineurin inhibitor, wherein the calcineurin inhibitor is tacrolimus.

In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is nicotine. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is cytisine. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is epibatidine. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is varenicline. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is tebanicline. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is DBO-83. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is CC4. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is ABT-418. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is ABT-366833. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is ABT-202. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is ABT-894. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is SIB-1663. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is GTS-21. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is PHA-543613. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is PNU-282987. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is LY-2087101. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is A85380. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is 5-I-A85380.

In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is selected from a compound disclosed in WO 2008/057938, WO 2009/111550, WO 2010/028011, or WO 2010/028033.

In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist selectively binds to at least one of the peripheral nicotinic acetylcholine receptor subtypes selected from alpha3beta4, alpha4beta2, and alpha7. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist selectively binds to the peripheral nicotinic acetylcholine receptor subtype alpha3beta4. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist selectively binds to the peripheral nicotinic acetylcholine receptor subtype alpha4beta2. In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist selectively binds to the peripheral nicotinic acetylcholine receptor subtype alpha7.

In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist is a soft drug.

In some embodiments is a pharmaceutical formulation for local administration into the nasal cavity of an individual comprising a nicotinic acetylcholine receptor agonist formulated to prevent desensitization and in a dosage amount that is not systemically bioavailable, wherein the nicotinic acetylcholine receptor agonist has a structure selected from:

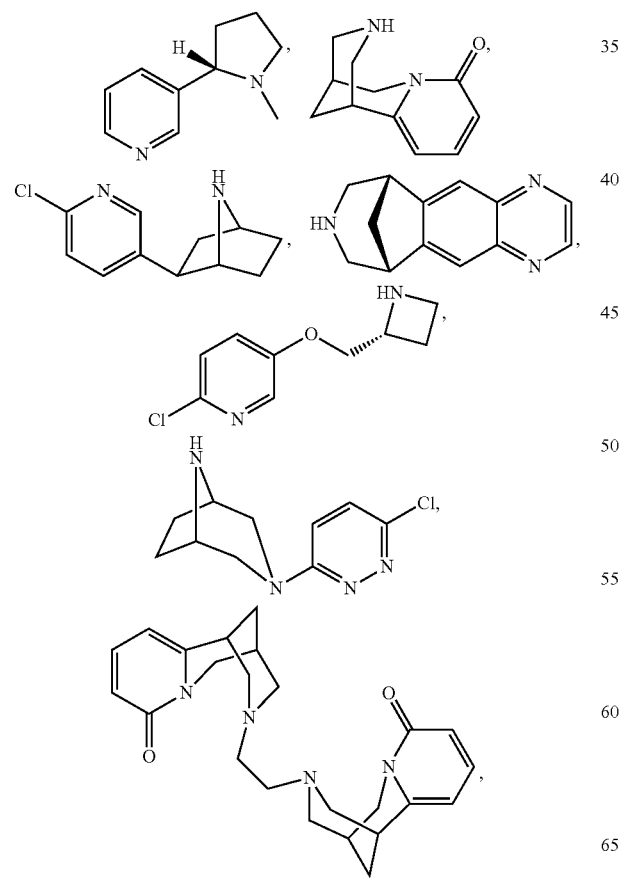

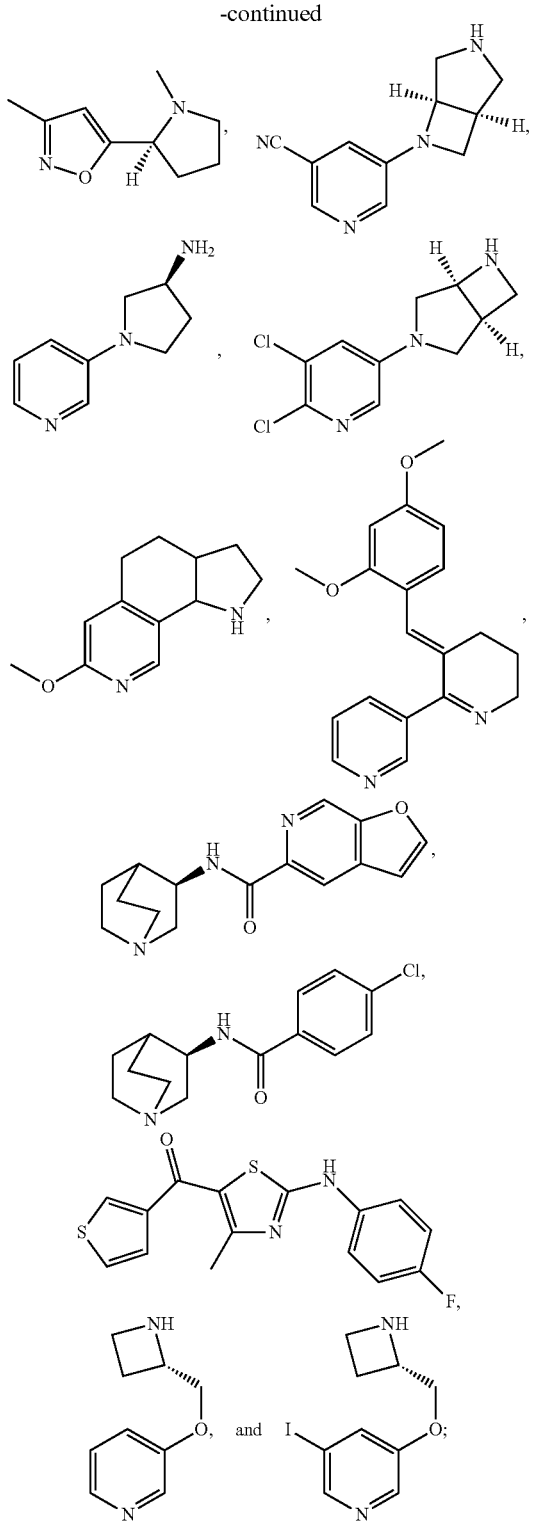

or a pharmaceutically acceptable salt thereof

Further described herein, in some embodiments, is a pharmaceutical formulation for local administration into the nasal cavity of an individual comprising a nicotinic acetylcholine receptor agonist formulated to prevent desensitization and in a dosage amount that does not result in undesired psychoactive side effects. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising protein kinase C (PKC) or factors that upregulate or up-modulate PKC. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising cAMP-dependent protein kinase (PKA) or factors that upregulate or up-modulate PKA. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising a calcineurin inhibitor. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising a calcineurin inhibitor, wherein the calcineurin inhibitor is selected from cyclosporine, pimecrolimus, and tacrolimus. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising a calcineurin inhibitor, wherein the calcineurin inhibitor is cyclosporine. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising a calcineurin inhibitor, wherein the calcineurin inhibitor is pimecrolimus. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, further comprising a calcineurin inhibitor, wherein the calcineurin inhibitor is tacrolimus.

In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is nicotine. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is cytisine. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is epibatidine. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is varenicline. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is tebanicline. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is DBO-83. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is CC4. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is ABT-418. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is ABT-366833. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is ABT-202. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is ABT-894. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is SIB-1663. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is GTS-21. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is PHA-543613. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is PNU-282987. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is LY-2087101. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is A85380. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is 5-I-A85380.

In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is selected from a compound disclosed in WO 2008/057938, WO 2009/111550, WO 2010/028011, or WO 2010/028033.

In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist is a soft drug.

In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist has a structure selected from:

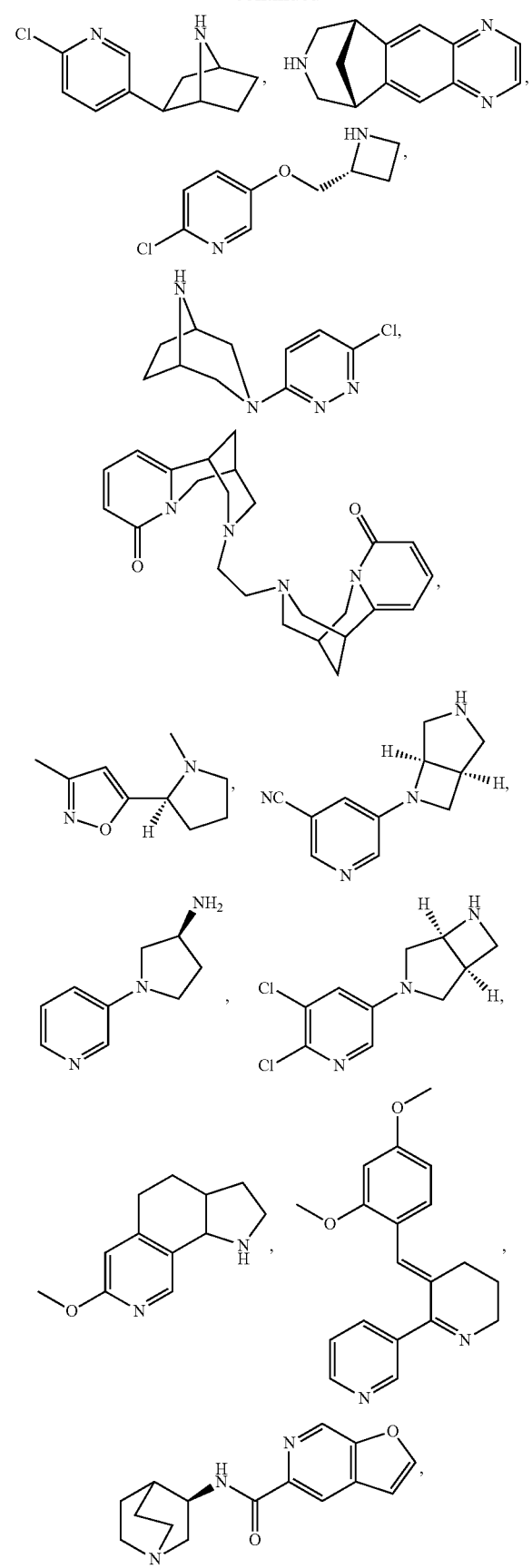

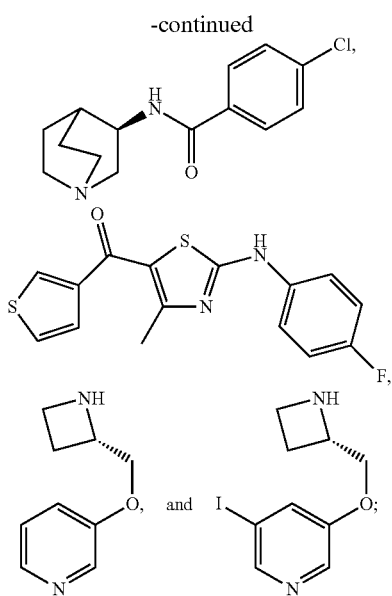

or a pharmaceutically acceptable salt thereof

In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist selectively binds to at least one of the peripheral nicotinic acetylcholine receptor subtypes selected from alpha3beta4, alpha4beta2, and alpha7. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist selectively binds to the peripheral nicotinic acetylcholine receptor subtype alpha3beta4. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist selectively binds to the peripheral nicotinic acetylcholine receptor subtype alpha4beta2. In some embodiments is a pharmaceutical formulation for local administration into the nasal cavity of an individual comprising a nicotinic acetylcholine receptor agonist formulated to prevent desensitization and in a dosage amount that does not result in undesired psychoactive side effects, wherein the nicotinic acetylcholine receptor agonist selectively binds to the peripheral nicotinic acetylcholine receptor subtype alpha7.

Further described herein, in some embodiments, is a pharmaceutical formulation for local administration into the nasal cavity of an individual comprising a nicotinic acetylcholine receptor agonist formulated to prevent desensitization and in a dosage amount that does not result in undesired systemic side effects. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising one or more substances selected from protein kinase C (PKC) or factors that upregulate or up-modulate PKC, cAMP-dependent protein kinase (PKA) or factors that upregulate or up-modulate PKA, and calcineurin inhibitors. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising protein kinase C (PKC) or factors that upregulate or up-modulate PKC. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising cAMP-dependent protein kinase (PKA) or factors that upregulate or up-modulate PKA. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising a calcineurin inhibitor. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising a calcineurin inhibitor, wherein the calcineurin inhibitor is selected from cyclosporine, pimecrolimus, and tacrolimus. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising a calcineurin inhibitor, wherein the calcineurin inhibitor is cyclosporine. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising a calcineurin inhibitor, wherein the calcineurin inhibitor is pimecrolimus. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, further comprising a calcineurin inhibitor, wherein the calcineurin inhibitor is tacrolimus.

In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is selected from nicotine, cytisine, epibatidine, varenicline, tebanicline, DBO-83, CC4, ABT-418, ABT-366833, ABT-202, ABT-894, SIB-1663, GTS-21, PHA-543613, PNU-282987, LY-2087101, A85380, and 5-I-A85380. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is nicotine. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is cytisine. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is epibatidine. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is varenicline. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is tebanicline. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is DBO-83. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is CC4. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is ABT-418. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is ABT-366833. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is ABT-202. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is ABT-894. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is SIB-1663. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is GTS-21. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is PHA-543613. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is PNU-282987. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is LY-2087101. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is A85380. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is 5-I-A85380.

In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is selected from a compound disclosed in WO 2008/057938, WO 2009/111550, WO 2010/028011, or WO 2010/028033.

In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist is a soft drug.

In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist has a structure selected from:

-continued

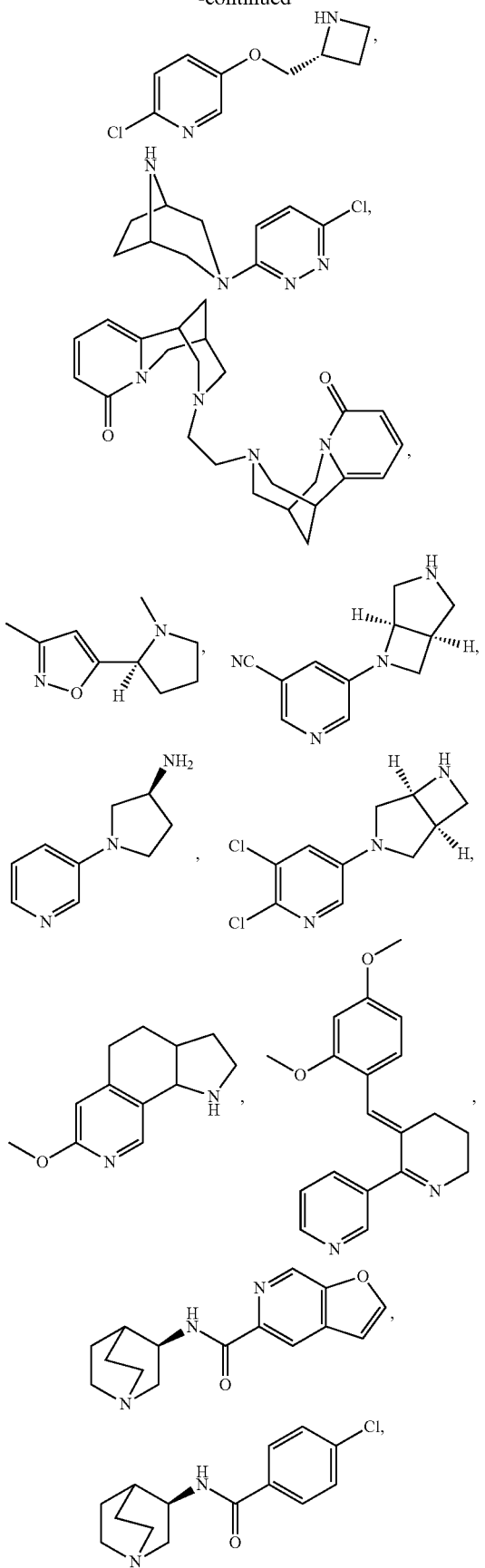

-continued

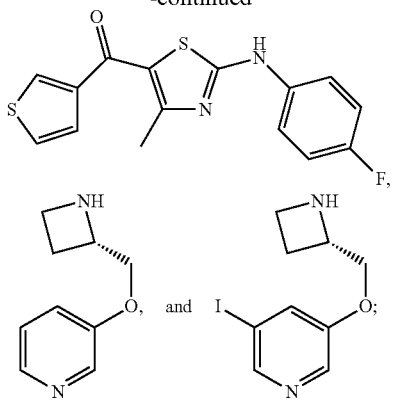

or a pharmaceutically acceptable salt thereof

In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist selectively binds to at least one of the peripheral nicotinic acetylcholine receptor subtypes selected from alpha3beta4, alpha4beta2, and alpha7. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist selectively binds to the peripheral nicotinic acetylcholine receptor subtype alpha3beta4. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist selectively binds to the peripheral nicotinic acetylcholine receptor subtype alpha4beta2. In some embodiments is a pharmaceutical formulation for local administration into the nasal cavity of an individual comprising a nicotinic acetylcholine receptor agonist formulated to prevent desensitization and in a dosage amount that does not result in undesired systemic side effects, wherein the nicotinic acetylcholine receptor agonist selectively binds to the peripheral nicotinic acetylcholine receptor subtype alpha7.

In another embodiment of any of the aforementioned pharmaceutical formulation embodiments, the pharmaceutical formulation comprises about 0.1 mg/mL of the nicotinic acetylcholine receptor agonist. In another embodiment of any of the aforementioned pharmaceutical formulation embodiments, the pharmaceutical formulation comprises about 0.2 mg/mL of the nicotinic acetylcholine receptor agonist. In another embodiment of any of the aforementioned pharmaceutical formulation embodiments, the pharmaceutical formulation comprises about 0.5 mg/mL of the nicotinic acetylcholine receptor agonist. In another embodiment of any of the aforementioned pharmaceutical formulation embodiments, the pharmaceutical formulation comprises about 1 mg/mL of the nicotinic acetylcholine receptor agonist. In another embodiment of any of the aforementioned pharmaceutical formulation embodiments, the pharmaceutical formulation comprises about 2 mg/mL of the nicotinic acetylcholine receptor agonist. In another embodiment of any of the aforementioned pharmaceutical formulation embodiments, the pharmaceutical formulation comprises about 3 mg/mL of the nicotinic acetylcholine receptor agonist. In another embodiment of any of the aforementioned pharmaceutical formulation embodiments, the pharmaceutical formulation comprises about 4 mg/mL of the nicotinic acetylcholine receptor agonist. In another embodiment of any of the aforementioned pharmaceutical formulation embodiments, the pharmaceutical formulation comprises about 5 mg/mL of the nicotinic acetylcholine receptor agonist. In another embodiment of any of the aforementioned pharmaceutical formulation embodiments, the pharmaceutical formulation comprises about 6 mg/mL of the nicotinic acetylcholine receptor agonist. In another embodiment of any of the aforementioned pharmaceutical formulation embodiments, the pharmaceutical formulation comprises about 7 mg/mL of the nicotinic acetylcholine receptor agonist. In another embodiment of any of the aforementioned pharmaceutical formulation embodiments, the pharmaceutical formulation comprises about 8 mg/mL of the nicotinic acetylcholine receptor agonist. In another embodiment of any of the aforementioned pharmaceutical formulation embodiments, the pharmaceutical formulation comprises about 9 mg/mL of the nicotinic acetylcholine receptor agonist. In another embodiment of any of the aforementioned pharmaceutical formulation embodiments, the pharmaceutical formulation comprises about 10 mg/mL of the nicotinic acetylcholine receptor agonist. In another embodiment of any of the aforementioned pharmaceutical formulation embodiments, the pharmaceutical formulation comprises about 12 mg/mL of the nicotinic acetylcholine receptor agonist. In another embodiment of any of the aforementioned pharmaceutical formulation embodiments, the pharmaceutical formulation comprises about 15 mg/mL of the nicotinic acetylcholine receptor agonist. In another embodiment of any of the aforementioned pharmaceutical formulation embodiments, the pharmaceutical formulation comprises about 20 mg/mL of the nicotinic acetylcholine receptor agonist.

In another embodiment of any of the aforementioned pharmaceutical formulation embodiments, the pharmaceutical formulation comprises at least 1 microgram of the nicotinic acetylcholine receptor agonist per dose. In another embodiment of any of the aforementioned pharmaceutical formulation embodiments, the pharmaceutical formulation comprises at least 5 micrograms of the nicotinic acetylcholine receptor agonist per dose. In another embodiment of any of the aforementioned pharmaceutical formulation embodiments, the pharmaceutical formulation comprises at least 10 micrograms of the nicotinic acetylcholine receptor agonist per dose. In another embodiment of any of the aforementioned pharmaceutical formulation embodiments, the pharmaceutical formulation comprises at least 25 micrograms of the nicotinic acetylcholine receptor agonist per dose. In another embodiment of any of the aforementioned pharmaceutical formulation embodiments, the pharmaceutical formulation comprises at least 50 micrograms of the nicotinic acetylcholine receptor agonist per dose. In another embodiment of any of the aforementioned pharmaceutical formulation embodiments, the pharmaceutical formulation comprises at least 100 micrograms of the nicotinic acetylcholine receptor agonist per dose. In another embodiment of any of the aforementioned pharmaceutical formulation embodiments, the pharmaceutical formulation comprises at least 250 micrograms of the nicotinic acetylcholine receptor agonist per dose. In another embodiment of any of the aforementioned pharmaceutical formulation embodiments, the pharmaceutical formulation comprises at least 500 micrograms of the nicotinic acetylcholine receptor agonist per dose. In another embodiment of any of the aforementioned pharmaceutical formulation embodiments, the pharmaceutical formulation comprises at least 750 micrograms of the nicotinic acetylcholine receptor agonist per dose. In another embodiment of any of the aforementioned pharmaceutical formulation embodiments, the pharmaceutical formulation comprises at least 1000 micrograms of the nicotinic acetylcholine receptor agonist per dose. In another embodiment of any of the aforementioned pharmaceutical formulation embodiments, the pharmaceutical formulation comprises between 1 microgram and 1000 micrograms of the nicotinic acetylcholine receptor agonist per dose. In another embodiment of any of the aforementioned pharmaceutical formulation embodiments, the pharmaceutical formulation comprises between 5 micrograms and 1000 micrograms of the nicotinic acetylcholine receptor agonist per dose. In another embodiment of any of the aforementioned pharmaceutical formulation embodiments, the pharmaceutical formulation comprises between 5 micrograms and 100 micrograms of the nicotinic acetylcholine receptor agonist per dose. In another embodiment of any of the aforementioned pharmaceutical formulation embodiments, the pharmaceutical formulation comprises between 5 micrograms and 50 micrograms of the nicotinic acetylcholine receptor agonist per dose. In another embodiment of any of the aforementioned pharmaceutical formulation embodiments, the pharmaceutical formulation comprises between 10 micrograms and 50 micrograms of the nicotinic acetylcholine receptor agonist per dose. In another embodiment of any of the aforementioned pharmaceutical formulation embodiments, the pharmaceutical formulation comprises between 25 micrograms and 1000 micrograms of the nicotinic acetylcholine receptor agonist per dose. In another embodiment of any of the aforementioned pharmaceutical formulation embodiments, the pharmaceutical formulation comprises between 50 micrograms and 1000 micrograms of the nicotinic acetylcholine receptor agonist per dose. In another embodiment of any of the aforementioned pharmaceutical formulation embodiments, the pharmaceutical formulation comprises between 100 micrograms and 1000 micrograms of the nicotinic acetylcholine receptor agonist is per dose. In another embodiment of any of the aforementioned pharmaceutical formulation embodiments, the pharmaceutical formulation comprises between 100 micrograms and 750 micrograms of the nicotinic acetylcholine receptor agonist per dose. In another embodiment of any of the aforementioned pharmaceutical formulation embodiments, the pharmaceutical formulation comprises between 150 micrograms and 750 micrograms of the nicotinic acetylcholine receptor agonist per dose. In another embodiment of any of the aforementioned pharmaceutical formulation embodiments, the pharmaceutical formulation comprises between 150 micrograms and 600 micrograms of the nicotinic acetylcholine receptor agonist per dose.

In another embodiment of any of the aforementioned pharmaceutical formulation embodiments, the pharmaceutical formulation is administered once daily. In another embodiment of any of the aforementioned pharmaceutical formulation embodiments, the pharmaceutical formulation is administered at least once daily. In another embodiment of any of the aforementioned pharmaceutical formulation embodiments, the pharmaceutical formulation is administered twice daily. In another embodiment of any of the aforementioned pharmaceutical formulation embodiments, the pharmaceutical formulation is administered at least twice daily. In another embodiment of any of the aforementioned pharmaceutical formulation embodiments, the pharmaceutical formulation is administered three times daily. In another embodiment of any of the aforementioned pharmaceutical formulation embodiments, the pharmaceutical formulation is administered at least three times daily. In another embodiment of any of the aforementioned pharmaceutical formulation embodiments, the pharmaceutical formulation is administered for one day. In another embodiment of any of the aforementioned pharmaceutical formulation embodiments, the pharmaceutical formulation is administered for at least two days. In another embodiment of any of the aforementioned pharmaceutical formulation embodiments, the pharmaceutical formulation is administered for at least three days. In another embodiment of any of the aforementioned pharmaceutical formulation embodiments, the pharmaceutical formulation is administered for at least four days. In another embodiment of any of the aforementioned pharmaceutical formulation embodiments, the pharmaceutical formulation is administered for at least five days. In another embodiment of any of the aforementioned pharmaceutical formulation embodiments, the pharmaceutical formulation is administered for at least seven days. In another embodiment of any of the aforementioned pharmaceutical formulation embodiments, the pharmaceutical formulation is administered for at least ten days. In another embodiment of any of the aforementioned pharmaceutical formulation embodiments, the pharmaceutical formulation is administered for at least fourteen days. In another embodiment of any of the aforementioned pharmaceutical formulation embodiments, the pharmaceutical formulation is administered for at least twenty one days. In another embodiment of any of the aforementioned pharmaceutical formulation embodiments, the pharmaceutical formulation is administered for at least thirty days.

In another embodiment of any of the aforementioned pharmaceutical formulation embodiments, the pharmaceutical formulation is administered in alternating nostrils.

In certain embodiments, the pharmaceutical formulations described herein are administered for prophylactic and/or therapeutic treatments. In certain therapeutic applications, the pharmaceutical formulations are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, the pharmaceutical formulations described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments wherein the patient's condition does not improve, upon the doctor's discretion the administration of the pharmaceutical formulations are administered chronically, that is, for an extended period of time, including throughout the duration of the patient's life in order to ameliorate or otherwise control or limit the symptoms of the patient's disease or condition.

In certain embodiments wherein a patient's status does improve, the dose of the pharmaceutical formulation being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In certain embodiments the dose of the pharmaceutical formulation being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular pharmaceutical formulation, disease condition and its severity, the identity (e.g., weight, sex) of the subject or host in need of treatment, but can nevertheless be determined according to the particular circumstances surrounding the case, including, e.g., the specific nicotinic acetylcholine receptor agonist being administered, the condition being treated, and the subject being treated.

A pharmaceutical formulation, as used herein, refers to a mixture of a nicotinic acetylcholine receptor agonist as described herein with other chemical components (i.e. pharmaceutically acceptable inactive ingredients), such as carriers, excipients, binders, filling agents, suspending agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. In some embodiments, the pharmaceutical formulations described herein are mixed with other active ingredients, as in combination therapy. In some embodiments, the pharmaceutical formulations include other therapeutically valuable substances. In other embodiments, the pharmaceutical formulations include other medicinal or pharmaceutical agents, carriers, adjuvants, preserving, stabilizing, wetting or emulsifying agents, solution promoters, salts for regulating the osmotic pressure, and/or buffers.

In some embodiments, the pharmaceutical formulations described herein refer to a mixture of a nicotinic acetylcholine receptor agonist and a buffer. In some embodiments, the pharmaceutical formulations described herein refer to a mixture of a nicotinic acetylcholine receptor agonist and a phosphate buffer. In some embodiments, the pharmaceutical formulations described herein refer to a mixture of a nicotinic acetylcholine receptor agonist and a phosphate buffer, wherein the pH of the phosphate buffer is around 7.0. In some embodiments, the pharmaceutical formulations described herein refer to a mixture of a nicotinic acetylcholine receptor agonist and a phosphate-citrate buffer. In some embodiments, the pharmaceutical formulations described herein refer to a mixture of a nicotinic acetylcholine receptor agonist and a phosphate-citrate buffer, wherein the pH of the phosphate-citrate buffer is around 6.0. In some embodiments, the pharmaceutical formulations described herein refer to a mixture of a nicotinic acetylcholine receptor agonist and a phosphate-citrate buffer. In some embodiments, the pharmaceutical formulations described herein refer to a mixture of a nicotinic acetylcholine receptor agonist and a phosphate-citrate buffer, wherein the pH of the phosphate-citrate buffer is around 5.0.

The pharmaceutical formulation facilitates administration of the compound to an organism. In practicing the methods provided herein, therapeutically effective amounts of nicotinic acetylcholine receptor agonist described herein are administered in a pharmaceutical formulation to a mammal having a disease, disorder, or condition to be treated. In some embodiments, the mammal is a human. A therapeutically effective amount can vary widely depending on the severity of the disease, the age and relative health of the subject, the potency of the compound used and other factors. The nicotinic acetylcholine receptor agonist can be used singly or in combination with one or more therapeutic agents as components of mixtures.

The pharmaceutical formulations described herein are administered to the nasal cavity of a subject. The pharmaceutical formulations described herein include, but are not limited to, liquids, suspensions, aerosols, gels, ointments, dry powders, creams, pastes, lotions, or balms.

Pharmaceutical formulations including a nicotinic acetylcholine receptor agonist as described herein are manufactured in a conventional manner.

The pharmaceutical compositions will include a nicotinic acetylcholine receptor agonist as described herein as an active ingredient in free-acid or free-base form, or in a pharmaceutically acceptable salt form. In addition, the methods and pharmaceutical formulations described herein include the use of N-oxides (if appropriate), crystalline forms, amorphous phases, as well as active metabolites of these nicotinic acetylcholine receptor agonists having the same type of activity. In some embodiments, the nicotinic acetylcholine receptor agonists described herein may exist in unsolvated form or in solvated forms with pharmaceutically acceptable solvents such as water, ethanol, and the like. The solvated forms of the nicotinic acetylcholine receptor agonists presented herein are also considered to be disclosed herein. In some embodiments, the compounds may exist as tautomers. All tautomers are included within the scope of the nicotinic acetylcholine receptor agonists presented herein.

In some embodiments, the nicotinic acetylcholine receptor agonists exist as enantiomers, diastereomers, or other stereoisomeric forms. The nicotinic acetylcholine receptor agonists disclosed herein include all enantiomeric, diastereomeric, and epimeric forms as well as mixtures thereof.

In certain embodiments, the pharmaceutical formulations provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, the pharmaceutical formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical formulations described herein, which include a nicotinic acetylcholine receptor agonist, are formulated into any suitable dosage form, including but not limited to, liquids, suspensions, aerosols, gels, ointments, dry powders, creams, pastes, lotions, or balms. The pharmaceutical formulations described herein, which include a nicotinic acetylcholine receptor agonist are formulated into any suitable dosage form, are administered into the nasal cavity by a syringe, dropper, bottle nebulizer, atomization pump, inhaler, powder spray device, vaporizer, patch, medicated stick, pipette, or jet of liquid.

Combination Therapy

In certain instances, it is appropriate to administer a nicotinic acetylcholine receptor agonist in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical formulation or composition, and are, because of different physical and chemical characteristics, administered by different routes. In one embodiment, the initial administration is made according to established protocols, and then, based upon the observed effects, the dosage, modes of administration and times of administration, further modified.

In various embodiments, a nicotinic acetylcholine receptor agonist, is administered concurrently (e.g., simultaneously, essentially simultaneously or within the same treatment protocol) or sequentially, with other therapeutic reagents that are selected for their particular usefulness against the condition that is being treated. In certain embodiments, the determination of the order of administration, and the number of repetitions of administration of each therapeutic agent during a treatment protocol, is based upon evaluation of the disease being treated and the condition of the patient.

In some embodiments, a nicotinic acetylcholine receptor agonist, is administered concurrently (e.g., simultaneously, essentially simultaneously or within the same treatment protocol) or sequentially, with another therapeutic reagent for treating dry disease. In some embodiments, a nicotinic acetylcholine receptor agonist, is administered concurrently (e.g., simultaneously, essentially simultaneously or within the same treatment protocol) or sequentially, with Restasis® eye drops. In some embodiments, a nicotinic acetylcholine receptor agonist, is administered concurrently (e.g., simultaneously, essentially simultaneously or within the same treatment protocol) or sequentially, with artificial tears. In some embodiments, a nicotinic acetylcholine receptor agonist, is administered concurrently (e.g., simultaneously, essentially simultaneously or within the same treatment protocol) or sequentially, with ocular steroids.

For combination therapies described herein, dosages of the co-administered compounds vary depending on the type of co-drug employed, on the specific drug employed, on the disease or condition being treated and so forth.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Administration of a combination of agents, as used herein, includes administration of the agents described in a single composition or in a combination therapy wherein one or more agent is administered separately from at least one other agent.

In some embodiments, a nicotinic acetylcholine receptor agonist is administered in combination with the use of a medical device. In some embodiments, a nicotinic acetylcholine receptor agonist is administered in combination with the use of punctal plugs.

EXAMPLES

The following specific examples are to be construed as merely illustrative, and not limitative of the remainder of the disclosure in any way whatsoever.

Example 1a

Clinical Trial to Evaluate Safety and Efficacy of Nasal Administration of Nicotinic Acetylcholine Receptor Agonist Varenicline for Treatment of Dry Eye Disease (DED)

Purpose:
This study evaluated the use of varenicline 0.1% nasal spray (OC-01) for the treatment of moderate to severe DED in adult patients. This study investigated the safety and efficacy of using OC-01 to induce aqueous tear production and reduce the symptoms of DED.
Patients:
A total of 30 participants with moderate to severe dry eye, meeting the following inclusion and exclusion criteria were enrolled.
Criteria:
Inclusion:
Males and females ≥18 years of age
Willing to sign the informed consent and deemed capable of complying with the requirements of the study protocol
At screening visit 1, Schirmer tear test (with topical anesthesia) of ≤10 mm/5 minutes in at least one eye;
At screening visit 1, Schirmer test (with topical anesthesia and nasal stimulation with cotton swab) of at least 7 mm higher than the unstimulated value in at least one eye;
Baseline Ocular Surface Disease Index score of at least 23 with no more than 3 responses of "not applicable" at the first screening visit
Normal lid/lash anatomy, blinking function and closure
Exclusion:
Chronic or recurrent epistaxis
Use of tobacco or nicotine products (cigarettes, cigars, electronic cigarettes) within the past 1 year
Coagulation disorders that may lead to increased bleeding such as hemophilia and thrombocytopenia
Lacrimal gland, nasal or sinus neoplasia or significant trauma; prior lacrimal gland, nasal or sinus surgery or ablation leading to denervation of the gland or nasal passages as evidenced by a lack of response with the cotton swab nasal stimulation.
Severe nasal airway obstruction (e.g. severe septal deviation or inferior turbinate hypertrophy)
Ocular surgery (such as refractive or cataract surgery) in either eye within 3 months of the first screening visit;
A systemic condition or disease not stabilized or judged by the investigator to be incompatible with participation in the study (e.g. current systemic infection, uncontrolled autoimmune disease, uncontrolled immunodeficiency disease, history of myocardial infarction, uncontrolled hypertension, etc.) or with the frequent assessments required by the study
The history or presence of any ocular disorder or condition in either eye that would likely interfere with the interpretation of the study results or patient safety such as a significant corneal or conjunctival scarring, pterygium or nodular pinguecula; current ocular infection or inflammation not associated with dry eye; clinically significant anterior (epithelial) basement membrane corneal dystrophy or other clinically significant corneal dystrophy or degeneration; clinically significant blepharitis; ocular herpetic infection, etc.
Known hypersensitivity to any of the procedural agents or materials in the study drug that contact the nasal mucosa.
Active or uncontrolled severe systemic allergy, chronic seasonal allergies, rhinitis or sinusitis requiring treatment (i.e. antihistamines, decongestants, oral or aerosol steroids) at the time of initial screening
Be currently taking any medication known to cause ocular drying (e.g., cyclosporine, antihistamines, tricyclic antidepressants, anxiolytics, antimuscarinics, beta-blocking agents, diuretics, phenothiazines, steroids, etc.) that has not been used on a stable dosing regimen for 30 days prior to the first screening visit
Dissolvable punctal plugs (participants with silicone plugs or permanent occlusion of punctal ducts are eligible)
Active contact lens use unless discontinued at least 7 days prior to the first screening visit and for the duration of the study
Participation in any clinical trial with a new active substance or a new device during the past 3 months
Women who are pregnant, planning a pregnancy or nursing at study entry. A urine pregnancy test will be administered to women of childbearing age.
Known allergies or adverse reactions to varenicline
Any unstable or uncontrolled cardiac, pulmonary, renal, oncology, neurology, metabolic or other systemic condition that, in the opinion of the investigator, would like require the patient to seek emergent medical treatment during the course of this study. This includes but is not limited to cardiac arrhythmias, hypertension, coagulopathies, renal failure and diabetes mellitus.

Inclusion/Exclusion Exceptions:

The investigator has the right to exclude any patient's participation in the study if he/she deems it in the best interest of the patient.

Minor exceptions to the inclusion/exclusion criteria should be submitted to the sponsor and prospectively approved with the advice of the medical monitor when required.

Major exceptions affecting patient safety/rights or data validity should be reported promptly to the IRB/EC by the investigator.

Primary Outcome:

The design of this study will enable the following measurements with respect to OC-01 and tear production:

Change in tear production associated with a single dose of OC-01

Secondary Outcome:

The design of this study will enable the following measurements with respect to OC-01 and tear production:

Change in tear production associated with a single dose of vehicle

Change in symptoms associated with a single dose of OC-01

Duration of symptomatic relief associated with a single dose of OC-01

Change in symptoms associated with a single dose of vehicle

Duration of symptomatic relief associated with a single dose of vehicle

Together these comparisons will provide valuable information about the safety and efficacy of OC-01 for increasing tear production in patients with dry eye disease.

The primary safety endpoint of this study is incidence and relatedness of adverse events (AE). Descriptive statistics of adverse events will be provided as will narratives of any serious, unexpected or drug-related AEs. During the study, integrity of the nasal passages will be monitored by a suitably qualified practitioner for patient safety.

Study Design:

This study is a prospective, single-arm crossover study to evaluate the safety and efficacy of OC-01 varenicline 0.1% nasal spray in participants with moderate to severe dry eye. Up to 30 participants will be enrolled and followed for a duration of seven days.

At the first screening visit, all eligible participants will cease taking their current artificial tears or lubricant drops for the duration of the study and will be provided unit dose unpreserved artificial tears to be taken if their dry eye symptoms become intolerable. Empty unit dose vials will be collected at each study visit and counted. Patients will be instructed not to use artificial tears within 30 minutes of nasal drug administration or within 2 hours of a study visit.

At the second screening visit/Study Day 0, all eligible participants will be tested for their response two nasal formulations: OC-01 and a vehicle control. Tear production will be assessed immediately prior and after delivery of each intranasal dose using the Jones Schirmer Test in both eyes. The order that each patient receives the OC-01 and vehicle formulation will be randomly assigned, and both the patient and examiner will be masked to the identity of the nasal formulation. At least 90 minutes following the tear production assessment, change in symptoms in response to delivery of each of the two nasal formulations will be assessed. The symptom assessment will be performed using a well-established environmental challenge model, the ClimaTears Goggle System manufactured by Biocentric Developments, LLC.

After testing on Day 0, all patients will receive a bottle of OC-01 to take home and self-administer once daily from Day 1 and Day 6. On Day 7, patients will return to the clinic where they will again be assessed for tear production and symptoms with administration of each nasal formulation.

Tear Assessments

The following ocular surface and tear film assessments will be performed in the order shown:

Ocular Surface Staining—Corneal Staining Using Fluorescein

Ocular surface staining using fluorescein and lissamine green will be assessed and recorded in the schematic representation of 5 corneal and 6 conjunctival regions per eye on the case report form using the National Eye Institute grading system. A pictorial and descriptive grading scale (grades 0 to 3) are included on the case report form (CRF).

1. Corneal staining should be assessed using 1.0 mg sodium fluorescein strips.
2. After wetting the end of the strip with a single drop of buffered saline, the excess is shaken into a waste bin with a sharp flick.
3. The lower lid is then pulled down and the flat end of the tip should be gently applied to the inferior tarsal conjunctiva with the intent of instilling a very small volume of dye and not inducing reflex tearing.
4. The patient will be instructed to blink naturally several times without forced closure of the eyelid to distribute the fluorescein.
5. After allowing fluorescein to remain on the eye for at least one minute, the 5 corneal regions will be graded using a yellow (Wratten #12) barrier filter in conjunction with the cobalt (blue) filter to maximize the view of the fluorescence. The upper eyelid is lifted slightly to grade the entire corneal surface. To enhance the contrast, position the yellow barrier filter in the path of the returning light (not in the path of the incident light).

Tear Film Breakup Time (TFBUT)

TFBUT will be assessed using slit lamp biomicroscopy according to the following steps:

1. The slit-lamp will be set to a magnification of approximately 10×.
2. With adequate fluorescein in place (preferably using DET strips), the subject will be asked to stare straight ahead without blinking until told otherwise. The test should be performed in a room with no direct air on the patient's face.
3. A stopwatch will be used to record the time between the last complete blink and the first appearance of a growing micelle indicating tear-film breakup.
   Note: If the patient blinks prematurely prior to the development of the breakup of the mires, the examiner should continue to try to obtain a reading.
4. Once TFBUT is observed, instruct patient to blink freely. This test should then be repeated a second time on the same eye.
5. If the difference between the first and second readings differs by more than two seconds, a third measurement should be performed and recorded.
6. This procedure will then be performed in the other eye.
7. It is recommended that TFBUT be performed in a room with a temperature of approximately 18 C with a humidity of approximately 50%.

Ocular Surface Staining—Conjunctival Staining Using Lissamine Green

Ocular surface staining assessment will be completed with lissamine green conjunctival staining.
1. The lissamine green ophthalmic strip should be wetted with buffered saline and applied to the inferior tarsal conjunctiva. Care should be taken to instill adequate dye.
2. After allowing lissamine green to remain on the eye for one minute, the six nasal and temporal conjunctival regions will be graded.
3. To grade the temporal zone, the subject should be instructed to look nasally; to grade the nasal zone, the subject should be instructed to look temporally.
4. This procedure should then be completed in the other eye.

Schirmer Test

At screening visit #1, one basal Jones Schirmer test will be performed followed by a Schirmer test with cotton swab nasal stimulation. The Jones Schirmer test with topical anesthetic will be used to assess tear production using the following steps:
1. Topical anesthetic drops such as 0.5% proparacaine hydrochloride or equivalent should be instilled in both eyes of the patient.
2. The patient will be instructed to keep the eyes gently closed for one minute.
3. After opening the eyes and allowing the eyes to recover for approximately one additional minute, excess moisture in the inferior fornix is gently removed with a cotton-tipped applicator.
4. Schirmer strips (35 mm×5 mm size filter paper strip) will be placed in each eye at the junction of the middle and lateral thirds of the lower eye lid.
5. Under ambient light, the patient will be instructed to look forward and to blink normally during the course of the test. The test should be performed in a room with no direct air on the patient's face.
6. After five minutes, strips will be removed from both eyes and the amount of wetting will be recorded. The strips should be taped to the CRF. Note: Should the Schirmer score reach maximum prior to the 5 minute endpoint, the strip can be removed and the time it took to reach maximum recorded. However, the strip from the contralateral eye should not be removed until it too has reached maximum score prior to the 5 minute endpoint.
7. As multiple Schirmer tests are performed, new anesthetic drops should be added as necessary.

Schirmer Test Using Cotton Swab Nasal Stimulation
1. At screening visit #1, the Schirmer test should be performed using cotton swab nasal stimulation. With new strips in place, the examiner should insert cotton swabs in both participant's nostrils simultaneously and gently probe both nasal middle turbinates for approximately 30 seconds. After this, the examiner can simply hold the swabs in place, applying gentle pressure, and repeat probing intermittently as necessary.
2. Alternatively, the participant can be instructed to hold the cotton swabs and gently probe both nasal turbinates simultaneously, resting intermittently before probing again. The examiner should continuously coach the participant on how to perform this test properly.
3. The Schirmer strips should remain in place until five minutes have elapsed or they have reached maximum score.

Both Schirmer scores will be recorded and verified that they meet the inclusion criteria. As two Schirmer tests are performed, new anesthetic drops should be instilled as necessary.

Schirmer Test with Each of Two Nasal Spray Applications

With each of the two nasal applications, the Jones Schirmer test with topical anesthetic will be used to assess tear production using the following steps:
1. Topical anesthetic drops such as 0.5% proparacaine hydrochloride or equivalent should be instilled in both eyes of the participant for each application.
2. The participant will be instructed to keep the eyes gently closed for one minute.
3. After opening the eyes and allowing the eyes to recover for approximately one additional minute, excess moisture in the inferior fornix is gently removed with a spear.
4. Schirmer strips (35 mm×5 mm size filter paper strip) will be placed in each eye at the junction of the middle and lateral thirds of the lower eye lid.
5. Under ambient light, the participant will be instructed to look forward and to blink normally during the course of the test. The test should be performed in a room with no direct air on the participant's face.
6. After five minutes, strips will be removed from both eyes and the amount of wetting will be recorded. The strips should be taped to the CRF.

Dry Eye Provocation and Symptom Assessment

The ClimaTears Goggle System (Biocentric Developments, LLC) will be used to reduce periocular humidity and induce symptoms of dry eye in patients. This system was designed for the purpose of standardizing testing conditions for clinical studies of dry eye patients.

Patients will wear the ClimaTears Goggles continuously for up to 90 min, with their symptoms recorded via the visual analog scale (VAS) every 5 minutes during the testing period. The subject will be asked to rate their dryness symptoms (both eyes simultaneously) by placing a vertical mark on the horizontal line to indicate the level of discomfort. 0 corresponds to "no dryness" and 5 corresponds to "maximal dryness." The assessment line length of the scale will be 100 mm. There are many symptoms of dry eye, including dryness, sticky feeling, burning, foreign body sensation, itching, blurred vision, sensitivity to light, and pain. Please rate the severity of your current "dryness" symptoms (and no others) by drawing a vertical line on the line below:

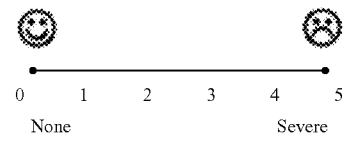

At Day 0, patients will begin wearing the goggles and be monitored until they reach a symptom score of 45 mm or more for two consecutive measurements, at which time they will randomly receive a dose of either OC-01 nasal spray or the control nasal spray, administered 2.5 minutes after the two consecutive 45 mm measurements. Symptoms will be continued to be monitored until the patient again reaches a score of 45 mm or higher for two consecutive measurements, at which time the patient will receive a second nasal dose of which ever test article they did not receive the first time. After the second nasal dose, symptoms will be monitored again until the patient reaches a score of a score of 45 mm or higher for two consecutive measurements. At that time, the goggles will be removed and the test will end. If still ongoing, the test will be terminated after 90 minutes of exposure to the goggles environment. At the end of this period, each patient will be asked to decide which of the nasal sprays made provided more relief of their dry eye symptoms.

At Day 7, patients will begin wearing the goggles and be monitored until they reach a symptom score of 45 mm or more for two consecutive measurements, at which time they will receive a dose of the OC-01 nasal spray. Symptoms will continued to be monitored until the patient again reaches a score of 45 mm or higher for two consecutive measurements, at which time the goggles will be removed and the test will end. If still ongoing, the test will be terminated after 90 minutes of exposure to the goggles environment.

Patients entering with a baseline symptoms score of more than 45 mm will have a treatment threshold equal to this baseline score, and will thus receive treatment after two consecutive symptoms measurements of greater than or equal to this value.

The instructions (in bold above) will be read to the patient before the test begins, and before recording symptoms values immediately following the administration of either nasal spray.

Figure 2:
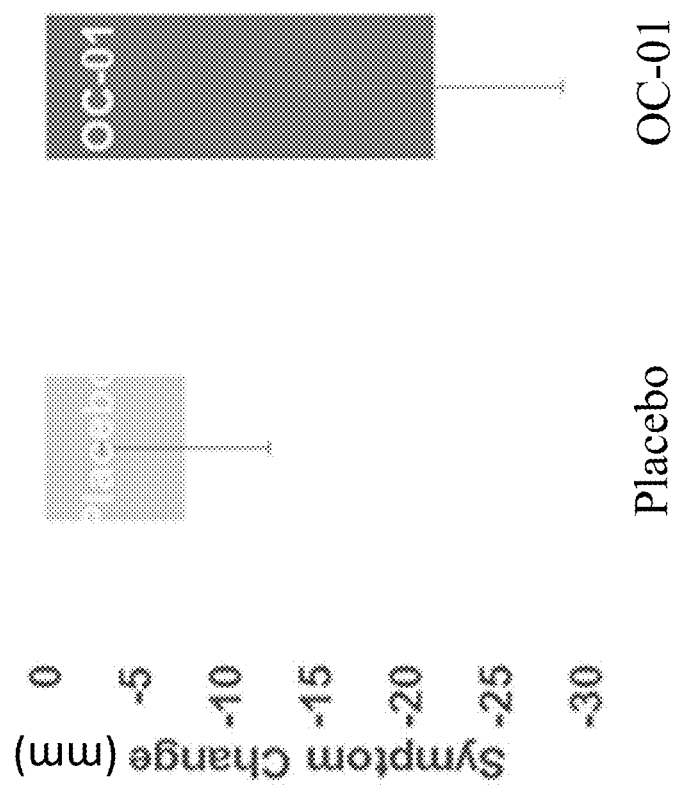
FIG. 2 depicts patient reported symptoms of dry eye in patients receiving OC-01 versus placebo.

Results of tear film assessments and dry eye symptoms:

Tear production in patients receiving OC-01 increased in a statitistically significant amount compared to both baseline and placebo (FIG. 1). In addition, patient reported symptoms of dry eye also improved in patients receiving OC-01 versus placebo (FIG. 2).

Example 1b

Clinical Trial to Evaluate Safety and Efficacy of Nasal Administration of Nicotinic Acetylcholine Receptor Agonist Cytisine for Treatment of Dry Eye Disease (DED)

Purpose:

This study evaluates the use of cytisine 0.1% nasal spray (OC-02) for the treatment of moderate to severe DED in adult patients. This study will investigate the safety and efficacy of using OC-02 to induce aqueous tear production and reduce the symptoms of DED.

Patients:

A total of 30 participants with moderate to severe dry eye, meeting the following inclusion and exclusion criteria will be enrolled.

Criteria:
Inclusion:
Males and females ≥18 years of age
Willing to sign the informed consent and deemed capable of complying with the requirements of the study protocol
At screening visit 1, Schirmer tear test (with topical anesthesia) of ≤10 mm/5 minutes in at least one eye;
At screening visit 1, Schirmer test (with topical anesthesia and nasal stimulation with cotton swab) of at least 7 mm higher than the unstimulated value in at least one eye;
Baseline Ocular Surface Disease Index score of at least 23 with no more than 3 responses of "not applicable" at the first screening visit
Normal lid/lash anatomy, blinking function and closure
Exclusion:
Chronic or recurrent epistaxis
Use of tobacco or nicotine products (cigarettes, cigars, electronic cigarettes) within the past 1 year
Coagulation disorders that may lead to increased bleeding such as hemophilia and thrombocytopenia
Lacrimal gland, nasal or sinus neoplasia or significant trauma; prior lacrimal gland, nasal or sinus surgery or ablation leading to denervation of the gland or nasal passages as evidenced by a lack of response with the cotton swab nasal stimulation.
Severe nasal airway obstruction (e.g. severe septal deviation or inferior turbinate hypertrophy)
Ocular surgery (such as refractive or cataract surgery) in either eye within 3 months of the first screening visit;
A systemic condition or disease not stabilized or judged by the investigator to be incompatible with participation in the study (e.g. current systemic infection, uncontrolled autoimmune disease, uncontrolled immunodeficiency disease, history of myocardial infarction, uncontrolled hypertension, etc.) or with the frequent assessments required by the study
The history or presence of any ocular disorder or condition in either eye that would likely interfere with the interpretation of the study results or patient safety such as a significant corneal or conjunctival scarring, pterygium or nodular pinguecula; current ocular infection or inflammation not associated with dry eye; clinically significant anterior (epithelial) basement membrane corneal dystrophy or other clinically significant corneal dystrophy or degeneration; clinically significant blepharitis; ocular herpetic infection, etc.
Known hypersensitivity to any of the procedural agents or materials in the study drug that contact the nasal mucosa.
Active or uncontrolled severe systemic allergy, chronic seasonal allergies, rhinitis or sinusitis requiring treatment (i.e. antihistamines, decongestants, oral or aerosol steroids) at the time of initial screening
Be currently taking any medication known to cause ocular drying (e.g., cyclosporine, antihistamines, tricyclic antidepressants, anxiolytics, antimuscarinics, beta-blocking agents, diuretics, phenothiazines, steroids, etc.) that has not been used on a stable dosing regimen for 30 days prior to the first screening visit
Dissolvable punctal plugs (participants with silicone plugs or permanent occlusion of punctal ducts are eligible)
Active contact lens use unless discontinued at least 7 days prior to the first screening visit and for the duration of the study
Participation in any clinical trial with a new active substance or a new device during the past 3 months
Women who are pregnant, planning a pregnancy or nursing at study entry. A urine pregnancy test will be administered to women of childbearing age.
Known allergies or adverse reactions to cytisine
Any unstable or uncontrolled cardiac, pulmonary, renal, oncology, neurology, metabolic or other systemic condition that, in the opinion of the investigator, would like require the patient to seek emergent medical treatment during the course of this study. This includes but is not limited to cardiac arrhythmias, hypertension, coagulopathies, renal failure and diabetes mellitus.
Inclusion/Exclusion Exceptions:
The investigator has the right to exclude any patient's participation in the study if he/she deems it in the best interest of the patient.
Minor exceptions to the inclusion/exclusion criteria should be submitted to the sponsor and prospectively approved with the advice of the medical monitor when required.

Major exceptions affecting patient safety/rights or data validity should be reported promptly to the IRB/EC by the investigator.

Primary Outcome:

The design of this study will enable the following measurements with respect to OC-02 and tear production:
Change in tear production associated with a single dose of OC-02

Secondary Outcome:

The design of this study will enable the following measurements with respect to OC-02 and tear production:
Change in tear production associated with a single dose of vehicle
Change in symptoms associated with a single dose of OC-02
Duration of symptomatic relief associated with a single dose of OC-02
Change in symptoms associated with a single dose of vehicle
Duration of symptomatic relief associated with a single dose of vehicle Together these comparisons will provide valuable information about the safety and efficacy of OC-02 for increasing tear production in patients with dry eye disease.

The primary safety endpoint of this study is incidence and relatedness of adverse events (AE). Descriptive statistics of adverse events will be provided as will narratives of any serious, unexpected or drug-related AEs. During the study, integrity of the nasal passages will be monitored by a suitably qualified practitioner for patient safety.

Study Design:

This study is a prospective, single-arm crossover study to evaluate the safety and efficacy of OC-02 cytisine 0.1% nasal spray in participants with moderate to severe dry eye. Up to 30 participants will be enrolled and followed for a duration of seven days.

At the first screening visit, all eligible participants will cease taking their current artificial tears or lubricant drops for the duration of the study and will be provided unit dose unpreserved artificial tears to be taken if their dry eye symptoms become intolerable. Empty unit dose vials will be collected at each study visit and counted. Patients will be instructed not to use artificial tears within 30 minutes of nasal drug administration or within 2 hours of a study visit.

At the second screening visit/Study Day 0, all eligible participants will be tested for their response two nasal formulations: OC-02 and a vehicle control. Tear production will be assessed immediately prior and after delivery of each intranasal dose using the Jones Schirmer Test in both eyes. The order that each patient receives the OC-02 and vehicle formulation will be randomly assigned, and both the patient and examiner will be masked to the identity of the nasal formulation. At least 90 minutes following the tear production assessment, change in symptoms in response to delivery of each of the two nasal formulations will be assessed. The symptom assessment will be performed using a well-established environmental challenge model, the ClimaTears Goggle System manufactured by Biocentric Developments, LLC.

After testing on Day 0, all patients will receive a bottle of OC-02 to take home and self-administer once daily from Day 1 and Day 6. On Day 7, patients will return to the clinic where they will again be assessed for tear production and symptoms with administration of each nasal formulation.

Tear Assessments

The following ocular surface and tear film assessments will be performed in the order shown:

Ocular Surface Staining—Corneal Staining Using Fluorescein

Ocular surface staining using fluorescein and lissamine green will be assessed and recorded in the schematic representation of 5 corneal and 6 conjunctival regions per eye on the case report form using the National Eye Institute grading system. A pictorial and descriptive grading scale (grades 0 to 3) are included on the case report form (CRF).
1. Corneal staining should be assessed using 1.0 mg sodium fluorescein strips.
2. After wetting the end of the strip with a single drop of buffered saline, the excess is shaken into a waste bin with a sharp flick.
3. The lower lid is then pulled down and the flat end of the tip should be gently applied to the inferior tarsal conjunctiva with the intent of instilling a very small volume of dye and not inducing reflex tearing.
4. The patient will be instructed to blink naturally several times without forced closure of the eyelid to distribute the fluorescein.
5. After allowing fluorescein to remain on the eye for at least one minute, the 5 corneal regions will be graded using a yellow (Wratten #12) barrier filter in conjunction with the cobalt (blue) filter to maximize the view of the fluorescence. The upper eyelid is lifted slightly to grade the entire corneal surface. To enhance the contrast, position the yellow barrier filter in the path of the returning light (not in the path of the incident light).

Tear Film Breakup Time (TFBUT)

TFBUT will be assessed using slit lamp biomicroscopy according to the following steps:
1. The slit-lamp will be set to a magnification of approximately 10×. 2. With adequate fluorescein in place (preferably using DET strips), the subject will be asked to stare straight ahead without blinking until told otherwise. The test should be performed in a room with no direct air on the patient's face.
3. A stopwatch will be used to record the time between the last complete blink and the first appearance of a growing micelle indicating tear-film breakup.
   Note: If the patient blinks prematurely prior to the development of the breakup of the mires, the examiner should continue to try to obtain a reading.
4. Once TFBUT is observed, instruct patient to blink freely. This test should then be repeated a second time on the same eye.
5. If the difference between the first and second readings differs by more than two seconds, a third measurement should be performed and recorded.
6. This procedure will then be performed in the other eye.
7. It is recommended that TFBUT be performed in a room with a temperature of approximately 18 C with a humidity of approximately 50%.

Ocular Surface Staining—Conjunctival Staining Using Lissamine Green

Ocular surface staining assessment will be completed with lissamine green conjunctival staining.
1. The lissamine green ophthalmic strip should be wetted with buffered saline and applied to the inferior tarsal conjunctiva. Care should be taken to instill adequate dye.
2. After allowing lissamine green to remain on the eye for one minute, the six nasal and temporal conjunctival regions will be graded.
3. To grade the temporal zone, the subject should be instructed to look nasally; to grade the nasal zone, the subject should be instructed to look temporally.
4. This procedure should then be completed in the other eye.

Schirmer Test

At screening visit #1, one basal Jones Schirmer test will be performed followed by a Schirmer test with cotton swab nasal stimulation. The Jones Schirmer test with topical anesthetic will be used to assess tear production using the following steps:
1. Topical anesthetic drops such as 0.5% proparacaine hydrochloride or equivalent should be instilled in both eyes of the patient.
2. The patient will be instructed to keep the eyes gently closed for one minute.
3. After opening the eyes and allowing the eyes to recover for approximately one additional minute, excess moisture in the inferior fornix is gently removed with a cotton-tipped applicator.
4. Schirmer strips (35 mm×5 mm size filter paper strip) will be placed in each eye at the junction of the middle and lateral thirds of the lower eye lid.
5. Under ambient light, the patient will be instructed to look forward and to blink normally during the course of the test. The test should be performed in a room with no direct air on the patient's face.
6. After five minutes, strips will be removed from both eyes and the amount of wetting will be recorded. The strips should be taped to the CRF. Note: Should the Schirmer score reach maximum prior to the 5 minute endpoint, the strip can be removed and the time it took to reach maximum recorded. However, the strip from the contralateral eye should not be removed until it too has reached maximum score prior to the 5 minute endpoint.
7. As multiple Schirmer tests are performed, new anesthetic drops should be added as necessary.

Schirmer Test Using Cotton Swab Nasal Stimulation
1. At screening visit #1, the Schirmer test should be performed using cotton swab nasal stimulation. With new strips in place, the examiner should insert cotton swabs in both participant's nostrils simultaneously and gently probe both nasal middle turbinates for approximately 30 seconds. After this, the examiner can simply hold the swabs in place, applying gentle pressure, and repeat probing intermittently as necessary.
2. Alternatively, the participant can be instructed to hold the cotton swabs and gently probe both nasal turbinates simultaneously, resting intermittently before probing again. The examiner should continuously coach the participant on how to perform this test properly.
3. The Schirmer strips should remain in place until five minutes have elapsed or they have reached maximum score.

Both Schirmer scores will be recorded and verified that they meet the inclusion criteria. As two Schirmer tests are performed, new anesthetic drops should be instilled as necessary.

Schirmer Test with Each of Two Nasal Spray Applications

With each of the two nasal applications, the Jones Schirmer test with topical anesthetic will be used to assess tear production using the following steps:
1. Topical anesthetic drops such as 0.5% proparacaine hydrochloride or equivalent should be instilled in both eyes of the participant for each application.
2. The participant will be instructed to keep the eyes gently closed for one minute.
3. After opening the eyes and allowing the eyes to recover for approximately one additional minute, excess moisture in the inferior fornix is gently removed with a spear.
4. Schirmer strips (35 mm×5 mm size filter paper strip) will be placed in each eye at the junction of the middle and lateral thirds of the lower eye lid.
5. Under ambient light, the participant will be instructed to look forward and to blink normally during the course of the test. The test should be performed in a room with no direct air on the participant's face.
6. After five minutes, strips will be removed from both eyes and the amount of wetting will be recorded. The strips should be taped to the CRF.

Dry Eye Provocation and Symptom Assessment

The ClimaTears Goggle System (Biocentric Developments, LLC) will be used to reduce periocular humidity and induce symptoms of dry eye in patients. This system was designed for the purpose of standardizing testing conditions for clinical studies of dry eye patients.

Patients will wear the ClimaTears Goggles continuously for up to 90 min, with their symptoms recorded via the visual analog scale (VAS) every 5 minutes during the testing period. The subject will be asked to rate their dryness symptoms (both eyes simultaneously) by placing a vertical mark on the horizontal line to indicate the level of discomfort. 0 corresponds to "no dryness" and 5 corresponds to "maximal dryness." The assessment line length of the scale will be 100 mm. There are many symptoms of dry eye, including dryness, sticky feeling, burning, foreign body sensation, itching, blurred vision, sensitivity to light, and pain. Please rate the severity of your current "dryness" symptoms (and no others) by drawing a vertical line on the line below:

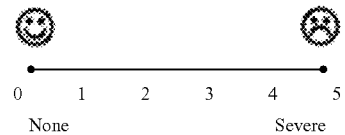

At Day 0, patients will begin wearing the goggles and be monitored until they reach a symptom score of 45 mm or more for two consecutive measurements, at which time they will randomly receive a dose of either OC-02 nasal spray or the control nasal spray, administered 2.5 minutes after the two consecutive 45 mm measurements. Symptoms will be continued to be monitored until the patient again reaches a score of 45 mm or higher for two consecutive measurements, at which time the patient will receive a second nasal dose of which ever test article they did not receive the first time. After the second nasal dose, symptoms will be monitored again until the patient reaches a score of a score of 45 mm or higher for two consecutive measurements. At that time, the goggles will be removed and the test will end. If still ongoing, the test will be terminated after 90 minutes of exposure to the goggles environment. At the end of this period, each patient will be asked to decide which of the nasal sprays made provided more relief of their dry eye symptoms.

At Day 7, patients will begin wearing the goggles and be monitored until they reach a symptom score of 45 mm or more for two consecutive measurements, at which time they will receive a dose of the OC-02 nasal spray. Symptoms will continued to be monitored until the patient again reaches a score of 45 mm or higher for two consecutive measurements, at which time the goggles will be removed and the test will end. If still ongoing, the test will be terminated after 90 minutes of exposure to the goggles environment.

Patients entering with a baseline symptoms score of more than 45 mm will have a treatment threshold equal to this baseline score, and will thus receive treatment after two consecutive symptoms measurements of greater than or equal to this value.

The instructions (in bold above) will be read to the patient before the test begins, and before recording symptoms values immediately following the administration of either nasal spray.

Example 1c

Clinical Trial to Evaluate Safety and Efficacy of Nasal Administration of Nicotinic Acetylcholine Receptor Agonist Epibatidine for Treatment of Dry Eye Disease (DED)

Purpose:
This study evaluates the use of epibatidine 0.1% nasal spray (OC-03) for the treatment of moderate to severe DED in adult patients. This study will investigate the safety and efficacy of using OC-03 to induce aqueous tear production and reduce the symptoms of DED.

Patients:
A total of 30 participants with moderate to severe dry eye, meeting the following inclusion and exclusion criteria will be enrolled.

Criteria:
Inclusion:
Males and females ≥18 years of age
Willing to sign the informed consent and deemed capable of complying with the requirements of the study protocol
At screening visit 1, Schirmer tear test (with topical anesthesia) of ≤10 mm/5 minutes in at least one eye;
At screening visit 1, Schirmer test (with topical anesthesia and nasal stimulation with cotton swab) of at least 7 mm higher than the unstimulated value in at least one eye;
Baseline Ocular Surface Disease Index score of at least 23 with no more than 3 responses of "not applicable" at the first screening visit
Normal lid/lash anatomy, blinking function and closure Exclusion:
Chronic or recurrent epistaxis
Use of tobacco or nicotine products (cigarettes, cigars, electronic cigarettes) within the past 1 year
Coagulation disorders that may lead to increased bleeding such as hemophilia and thrombocytopenia
Lacrimal gland, nasal or sinus neoplasia or significant trauma; prior lacrimal gland, nasal or sinus surgery or ablation leading to denervation of the gland or nasal passages as evidenced by a lack of response with the cotton swab nasal stimulation.
Severe nasal airway obstruction (e.g. severe septal deviation or inferior turbinate hypertrophy)
Ocular surgery (such as refractive or cataract surgery) in either eye within 3 months of the first screening visit;
A systemic condition or disease not stabilized or judged by the investigator to be incompatible with participation in the study (e.g. current systemic infection, uncontrolled autoimmune disease, uncontrolled immunodeficiency disease, history of myocardial infarction, uncontrolled hypertension, etc.) or with the frequent assessments required by the study
The history or presence of any ocular disorder or condition in either eye that would likely interfere with the interpretation of the study results or patient safety such as a significant corneal or conjunctival scarring, pterygium or nodular pinguecula; current ocular infection or inflammation not associated with dry eye; clinically significant anterior (epithelial) basement membrane corneal dystrophy or other clinically significant corneal dystrophy or degeneration; clinically significant blepharitis; ocular herpetic infection, etc.
Known hypersensitivity to any of the procedural agents or materials in the study drug that contact the nasal mucosa.
Active or uncontrolled severe systemic allergy, chronic seasonal allergies, rhinitis or sinusitis requiring treatment (i.e. antihistamines, decongestants, oral or aerosol steroids) at the time of initial screening
Be currently taking any medication known to cause ocular drying (e.g., cyclosporine, antihistamines, tricyclic antidepressants, anxiolytics, antimuscarinics, beta-blocking agents, diuretics, phenothiazines, steroids, etc.) that has not been used on a stable dosing regimen for 30 days prior to the first screening visit
Dissolvable punctal plugs (participants with silicone plugs or permanent occlusion of punctal ducts are eligible)
Active contact lens use unless discontinued at least 7 days prior to the first screening visit and for the duration of the study
Participation in any clinical trial with a new active substance or a new device during the past 3 months
Women who are pregnant, planning a pregnancy or nursing at study entry. A urine pregnancy test will be administered to women of childbearing age.
Known allergies or adverse reactions to epibatidine
Any unstable or uncontrolled cardiac, pulmonary, renal, oncology, neurology, metabolic or other systemic condition that, in the opinion of the investigator, would like require the patient to seek emergent medical treatment during the course of this study. This includes but is not limited to cardiac arrhythmias, hypertension, coagulopathies, renal failure and diabetes mellitus.

Inclusion/Exclusion Exceptions:
The investigator has the right to exclude any patient's participation in the study if he/she deems it in the best interest of the patient.
Minor exceptions to the inclusion/exclusion criteria should be submitted to the sponsor and prospectively approved with the advice of the medical monitor when required.
Major exceptions affecting patient safety/rights or data validity should be reported promptly to the IRB/EC by the investigator.

Primary Outcome:
The design of this study will enable the following measurements with respect to OC-03 and tear production:
Change in tear production associated with a single dose of OC-03

Secondary Outcome:
The design of this study will enable the following measurements with respect to OC-03 and tear production:
Change in tear production associated with a single dose of vehicle
Change in symptoms associated with a single dose of OC-03
Duration of symptomatic relief associated with a single dose of OC-03
Change in symptoms associated with a single dose of vehicle Duration of symptomatic relief associated with a single dose of vehicle Together these comparisons will provide valuable information about the safety and efficacy of OC-03 for increasing tear production in patients with dry eye disease.

The primary safety endpoint of this study is incidence and relatedness of adverse events (AE). Descriptive statistics of adverse events will be provided as will narratives of any serious, unexpected or drug-related AEs. During the study, integrity of the nasal passages will be monitored by a suitably qualified practitioner for patient safety.

Study Design:

This study is a prospective, single-arm crossover study to evaluate the safety and efficacy of OC-03 epibatidine 0.1% nasal spray in participants with moderate to severe dry eye. Up to 30 participants will be enrolled and followed for a duration of seven days.

At the first screening visit, all eligible participants will cease taking their current artificial tears or lubricant drops for the duration of the study and will be provided unit dose unpreserved artificial tears to be taken if their dry eye symptoms become intolerable. Empty unit dose vials will be collected at each study visit and counted. Patients will be instructed not to use artificial tears within 30 minutes of nasal drug administration or within 2 hours of a study visit.

At the second screening visit/Study Day 0, all eligible participants will be tested for their response two nasal formulations: OC-03 and a vehicle control. Tear production will be assessed immediately prior and after delivery of each intranasal dose using the Jones Schirmer Test in both eyes. The order that each patient receives the OC-03 and vehicle formulation will be randomly assigned, and both the patient and examiner will be masked to the identity of the nasal formulation. At least 90 minutes following the tear production assessment, change in symptoms in response to delivery of each of the two nasal formulations will be assessed. The symptom assessment will be performed using a well-established environmental challenge model, the ClimaTears Goggle System manufactured by Biocentric Developments, LLC.

After testing on Day 0, all patients will receive a bottle of OC-03 to take home and self-administer once daily from Day 1 and Day 6. On Day 7, patients will return to the clinic where they will again be assessed for tear production and symptoms with administration of each nasal formulation.

Tear Assessments

The following ocular surface and tear film assessments will be performed in the order shown:

Ocular Surface Staining—Corneal Staining Using Fluorescein

Ocular surface staining using fluorescein and lissamine green will be assessed and recorded in the schematic representation of 5 corneal and 6 conjunctival regions per eye on the case report form using the National Eye Institute grading system. A pictorial and descriptive grading scale (grades 0 to 3) are included on the case report form (CRF).

1. Corneal staining should be assessed using 1.0 mg sodium fluorescein strips.
2. After wetting the end of the strip with a single drop of buffered saline, the excess is shaken into a waste bin with a sharp flick.
3. The lower lid is then pulled down and the flat end of the tip should be gently applied to the inferior tarsal conjunctiva with the intent of instilling a very small volume of dye and not inducing reflex tearing.
4. The patient will be instructed to blink naturally several times without forced closure of the eyelid to distribute the fluorescein.
5. After allowing fluorescein to remain on the eye for at least one minute, the 5 corneal regions will be graded using a yellow (Wratten #12) barrier filter in conjunction with the cobalt (blue) filter to maximize the view of the fluorescence. The upper eyelid is lifted slightly to grade the entire corneal surface. To enhance the contrast, position the yellow barrier filter in the path of the returning light (not in the path of the incident light).

Tear Film Breakup Time (TFBUT)

TFBUT will be assessed using slit lamp biomicroscopy according to the following steps:

1. The slit-lamp will be set to a magnification of approximately 10×.
2. With adequate fluorescein in place (preferably using DET strips), the subject will be asked to stare straight ahead without blinking until told otherwise. The test should be performed in a room with no direct air on the patient's face.
3. A stopwatch will be used to record the time between the last complete blink and the first appearance of a growing micelle indicating tear-film breakup.
   Note: If the patient blinks prematurely prior to the development of the breakup of the mires, the examiner should continue to try to obtain a reading.
4. Once TFBUT is observed, instruct patient to blink freely. This test should then be repeated a second time on the same eye.
5. If the difference between the first and second readings differs by more than two seconds, a third measurement should be performed and recorded.
6. This procedure will then be performed in the other eye.
7. It is recommended that TFBUT be performed in a room with a temperature of approximately 18 C with a humidity of approximately 50%.

Ocular Surface Staining—Conjunctival Staining Using Lissamine Green

Ocular surface staining assessment will be completed with lissamine green conjunctival staining.

1. The lissamine green ophthalmic strip should be wetted with buffered saline and applied to the inferior tarsal conjunctiva. Care should be taken to instill adequate dye.
2. After allowing lissamine green to remain on the eye for one minute, the six nasal and temporal conjunctival regions will be graded.
3. To grade the temporal zone, the subject should be instructed to look nasally; to grade the nasal zone, the subject should be instructed to look temporally.
4. This procedure should then be completed in the other eye.

Schirmer Test

At screening visit #1, one basal Jones Schirmer test will be performed followed by a Schirmer test with cotton swab nasal stimulation. The Jones Schirmer test with topical anesthetic will be used to assess tear production using the following steps:

1. Topical anesthetic drops such as 0.5% proparacaine hydrochloride or equivalent should be instilled in both eyes of the patient.
2. The patient will be instructed to keep the eyes gently closed for one minute.
3. After opening the eyes and allowing the eyes to recover for approximately one additional minute, excess moisture in the inferior fornix is gently removed with a cotton-tipped applicator.

4. Schirmer strips (35 mm×5 mm size filter paper strip) will be placed in each eye at the junction of the middle and lateral thirds of the lower eye lid.

5. Under ambient light, the patient will be instructed to look forward and to blink normally during the course of the test. The test should be performed in a room with no direct air on the patient's face.

6. After five minutes, strips will be removed from both eyes and the amount of wetting will be recorded. The strips should be taped to the CRF. Note: Should the Schirmer score reach maximum prior to the 5 minute endpoint, the strip can be removed and the time it took to reach maximum recorded. However, the strip from the contralateral eye should not be removed until it too has reached maximum score prior to the 5 minute endpoint.

7. As multiple Schirmer tests are performed, new anesthetic drops should be added as necessary.

Schirmer Test Using Cotton Swab Nasal Stimulation

1. At screening visit #1, the Schirmer test should be performed using cotton swab nasal stimulation. With new strips in place, the examiner should insert cotton swabs in both participant's nostrils simultaneously and gently probe both nasal middle turbinates for approximately 30 seconds. After this, the examiner can simply hold the swabs in place, applying gentle pressure, and repeat probing intermittently as necessary.

2. Alternatively, the participant can be instructed to hold the cotton swabs and gently probe both nasal turbinates simultaneously, resting intermittently before probing again. The examiner should continuously coach the participant on how to perform this test properly.

3. The Schirmer strips should remain in place until five minutes have elapsed or they have reached maximum score.

Both Schirmer scores will be recorded and verified that they meet the inclusion criteria. As two Schirmer tests are performed, new anesthetic drops should be instilled as necessary.

Schirmer Test with Each of Two Nasal Spray Applications

With each of the two nasal applications, the Jones Schirmer test with topical anesthetic will be used to assess tear production using the following steps:

1. Topical anesthetic drops such as 0.5% proparacaine hydrochloride or equivalent should be instilled in both eyes of the participant for each application.

2. The participant will be instructed to keep the eyes gently closed for one minute.

3. After opening the eyes and allowing the eyes to recover for approximately one additional minute, excess moisture in the inferior fornix is gently removed with a spear.

4. Schirmer strips (35 mm×5 mm size filter paper strip) will be placed in each eye at the junction of the middle and lateral thirds of the lower eye lid.

5. Under ambient light, the participant will be instructed to look forward and to blink normally during the course of the test. The test should be performed in a room with no direct air on the participant's face.

6. After five minutes, strips will be removed from both eyes and the amount of wetting will be recorded. The strips should be taped to the CRF.

Dry Eye Provocation and Symptom Assessment

The ClimaTears Goggle System (Biocentric Developments, LLC) will be used to reduce periocular humidity and induce symptoms of dry eye in patients. This system was designed for the purpose of standardizing testing conditions for clinical studies of dry eye patients.

Patients will wear the ClimaTears Goggles continuously for up to 90 min, with their symptoms recorded via the visual analog scale (VAS) every 5 minutes during the testing period. The subject will be asked to rate their dryness symptoms (both eyes simultaneously) by placing a vertical mark on the horizontal line to indicate the level of discomfort. 0 corresponds to "no dryness" and 5 corresponds to "maximal dryness." The assessment line length of the scale will be 100 mm. There are many symptoms of dry eye, including dryness, sticky feeling, burning, foreign body sensation, itching, blurred vision, sensitivity to light, and pain. Please rate the severity of your current "dryness" symptoms (and no others) by drawing a vertical line on the line below:

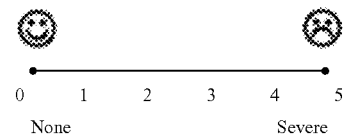

At Day 0, patients will begin wearing the goggles and be monitored until they reach a symptom score of 45 mm or more for two consecutive measurements, at which time they will randomly receive a dose of either OC-03 nasal spray or the control nasal spray, administered 2.5 minutes after the two consecutive 45 mm measurements. Symptoms will be continued to be monitored until the patient again reaches a score of 45 mm or higher for two consecutive measurements, at which time the patient will receive a second nasal dose of which ever test article they did not receive the first time. After the second nasal dose, symptoms will be monitored again until the patient reaches a score of a score of 45 mm or higher for two consecutive measurements. At that time, the goggles will be removed and the test will end. If still ongoing, the test will be terminated after 90 minutes of exposure to the goggles environment. At the end of this period, each patient will be asked to decide which of the nasal sprays made provided more relief of their dry eye symptoms.

At Day 7, patients will begin wearing the goggles and be monitored until they reach a symptom score of 45 mm or more for two consecutive measurements, at which time they will receive a dose of the OC-03 nasal spray. Symptoms will continued to be monitored until the patient again reaches a score of 45 mm or higher for two consecutive measurements, at which time the goggles will be removed and the test will end. If still ongoing, the test will be terminated after 90 minutes of exposure to the goggles environment.

Patients entering with a baseline symptoms score of more than 45 mm will have a treatment threshold equal to this baseline score, and will thus receive treatment after two consecutive symptoms measurements of greater than or equal to this value.

The instructions (in bold above) will be read to the patient before the test begins, and before recording symptoms values immediately following the administration of either nasal spray.

Example 1d

Clinical Trial to Evaluate Safety and Efficacy of Nasal Administration of Nicotinic Acetylcholine Receptor Agonist Tebanicline for Treatment of Dry Eye Disease (DED)

Purpose:

This study evaluates the use of tebanicline 0.1% nasal spray (OC-04) for the treatment of moderate to severe DED in adult patients. This study will investigate the safety and efficacy of using OC-04 to induce aqueous tear production and reduce the symptoms of DED.

Patients:

A total of 30 participants with moderate to severe dry eye, meeting the following inclusion and exclusion criteria will be enrolled.

Criteria:

Inclusion:
- Males and females ≥18 years of age
- Willing to sign the informed consent and deemed capable of complying with the requirements of the study protocol
- At screening visit 1, Schirmer tear test (with topical anesthesia) of ≤10 mm/5 minutes in at least one eye;
- At screening visit 1, Schirmer test (with topical anesthesia and nasal stimulation with cotton swab) of at least 7 mm higher than the unstimulated value in at least one eye;
- Baseline Ocular Surface Disease Index score of at least 23 with no more than 3 responses of "not applicable" at the first screening visit
- Normal lid/lash anatomy, blinking function and closure Exclusion:
- Chronic or recurrent epistaxis
- Use of tobacco or nicotine products (cigarettes, cigars, electronic cigarettes) within the past 1 year
- Coagulation disorders that may lead to increased bleeding such as hemophilia and thrombocytopenia
- Lacrimal gland, nasal or sinus neoplasia or significant trauma; prior lacrimal gland, nasal or sinus surgery or ablation leading to denervation of the gland or nasal passages as evidenced by a lack of response with the cotton swab nasal stimulation.
- Severe nasal airway obstruction (e.g. severe septal deviation or inferior turbinate hypertrophy)
- Ocular surgery (such as refractive or cataract surgery) in either eye within 3 months of the first screening visit;
- A systemic condition or disease not stabilized or judged by the investigator to be incompatible with participation in the study (e.g. current systemic infection, uncontrolled autoimmune disease, uncontrolled immunodeficiency disease, history of myocardial infarction, uncontrolled hypertension, etc.) or with the frequent assessments required by the study
- The history or presence of any ocular disorder or condition in either eye that would likely interfere with the interpretation of the study results or patient safety such as a significant corneal or conjunctival scarring, pterygium or nodular pinguecula; current ocular infection or inflammation not associated with dry eye; clinically significant anterior (epithelial) basement membrane corneal dystrophy or other clinically significant corneal dystrophy or degeneration; clinically significant blepharitis; ocular herpetic infection, etc.
- Known hypersensitivity to any of the procedural agents or materials in the study drug that contact the nasal mucosa.
- Active or uncontrolled severe systemic allergy, chronic seasonal allergies, rhinitis or sinusitis requiring treatment (i.e. antihistamines, decongestants, oral or aerosol steroids) at the time of initial screening
- Be currently taking any medication known to cause ocular drying (e.g., cyclosporine, antihistamines, tricyclic antidepressants, anxiolytics, antimuscarinics, beta-blocking agents, diuretics, phenothiazines, steroids, etc.) that has not been used on a stable dosing regimen for 30 days prior to the first screening visit
- Dissolvable punctal plugs (participants with silicone plugs or permanent occlusion of punctal ducts are eligible)
- Active contact lens use unless discontinued at least 7 days prior to the first screening visit and for the duration of the study
- Participation in any clinical trial with a new active substance or a new device during the past 3 months
- Women who are pregnant, planning a pregnancy or nursing at study entry. A urine pregnancy test will be administered to women of childbearing age.
- Known allergies or adverse reactions to tebanicline
- Any unstable or uncontrolled cardiac, pulmonary, renal, oncology, neurology, metabolic or other systemic condition that, in the opinion of the investigator, would like require the patient to seek emergent medical treatment during the course of this study. This includes but is not limited to cardiac arrhythmias, hypertension, coagulopathies, renal failure and diabetes mellitus.

Inclusion/Exclusion Exceptions:
- The investigator has the right to exclude any patient's participation in the study if he/she deems it in the best interest of the patient.
- Minor exceptions to the inclusion/exclusion criteria should be submitted to the sponsor and prospectively approved with the advice of the medical monitor when required.
- Major exceptions affecting patient safety/rights or data validity should be reported promptly to the IRB/EC by the investigator.

Primary Outcome:

The design of this study will enable the following measurements with respect to OC-04 and tear production:
- Change in tear production associated with a single dose of OC-04

Secondary Outcome:

The design of this study will enable the following measurements with respect to OC-04 and tear production:
- Change in tear production associated with a single dose of vehicle
- Change in symptoms associated with a single dose of OC-04
- Duration of symptomatic relief associated with a single dose of OC-04
- Change in symptoms associated with a single dose of vehicle
- Duration of symptomatic relief associated with a single dose of vehicle Together these comparisons will provide valuable information about the safety and efficacy of OC-04 for increasing tear production in patients with dry eye disease.

The primary safety endpoint of this study is incidence and relatedness of adverse events (AE). Descriptive statistics of adverse events will be provided as will narratives of any serious, unexpected or drug-related AEs. During the study, integrity of the nasal passages will be monitored by a suitably qualified practitioner for patient safety.

Study Design:

This study is a prospective, single-arm crossover study to evaluate the safety and efficacy of OC-04 tebanicline 0.1% nasal spray in participants with moderate to severe dry eye. Up to 30 participants will be enrolled and followed for a duration of seven days.

At the first screening visit, all eligible participants will cease taking their current artificial tears or lubricant drops for the duration of the study and will be provided unit dose unpreserved artificial tears to be taken if their dry eye symptoms become intolerable. Empty unit dose vials will be collected at each study visit and counted. Patients will be instructed not to use artificial tears within 30 minutes of nasal drug administration or within 2 hours of a study visit.

At the second screening visit/Study Day 0, all eligible participants will be tested for their response two nasal formulations: OC-04 and a vehicle control. Tear production will be assessed immediately prior and after delivery of each intranasal dose using the Jones Schirmer Test in both eyes. The order that each patient receives the OC-04 and vehicle formulation will be randomly assigned, and both the patient and examiner will be masked to the identity of the nasal formulation. At least 90 minutes following the tear production assessment, change in symptoms in response to delivery of each of the two nasal formulations will be assessed. The symptom assessment will be performed using a well-established environmental challenge model, the ClimaTears Goggle System manufactured by Biocentric Developments, LLC.

After testing on Day 0, all patients will receive a bottle of OC-04 to take home and self-administer once daily from Day 1 and Day 6. On Day 7, patients will return to the clinic where they will again be assessed for tear production and symptoms with administration of each nasal formulation.

Tear Assessments

The following ocular surface and tear film assessments will be performed in the order shown:

Ocular Surface Staining—Corneal Staining Using Fluorescein

Ocular surface staining using fluorescein and lissamine green will be assessed and recorded in the schematic representation of 5 corneal and 6 conjunctival regions per eye on the case report form using the National Eye Institute grading system. A pictorial and descriptive grading scale (grades 0 to 3) are included on the case report form (CRF).
1. Corneal staining should be assessed using 1.0 mg sodium fluorescein strips.
2. After wetting the end of the strip with a single drop of buffered saline, the excess is shaken into a waste bin with a sharp flick.
3. The lower lid is then pulled down and the flat end of the tip should be gently applied to the inferior tarsal conjunctiva with the intent of instilling a very small volume of dye and not inducing reflex tearing.
4. The patient will be instructed to blink naturally several times without forced closure of the eyelid to distribute the fluorescein.
5. After allowing fluorescein to remain on the eye for at least one minute, the 5 corneal regions will be graded using a yellow (Wratten #12) barrier filter in conjunction with the cobalt (blue) filter to maximize the view of the fluorescence. The upper eyelid is lifted slightly to grade the entire corneal surface. To enhance the contrast, position the yellow barrier filter in the path of the returning light (not in the path of the incident light).

Tear Film Breakup Time (TFBUT)

TFBUT will be assessed using slit lamp biomicroscopy according to the following steps:
1. The slit-lamp will be set to a magnification of approximately 10×.
2. With adequate fluorescein in place (preferably using DET strips), the subject will be asked to stare straight ahead without blinking until told otherwise. The test should be performed in a room with no direct air on the patient's face.
3. A stopwatch will be used to record the time between the last complete blink and the first appearance of a growing micelle indicating tear-film breakup.
   Note: If the patient blinks prematurely prior to the development of the breakup of the mires, the examiner should continue to try to obtain a reading.
4. Once TFBUT is observed, instruct patient to blink freely. This test should then be repeated a second time on the same eye.
5. If the difference between the first and second readings differs by more than two seconds, a third measurement should be performed and recorded.
6. This procedure will then be performed in the other eye.
7. It is recommended that TFBUT be performed in a room with a temperature of approximately 18 C with a humidity of approximately 50%.

Ocular Surface Staining—Conjunctival Staining Using Lissamine Green

Ocular surface staining assessment will be completed with lissamine green conjunctival staining.
1. The lissamine green ophthalmic strip should be wetted with buffered saline and applied to the inferior tarsal conjunctiva. Care should be taken to instill adequate dye.
2. After allowing lissamine green to remain on the eye for one minute, the six nasal and temporal conjunctival regions will be graded.
3. To grade the temporal zone, the subject should be instructed to look nasally; to grade the nasal zone, the subject should be instructed to look temporally.
4. This procedure should then be completed in the other eye.

Schirmer Test

At screening visit #1, one basal Jones Schirmer test will be performed followed by a Schirmer test with cotton swab nasal stimulation. The Jones Schirmer test with topical anesthetic will be used to assess tear production using the following steps:
1. Topical anesthetic drops such as 0.5% proparacaine hydrochloride or equivalent should be instilled in both eyes of the patient.
2. The patient will be instructed to keep the eyes gently closed for one minute.
3. After opening the eyes and allowing the eyes to recover for approximately one additional minute, excess moisture in the inferior fornix is gently removed with a cotton-tipped applicator.
4. Schirmer strips (35 mm×5 mm size filter paper strip) will be placed in each eye at the junction of the middle and lateral thirds of the lower eye lid.
5. Under ambient light, the patient will be instructed to look forward and to blink normally during the course of the test. The test should be performed in a room with no direct air on the patient's face.
6. After five minutes, strips will be removed from both eyes and the amount of wetting will be recorded. The strips should be taped to the CRF. Note: Should the Schirmer score reach maximum prior to the 5 minute endpoint, the strip can be removed and the time it took to reach maximum recorded. However, the strip from the contralateral eye should not be removed until it too has reached maximum score prior to the 5 minute endpoint.

7. As multiple Schirmer tests are performed, new anesthetic drops should be added as necessary.

Schirmer Test Using Cotton Swab Nasal Stimulation

1. At screening visit #1, the Schirmer test should be performed using cotton swab nasal stimulation. With new strips in place, the examiner should insert cotton swabs in both participant's nostrils simultaneously and gently probe both nasal middle turbinates for approximately 30 seconds. After this, the examiner can simply hold the swabs in place, applying gentle pressure, and repeat probing intermittently as necessary.
2. Alternatively, the participant can be instructed to hold the cotton swabs and gently probe both nasal turbinates simultaneously, resting intermittently before probing again. The examiner should continuously coach the participant on how to perform this test properly.
3. The Schirmer strips should remain in place until five minutes have elapsed or they have reached maximum score.

Both Schirmer scores will be recorded and verified that they meet the inclusion criteria. As two Schirmer tests are performed, new anesthetic drops should be instilled as necessary.

Schirmer Test with Each of Two Nasal Spray Applications

With each of the two nasal applications, the Jones Schirmer test with topical anesthetic will be used to assess tear production using the following steps:

1. Topical anesthetic drops such as 0.5% proparacaine hydrochloride or equivalent should be instilled in both eyes of the participant for each application.
2. The participant will be instructed to keep the eyes gently closed for one minute.
3. After opening the eyes and allowing the eyes to recover for approximately one additional minute, excess moisture in the inferior fornix is gently removed with a spear.
4. Schirmer strips (35 mm×5 mm size filter paper strip) will be placed in each eye at the junction of the middle and lateral thirds of the lower eye lid.
5. Under ambient light, the participant will be instructed to look forward and to blink normally during the course of the test. The test should be performed in a room with no direct air on the participant's face.
6. After five minutes, strips will be removed from both eyes and the amount of wetting will be recorded. The strips should be taped to the CRF.

Dry Eye Provocation and Symptom Assessment

The ClimaTears Goggle System (Biocentric Developments, LLC) will be used to reduce periocular humidity and induce symptoms of dry eye in patients. This system was designed for the purpose of standardizing testing conditions for clinical studies of dry eye patients.

Patients will wear the ClimaTears Goggles continuously for up to 90 min, with their symptoms recorded via the visual analog scale (VAS) every 5 minutes during the testing period. The subject will be asked to rate their dryness symptoms (both eyes simultaneously) by placing a vertical mark on the horizontal line to indicate the level of discomfort. 0 corresponds to "no dryness" and 5 corresponds to "maximal dryness." The assessment line length of the scale will be 100 mm. There are many symptoms of dry eye, including dryness, sticky feeling, burning, foreign body sensation, itching, blurred vision, sensitivity to light, and pain. Please rate the severity of your current "dryness" symptoms (and no others) by drawing a vertical line on the line below:

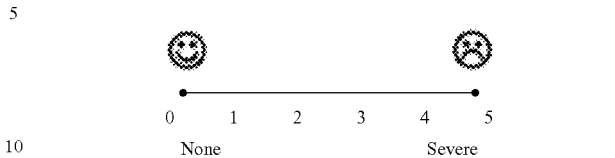

At Day 0, patients will begin wearing the goggles and be monitored until they reach a symptom score of 45 mm or more for two consecutive measurements, at which time they will randomly receive a dose of either OC-04 nasal spray or the control nasal spray, administered 2.5 minutes after the two consecutive 45 mm measurements. Symptoms will be continued to be monitored until the patient again reaches a score of 45 mm or higher for two consecutive measurements, at which time the patient will receive a second nasal dose of which ever test article they did not receive the first time. After the second nasal dose, symptoms will be monitored again until the patient reaches a score of a score of 45 mm or higher for two consecutive measurements. At that time, the goggles will be removed and the test will end. If still ongoing, the test will be terminated after 90 minutes of exposure to the goggles environment. At the end of this period, each patient will be asked to decide which of the nasal sprays made provided more relief of their dry eye symptoms.

At Day 7, patients will begin wearing the goggles and be monitored until they reach a symptom score of 45 mm or more for two consecutive measurements, at which time they will receive a dose of the OC-04 nasal spray. Symptoms will continued to be monitored until the patient again reaches a score of 45 mm or higher for two consecutive measurements, at which time the goggles will be removed and the test will end. If still ongoing, the test will be terminated after 90 minutes of exposure to the goggles environment.

Patients entering with a baseline symptoms score of more than 45 mm will have a treatment threshold equal to this baseline score, and will thus receive treatment after two consecutive symptoms measurements of greater than or equal to this value.

The instructions (in bold above) will be read to the patient before the test begins, and before recording symptoms values immediately following the administration of either nasal spray.

Example 2

OC-01 Formulation

OC-01 contains 0.1% varenicline in sterile phosphate buffered saline (PBS) consisting of 137 mM sodium chloride, 2.7 mM potassium chloride and 10 mM phosphate buffer at pH 7.4 without preservatives. The formulation was packaged in a 20 mL opaque polyethylene nasal spray bottle that delivers a unit dose of 50 microliters. The vehicle control was supplied in the identical packaging. Both OC-01 and vehicle are labeled with a code denoting the contents of the package, which will not be known to the participants or masked study personnel.

Example 3

Additional Pharmaceutical Formulations

To prepare pharmaceutical formulations suitable for administration intranasally, 10 mg of a nicotinic acetylcholine receptor agonist is dissolved in 10 mL of a specified vehicle. 1 mL of this solution is diluted in 9 mL of vehicle to afford a "0.1× dilution" formulation. Following the first dilution, 1 mL of the "0.1× dilution" formulation is diluted in 9 mL of vehicle to afford a "0.01× dilution" formulation. The three formulations with varying concentrations of the nicotinic acetylcholine receptor agonist are stored at 4° C.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical formulation for local administration into the nasal cavity of an individual comprising a non-systemically bio available dose between 5 micrograms and 50 micrograms of varenicline per dose formulated (a) for nasal administration and (b) to prevent desensitization.

2. The pharmaceutical formulation of claim 1, wherein varenicline is formulated in a dosage amount that does not result in undesired psychoactive side effects.

3. The pharmaceutical formulation of claim 1, wherein varenicline is formulated in a dosage amount that does not result in undesired systemic side effects.

4. The pharmaceutical formulation of claim 1, further comprising one or more substances selected from protein kinase C (PKC) or factors that upregulate or up-modulate PKC, cAMP-dependent protein kinase (PKA) or factors that upregulate or up-modulate PKA, and calcineurin inhibitors.

5. The pharmaceutical formulation of claim 4, wherein the calcineurin inhibitor is selected from cyclosporine, pimecrolimus, and tacrolimus.

6. The pharmaceutical formulation of claim 1, wherein varenicline selectively binds to at least one of the peripheral nicotinic acetylcholine receptor subtypes selected from alpha3beta4, alpha4beta2, and alpha7.

7. The pharmaceutical formulation of claim 1, wherein the pharmaceutical formulation comprises about 1 mg/mL of varenicline.

8. The pharmaceutical formulation of claim 1, wherein the pharmaceutical formulation comprises about 0.5 mg/mL of varenicline.

9. The pharmaceutical formulation of claim 1, wherein the formulation is administered at least once daily.

10. The pharmaceutical formulation of claim 1, wherein the formulation is administered at least twice daily.

11. The pharmaceutical formulation of claim 1, wherein the formulation is administered at least once weekly.

12. The pharmaceutical formulation of claim 1, wherein the formulation is administered into the nasal cavity as a liquid, suspension, aerosol, gel, ointment, dry powder, cream, paste, lotion, or balm.

13. The pharmaceutical formulation of claim 1, wherein the formulation is administered into the nasal cavity by a syringe, dropper, bottle nebulizer, atomization pump, inhaler, powder spray device, vaporizer, patch, medicated stick, pipette, or jet of liquid.

* * * * *